United States Patent
Jackson et al.

(10) Patent No.: US 11,751,915 B2
(45) Date of Patent: Sep. 12, 2023

(54) MODULAR SPINAL FIXATION SYSTEM WITH BOTTOM-LOADED UNIVERSAL SHANK HEADS

(71) Applicant: Roger P. Jackson, Prairie Villiage, KS (US)

(72) Inventors: Roger P. Jackson, Prairie Village, KS (US); James L. Surber, Kansas City, KS (US); Nathaniel D. Ginzton, Boise, ID (US)

(*) Notice: Subject to any disclaimer, the term of this patent is extended or adjusted under 35 U.S.C. 154(b) by 0 days.

(21) Appl. No.: 17/861,194

(22) Filed: Jul. 9, 2022

(65) Prior Publication Data

US 2023/0008092 A1 Jan. 12, 2023

Related U.S. Application Data

(60) Provisional application No. 63/220,028, filed on Jul. 9, 2021.

(51) Int. Cl.
*A61B 17/70* (2006.01)
*A61B 17/86* (2006.01)

(52) U.S. Cl.
CPC ...... *A61B 17/7037* (2013.01); *A61B 17/7032* (2013.01); *A61B 17/863* (2013.01); *A61B 17/8605* (2013.01); *A61B 17/864* (2013.01)

(58) Field of Classification Search
CPC .............. A61B 17/7032; A61B 17/7035–7038
See application file for complete search history.

(56) References Cited

U.S. PATENT DOCUMENTS

| | | | |
|---|---|---|---|
| 2,531,892 A | 11/1950 | Reese | |
| 5,209,753 A | 5/1993 | Biedermann et al. | |

(Continued)

FOREIGN PATENT DOCUMENTS

| | | |
|---|---|---|
| DE | 102013204726 | 9/2014 |
| EP | 1857064 | 11/2007 |
| WO | WO 2020/056385 | 3/2020 |
| WO | WO 2021/127251 | 6/2021 |

OTHER PUBLICATIONS

Justis, J. R. et al., "Instruments and Methods for Stabilization of Bony Structures," U.S. Appl. No. 60/160,489, filed Oct. 20, 1999, 34 pages.

(Continued)

*Primary Examiner* — Eduardo C Robert
*Assistant Examiner* — Michelle C Eckman
(74) *Attorney, Agent, or Firm* — Polsinelli PC

(57) ABSTRACT

A modular spinal fixation system for securing an elongate rod to a bone of a patient includes a plurality of bone anchors, each having a universal shank head and an anchor portion opposite the universal shank head configured for fixation to the bone. The system further includes a plurality of pivoting and non-pivoting receiver sub-assemblies, with each receiver sub-assembly including a receiver having an upper portion defining a channel configured to receive the elongate rod and a base defining a lower portion of a central bore communicating with a bottom surface of the receiver through a bottom opening, and one of a shank head-engaging retainer or a rod-engaging insert positioned within the central bore. Each of the universal shank heads is configured for uploading into both the pivoting and non-pivoting receiver sub-assemblies through the bottom opening of the receiver and for axial rotation about a longitudinal axis of the shank relative to the receiver prior to locking the receiver sub-assembly to the head of the shank with the elongate rod and a closure.

16 Claims, 48 Drawing Sheets

(56) References Cited

U.S. PATENT DOCUMENTS

| | | |
|---|---|---|
| 5,545,163 A | 8/1996 | Miller et al. |
| 5,669,911 A | 9/1997 | Errico et al. |
| 5,672,176 A | 9/1997 | Biedermann et al. |
| 5,690,630 A | 11/1997 | Errico et al. |
| 5,716,356 A | 2/1998 | Biedermann et al. |
| 5,725,528 A | 3/1998 | Errico et al. |
| 5,797,911 A | 8/1998 | Sherman et al. |
| 5,885,286 A | 3/1999 | Sherman et al. |
| 5,899,906 A | 5/1999 | Schenk |
| 6,010,503 A | 1/2000 | Richelsoph et al. |
| 6,063,090 A | 5/2000 | Schläpfer |
| 6,074,391 A | 6/2000 | Metz-Stavenhagen et al. |
| 6,090,111 A | 7/2000 | Nichols |
| 6,113,601 A | 9/2000 | Tatar |
| 6,146,383 A | 11/2000 | Studer et al. |
| 6,168,597 B1 | 1/2001 | Biedermann et al. |
| 6,254,602 B1 | 7/2001 | Justis |
| 6,355,040 B1 | 3/2002 | Richelsoph et al. |
| 6,368,321 B1 | 4/2002 | Jackson |
| 6,471,705 B1 | 10/2002 | Biedermann et al. |
| 6,530,929 B1 | 3/2003 | Justis et al. |
| 6,565,565 B1 | 5/2003 | Yuan et al. |
| 6,626,908 B2 | 9/2003 | Cooper et al. |
| 6,635,059 B2 | 10/2003 | Randall et al. |
| 6,716,214 B1 | 4/2004 | Jackson |
| 6,740,086 B2 | 5/2004 | Richelsoph |
| 6,837,889 B2 | 1/2005 | Shluzas |
| 6,945,975 B2 | 9/2005 | Dalton |
| 7,066,937 B2 | 6/2006 | Shluzas |
| 7,087,057 B2 | 8/2006 | Konieczynski et al. |
| 7,144,396 B2 | 12/2006 | Shluzas |
| 7,163,539 B2 | 1/2007 | Abdelgany et al. |
| 7,188,626 B2 | 3/2007 | Foley et al. |
| 7,250,052 B2 | 7/2007 | Landry et al. |
| 7,264,621 B2 | 9/2007 | Coates et al. |
| 7,311,712 B2 | 12/2007 | Dalton |
| 7,377,923 B2 * | 5/2008 | Purcell ............... A61B 17/7038 606/248 |
| 7,445,627 B2 | 11/2008 | Hawkes et al. |
| 7,604,655 B2 | 10/2009 | Warnick |
| 7,662,172 B2 | 2/2010 | Warnick |
| 7,666,189 B2 | 2/2010 | Gerber et al. |
| 7,686,834 B2 | 3/2010 | Saint Martin |
| 7,686,835 B2 | 3/2010 | Warnick |
| 7,695,497 B2 | 4/2010 | Cordaro et al. |
| 7,722,654 B2 | 5/2010 | Taylor et al. |
| 7,749,258 B2 | 7/2010 | Biedermann et al. |
| 7,766,915 B2 | 8/2010 | Jackson |
| 7,766,945 B2 | 8/2010 | Nilsson et al. |
| 7,776,067 B2 | 8/2010 | Jackson |
| 7,789,896 B2 | 9/2010 | Jackson |
| 7,789,900 B2 | 9/2010 | Levy et al. |
| 7,811,310 B2 | 10/2010 | Baker et al. |
| 7,833,250 B2 | 11/2010 | Jackson |
| 7,833,251 B1 | 11/2010 | Ahlgren et al. |
| 7,842,073 B2 | 11/2010 | Richelsoph et al. |
| 7,875,065 B2 | 1/2011 | Jackson |
| 7,901,436 B2 | 3/2011 | Baccelli |
| 7,909,830 B2 | 3/2011 | Frigg et al. |
| 7,914,536 B2 | 3/2011 | MacDonald et al. |
| 7,922,748 B2 | 4/2011 | Hoffman |
| 7,942,909 B2 | 5/2011 | Hammill, Sr. et al. |
| 7,947,065 B2 | 5/2011 | Hammill, Sr. et al. |
| 7,951,173 B2 | 5/2011 | Hammill, Sr. et al. |
| 7,967,850 B2 | 6/2011 | Jackson |
| 7,988,694 B2 | 8/2011 | Barrus et al. |
| 8,021,397 B2 | 9/2011 | Farris et al. |
| 8,048,112 B2 | 11/2011 | Suzuki et al. |
| 8,066,744 B2 | 11/2011 | Justis et al. |
| 8,075,599 B2 | 12/2011 | Johnson et al. |
| 8,075,603 B2 | 12/2011 | Hammill, Sr. et al. |
| 8,083,776 B2 | 12/2011 | Alvarez |
| 8,197,517 B1 | 6/2012 | Lab et al. |
| 8,197,518 B2 | 6/2012 | Hammill, Sr. et al. |
| 8,221,472 B2 | 7/2012 | Peterson et al. |
| 8,353,932 B2 | 1/2013 | Jackson |
| 8,366,753 B2 | 2/2013 | Jackson |
| 8,382,805 B2 | 2/2013 | Wang et al. |
| 8,398,683 B2 | 3/2013 | Berrevoets et al. |
| 8,449,578 B2 | 5/2013 | Keiser et al. |
| 8,540,753 B2 | 9/2013 | Jackson |
| 8,556,938 B2 | 10/2013 | Jackson et al. |
| 8,562,652 B2 | 10/2013 | Biedermann et al. |
| 8,628,558 B2 | 1/2014 | Harvey et al. |
| 8,663,298 B2 | 3/2014 | Keyer et al. |
| 8,696,712 B2 | 4/2014 | Biedermann et al. |
| 8,876,869 B1 | 11/2014 | Schafer et al. |
| 8,882,817 B2 | 11/2014 | Jones et al. |
| 8,888,827 B2 | 11/2014 | Harper et al. |
| 8,926,671 B2 | 1/2015 | Biedermann et al. |
| 8,951,290 B2 | 2/2015 | Hammer et al. |
| 8,986,349 B1 | 3/2015 | German et al. |
| 9,044,272 B2 | 6/2015 | Shaffrey et al. |
| 9,119,674 B2 | 9/2015 | Matthis et al. |
| 9,155,567 B2 | 10/2015 | Auerbach et al. |
| 9,198,695 B2 | 12/2015 | Shluzas et al. |
| 9,254,150 B2 | 2/2016 | Biedermann et al. |
| 9,259,247 B2 | 2/2016 | Chandanson et al. |
| 9,358,047 B2 | 6/2016 | Mishra et al. |
| 9,492,204 B2 | 11/2016 | Biedermann et al. |
| 9,526,529 B2 | 12/2016 | Charvet |
| 9,572,599 B1 | 2/2017 | Casey et al. |
| 9,572,600 B2 | 2/2017 | Biedermann et al. |
| 9,615,858 B2 | 4/2017 | Doubler et al. |
| 9,649,134 B2 | 5/2017 | Hannen |
| 9,655,652 B2 | 5/2017 | Biedermann et al. |
| 9,707,013 B2 | 7/2017 | Rezach et al. |
| 9,763,702 B2 | 9/2017 | Schlaepfer |
| 9,808,292 B2 | 11/2017 | Jackson |
| 9,918,745 B2 | 3/2018 | Jackson et al. |
| 9,924,975 B2 | 3/2018 | Jackson et al. |
| 10,028,770 B2 | 7/2018 | Rezach et al. |
| 10,039,572 B2 | 8/2018 | Harris et al. |
| 10,058,354 B2 | 8/2018 | Jackson et al. |
| 10,064,657 B2 | 9/2018 | Spitler |
| 10,064,658 B2 | 9/2018 | Jackson et al. |
| 10,117,680 B2 | 11/2018 | Trautwein et al. |
| 10,130,396 B2 | 11/2018 | Vedula et al. |
| 10,154,859 B2 | 12/2018 | Keyer et al. |
| 10,172,647 B2 | 1/2019 | Elsbury |
| 10,188,432 B2 | 1/2019 | Jackson et al. |
| 10,285,738 B1 | 5/2019 | Doubler et al. |
| 10,335,203 B2 | 7/2019 | Fiechter et al. |
| 10,335,204 B2 | 7/2019 | Matthis et al. |
| 10,463,402 B2 | 11/2019 | Biester et al. |
| 10,485,594 B2 | 11/2019 | Toon et al. |
| 10,507,043 B1 | 12/2019 | Gladieux |
| 10,517,645 B2 | 12/2019 | van der Pol |
| 10,695,100 B2 | 6/2020 | May et al. |
| 10,792,074 B2 | 10/2020 | Jackson |
| 11,020,150 B1 | 6/2021 | Doubler et al. |
| 11,141,199 B1 | 10/2021 | Doubler et al. |
| 11,234,738 B2 | 2/2022 | Jackson et al. |
| 11,234,745 B2 | 2/2022 | Jackson |
| 11,304,732 B2 | 4/2022 | Mueller et al. |
| 2003/0149431 A1 | 8/2003 | Varieur |
| 2005/0203516 A1 | 9/2005 | Biedermann et al. |
| 2006/0058788 A1 | 3/2006 | Hammer et al. |
| 2006/0084989 A1 * | 4/2006 | Dickinson .......... A61B 17/7037 606/279 |
| 2006/0161152 A1 | 7/2006 | Ensign et al. |
| 2006/0200131 A1 | 9/2006 | Chao et al. |
| 2006/0217716 A1 | 9/2006 | Baker et al. |
| 2006/0241600 A1 | 10/2006 | Ensign et al. |
| 2006/0247631 A1 * | 11/2006 | Ahn .................. A61B 17/7037 606/264 |
| 2007/0016200 A1 * | 1/2007 | Jackson ............. A61B 17/7005 623/17.16 |
| 2007/0118123 A1 | 5/2007 | Strausbaugh et al. |
| 2007/0270807 A1 | 11/2007 | Armstrong et al. |
| 2007/0270813 A1 | 11/2007 | Garamszegi |
| 2008/0009862 A1 * | 1/2008 | Hoffman ............ A61B 17/7037 606/278 |
| 2008/0147129 A1 | 6/2008 | Biedermann et al. |

(56) References Cited

U.S. PATENT DOCUMENTS

| | | | |
|---|---|---|---|
| 2008/0300634 A1* | 12/2008 | Gray | A61F 2/4455 606/264 |
| 2010/0094353 A1* | 4/2010 | Shim | A61B 17/7032 606/301 |
| 2010/0152787 A1 | 6/2010 | Walsh et al. | |
| 2013/0218213 A1 | 8/2013 | Lemoine | |
| 2014/0025119 A1 | 1/2014 | Biedermann et al. | |
| 2015/0088202 A1* | 3/2015 | Charvet | A61B 17/7037 606/279 |
| 2015/0282843 A1* | 10/2015 | Spitler | A61B 17/7037 606/279 |
| 2016/0317206 A1 | 11/2016 | Rezach et al. | |
| 2021/0401467 A1 | 12/2021 | Jackson et al. | |
| 2022/0061892 A1 | 3/2022 | Jackson et al. | |

OTHER PUBLICATIONS

Justis, J. R. et al., "Instruments and Methods for Stabilization of Bony Structures," U.S. Appl. No. 60/186,729, filed Mar. 3, 2020, 47 pages.

Landry M. E. et al., "Spinal stabilization system using polyaxial members," U.S. Appl. No. 60/422,455, filed Oct. 30, 2002, 97 pages.

Landry M. E. et al., "Spinal stabilization systems and methods using minimally invasive surgical procedures," U.S. Appl. No. 60/466,091, filed Apr. 28, 2003, 131 pages.

Landry M. E. et al., "Spinal stabilization systems and methods using minimally invasive surgical procedures," U.S. Appl. No. 60/471,254, filed May 16, 2003, 139 pages.

* cited by examiner

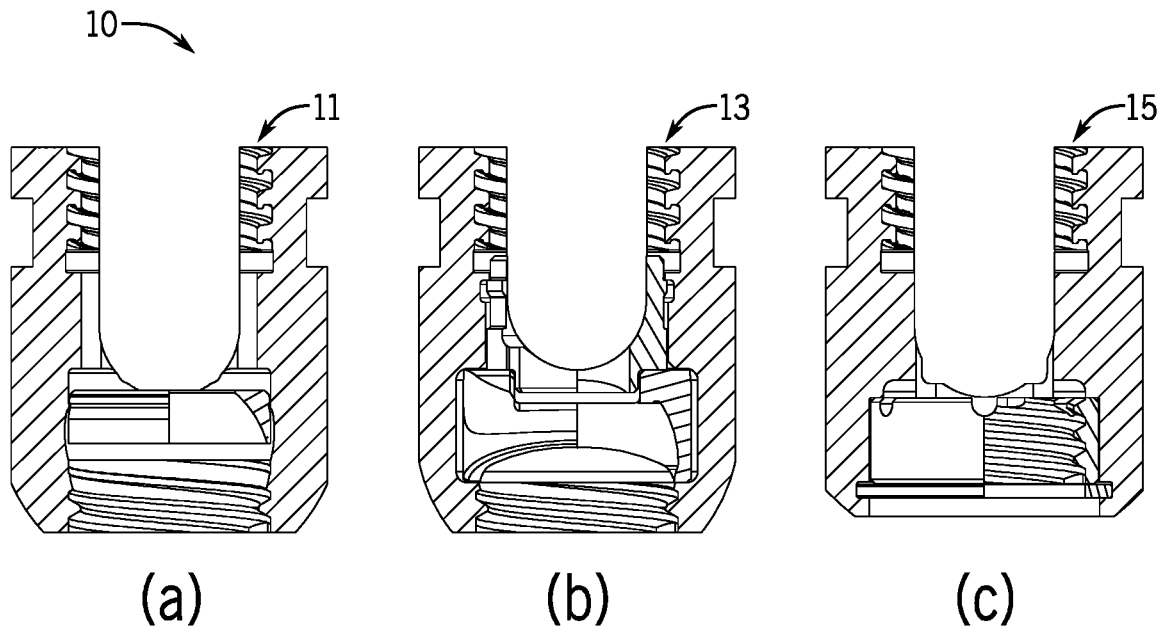
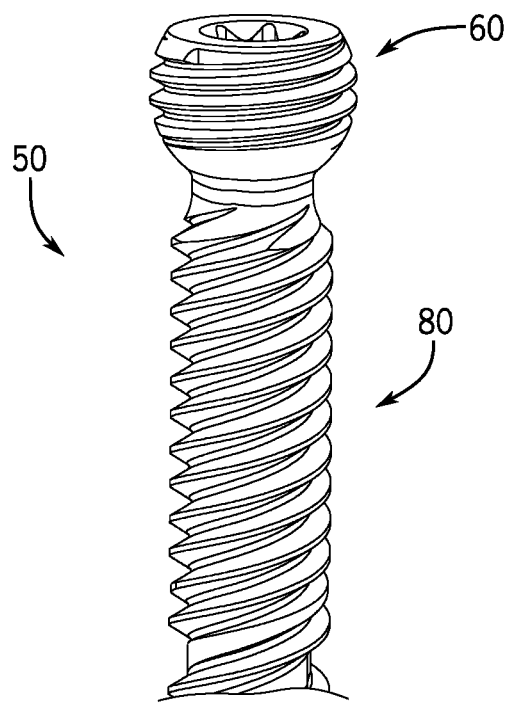
FIG. 1

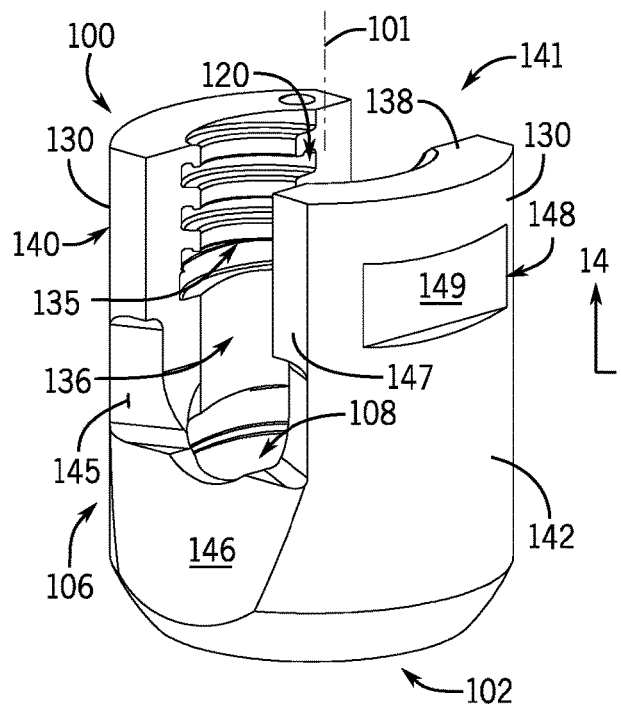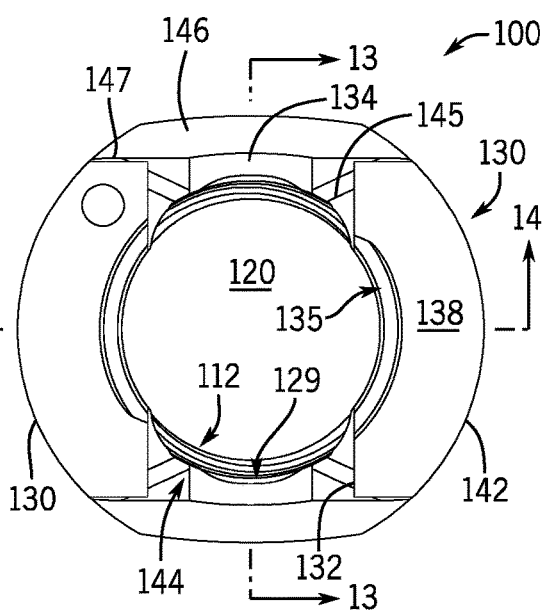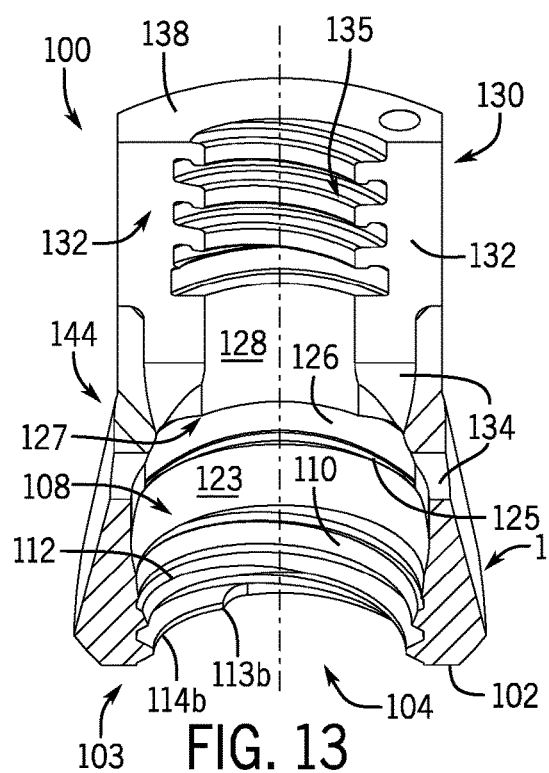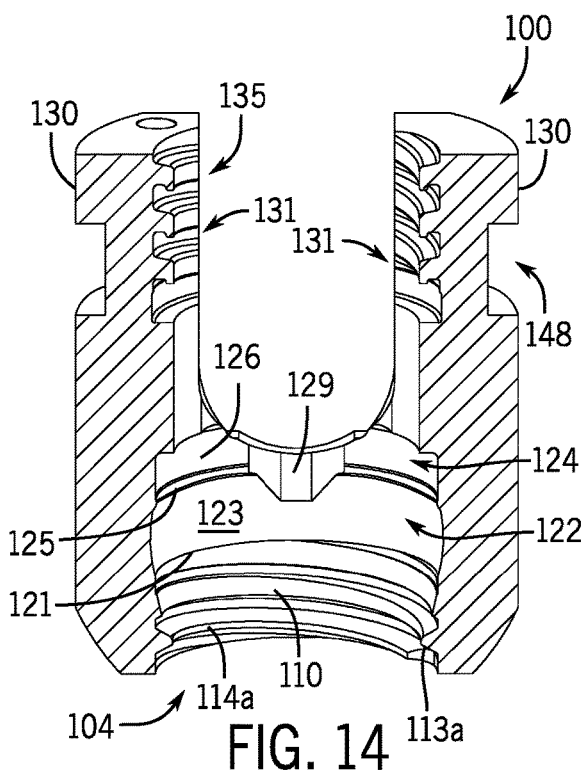

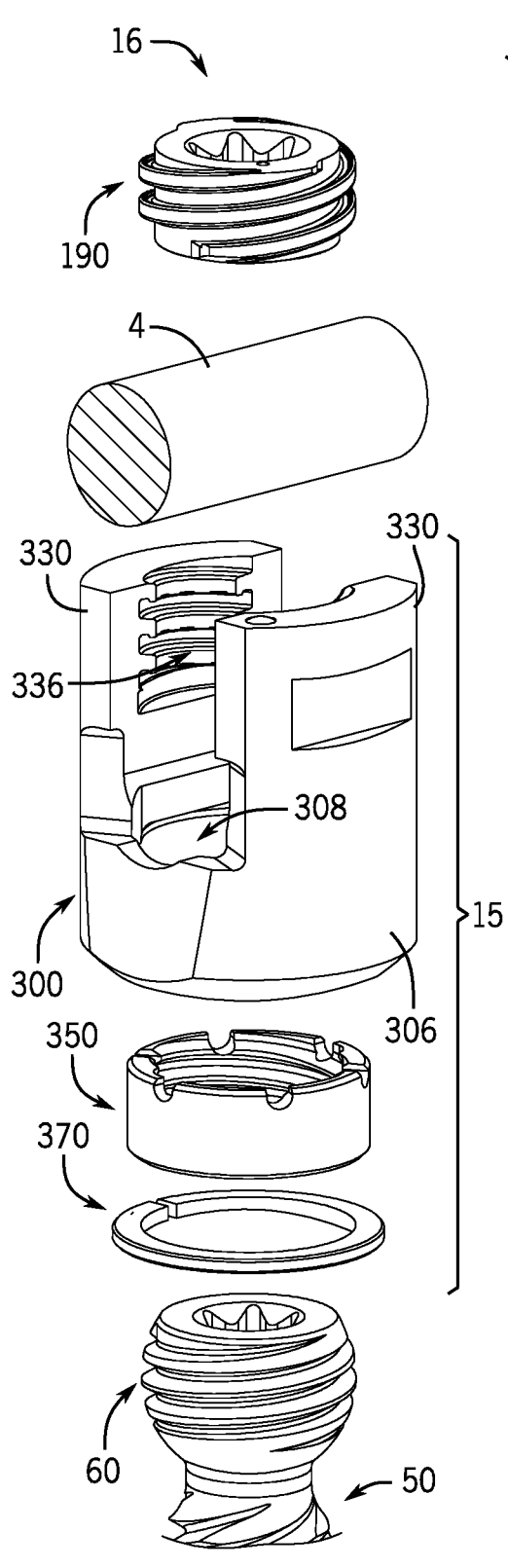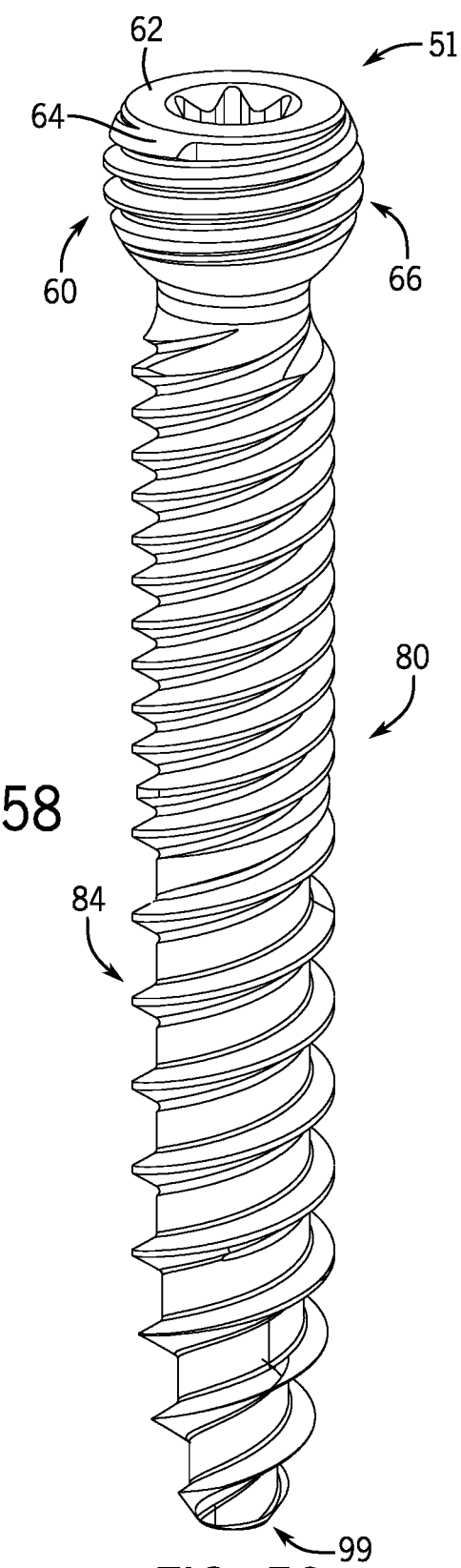
FIG. 58
FIG. 59

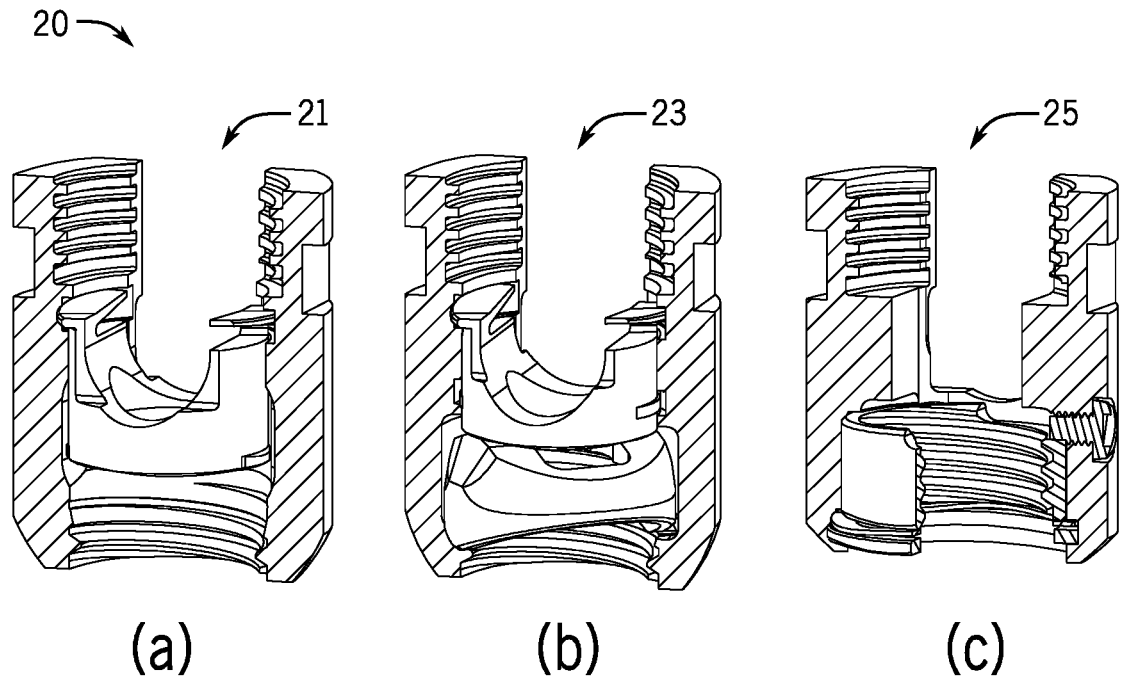
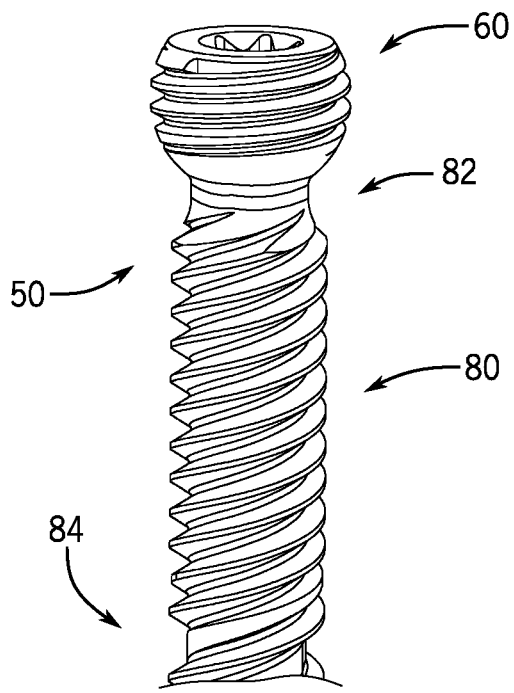
FIG. 71

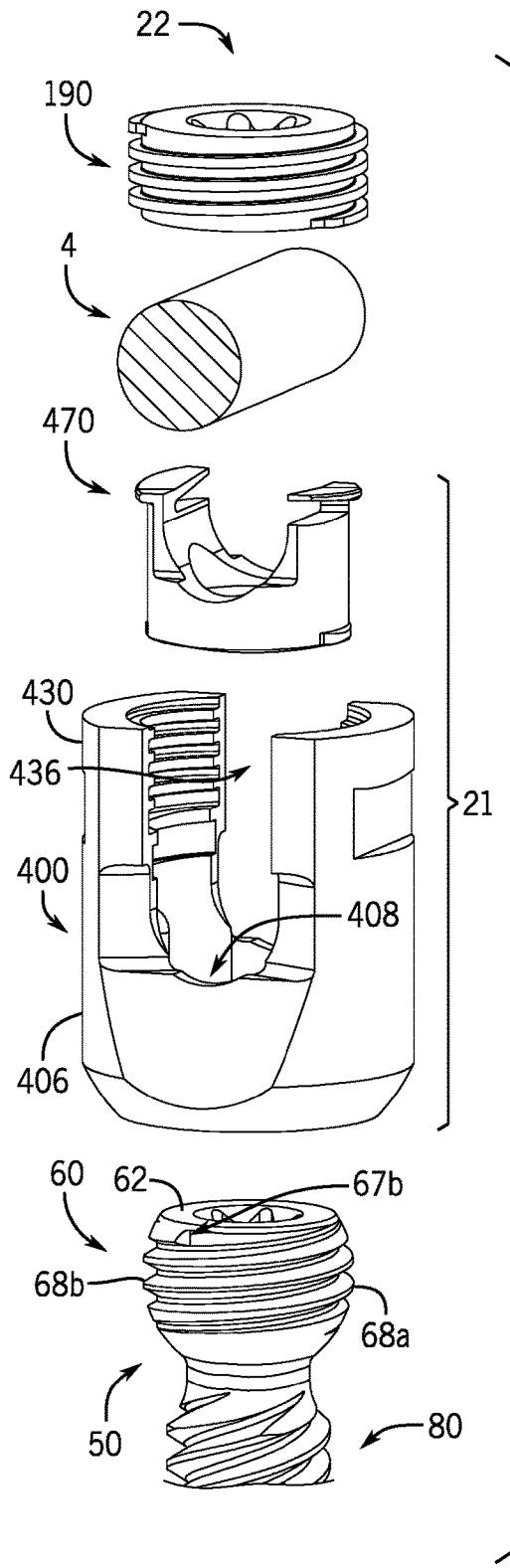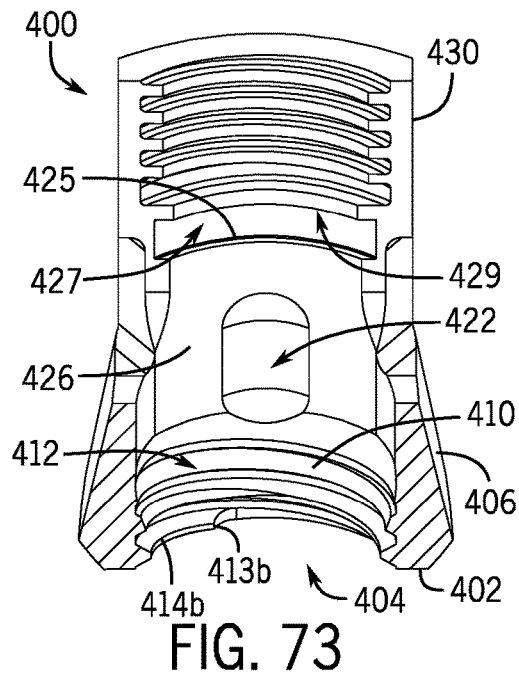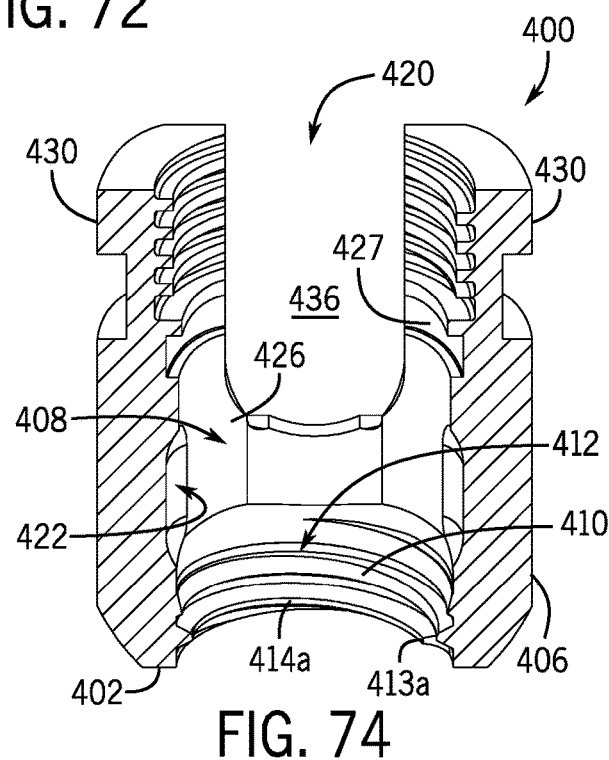
FIG. 72
FIG. 73
FIG. 74

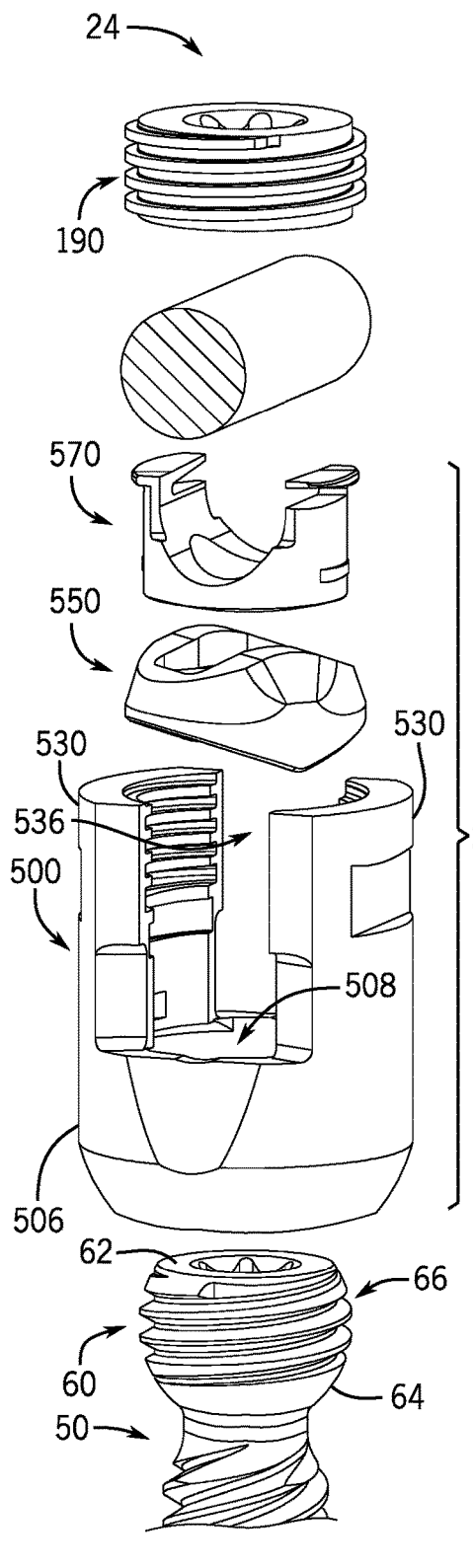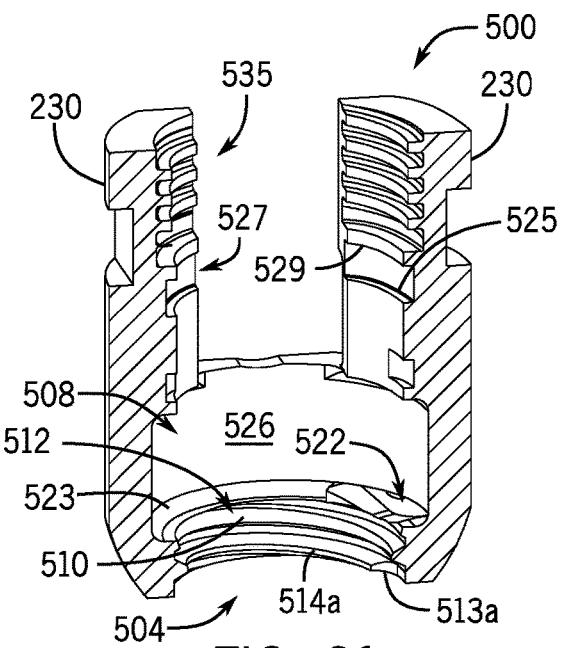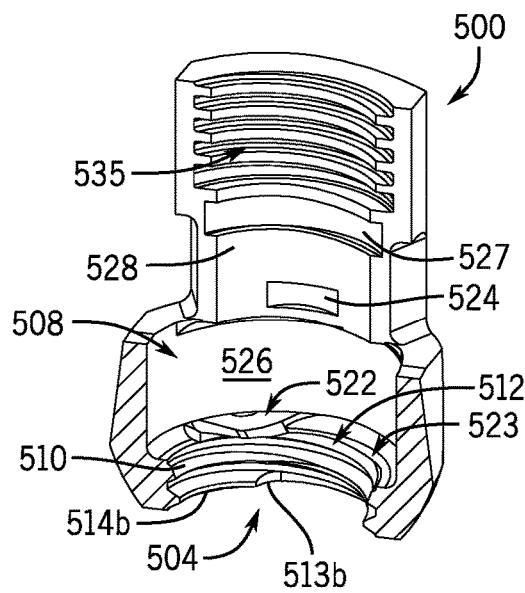
FIG. 90
FIG. 91
FIG. 92

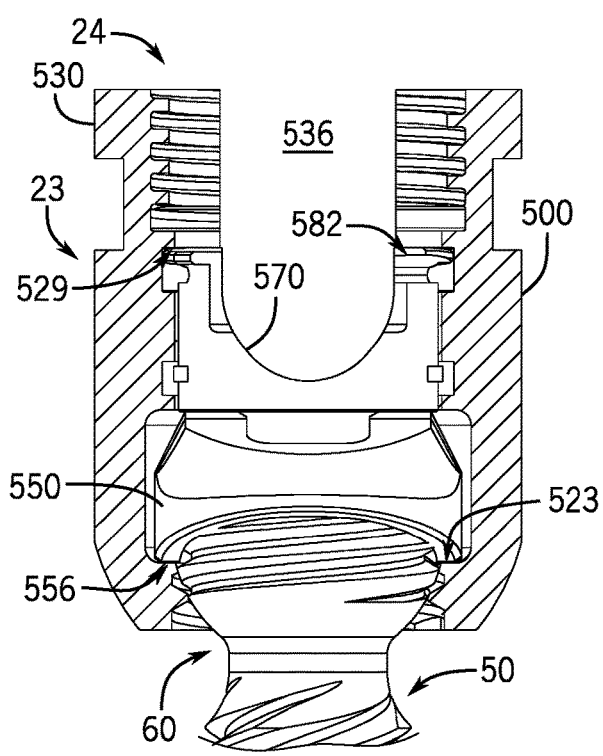
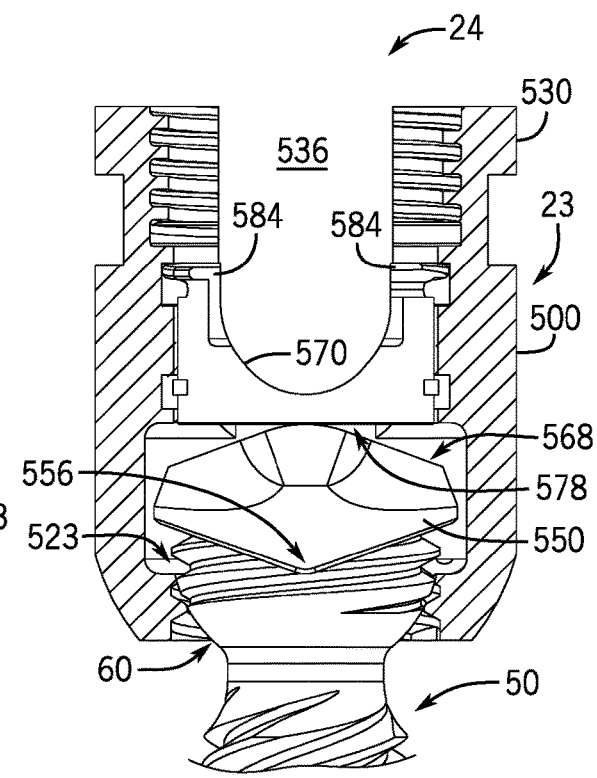
FIG. 109  FIG. 110
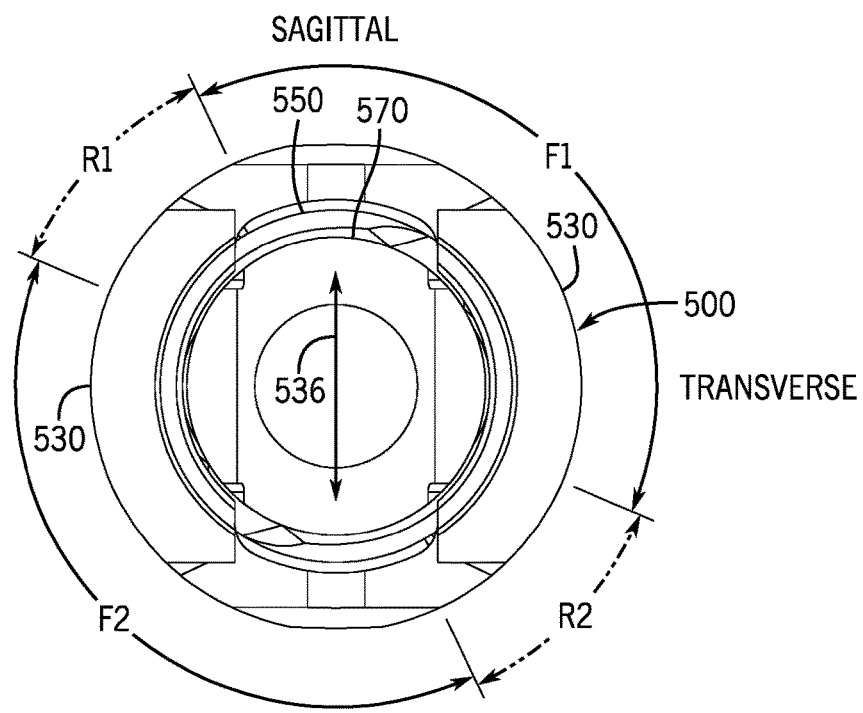
FIG. 111

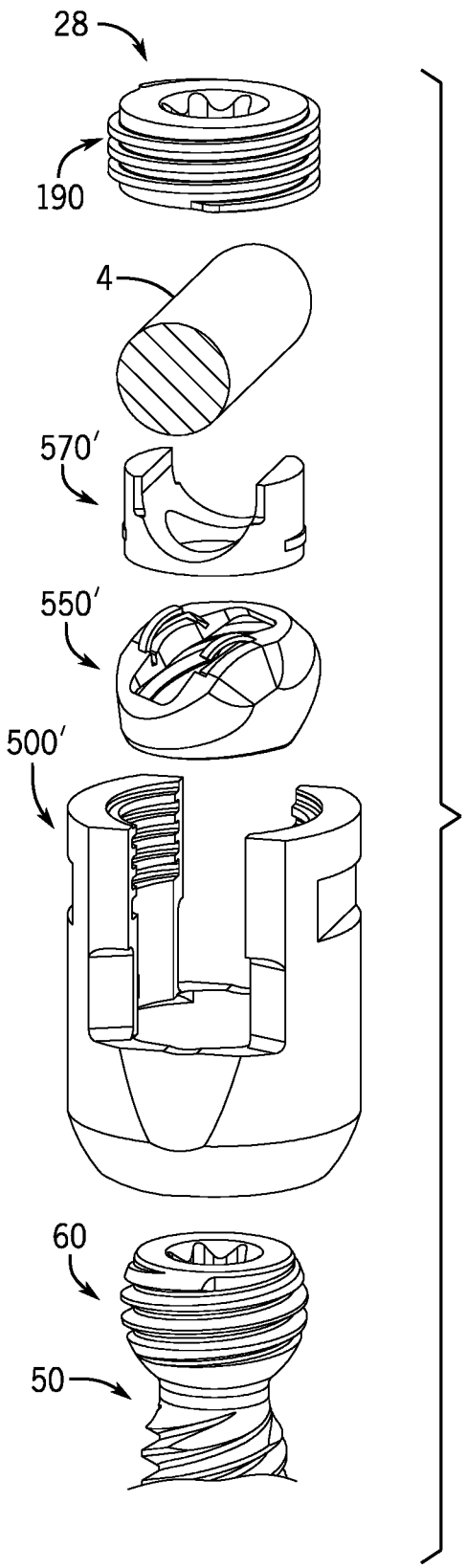
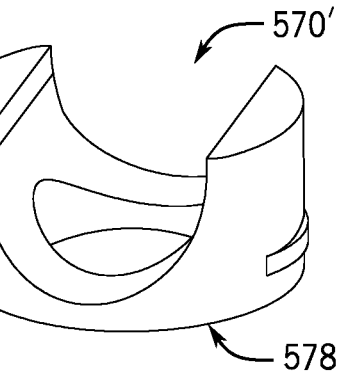
FIG. 114
FIG. 113
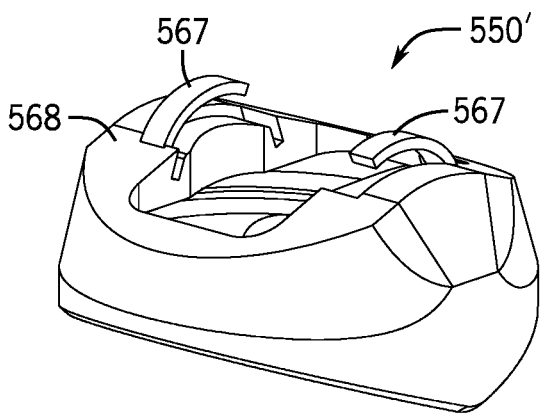
FIG. 115

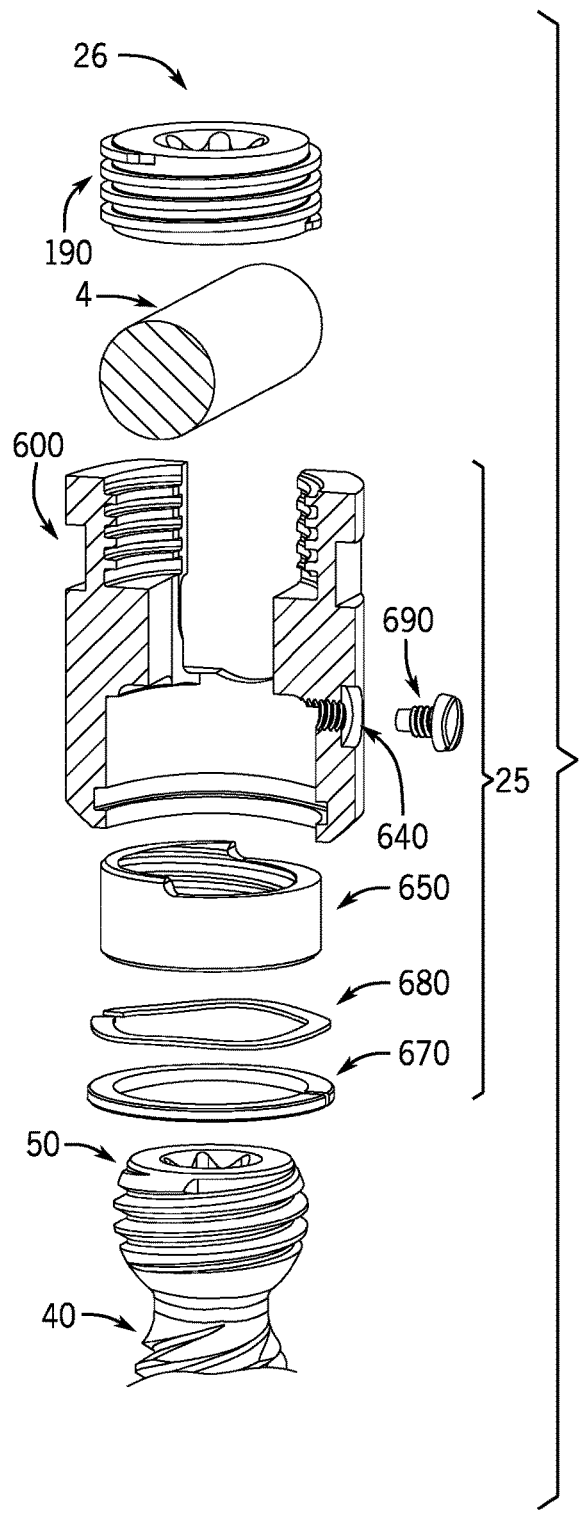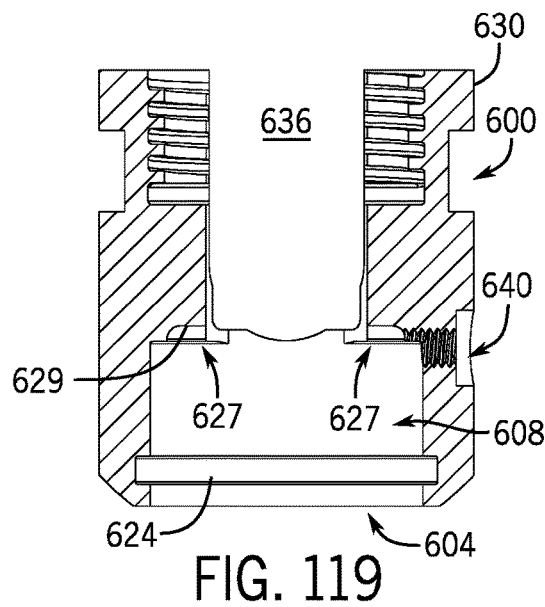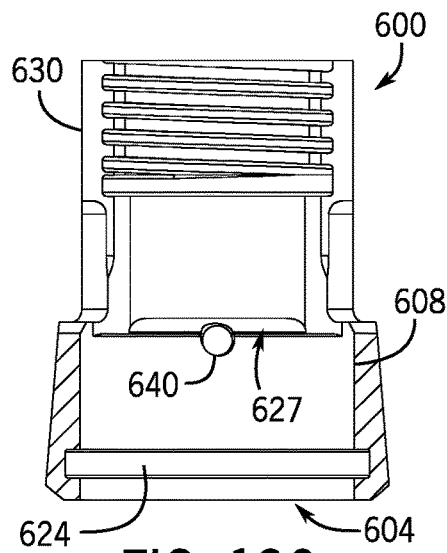
FIG. 118
FIG. 119
FIG. 120

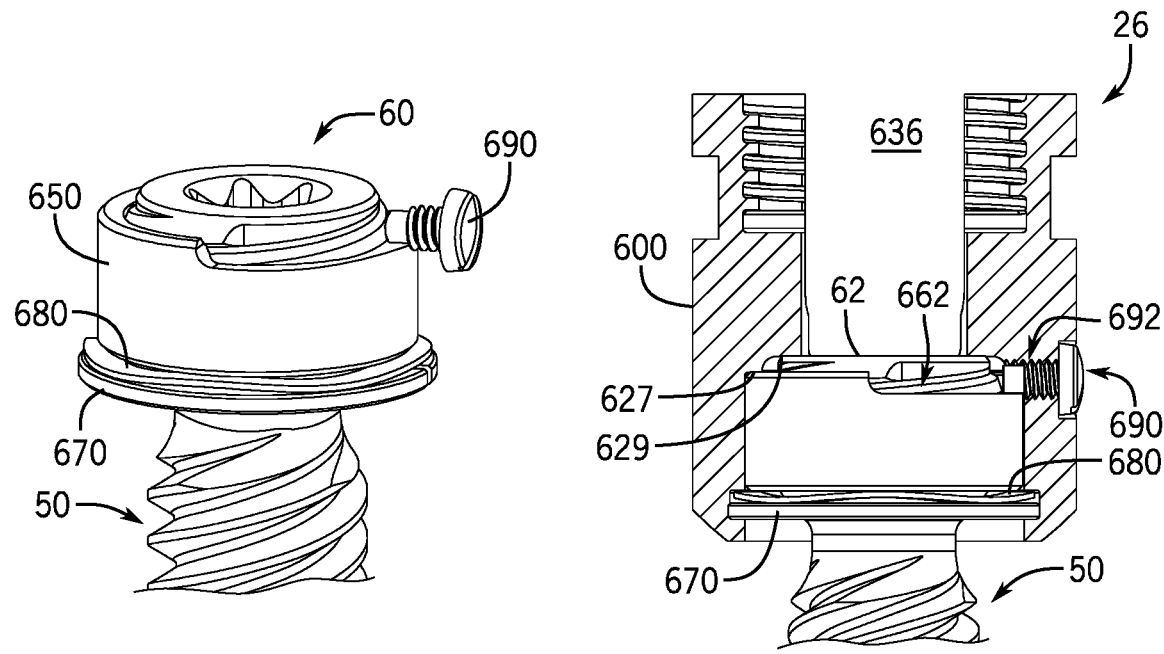
FIG. 126
FIG. 127
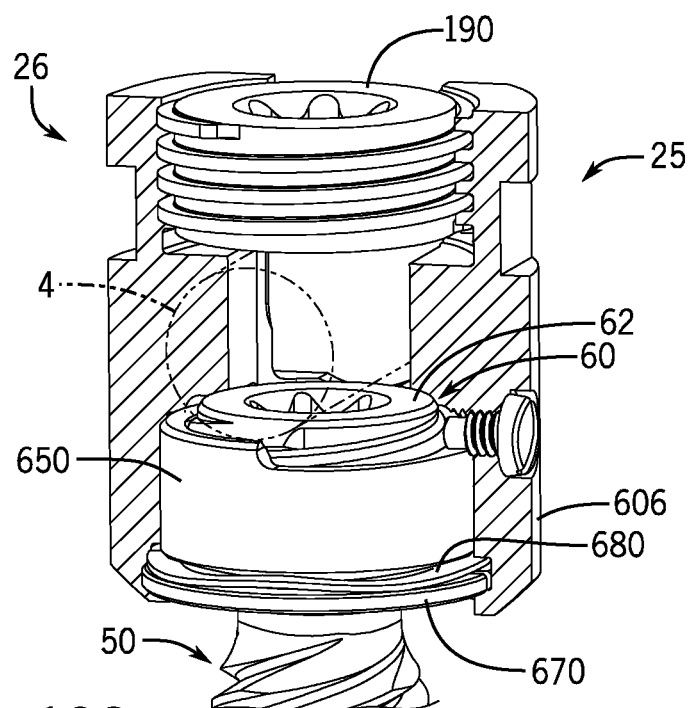
FIG. 128

MODULAR SPINAL FIXATION SYSTEM WITH BOTTOM-LOADED UNIVERSAL SHANK HEADS

CROSS-REFERENCE TO RELATED APPLICATIONS

This application claims the benefit of U.S. Provisional Application No. 63/220,028, filed Jul. 9, 2021, which is incorporated by reference in its entirety herein and for all purposes.

FIELD OF THE INVENTION

The present disclosure relates generally to bone anchor assemblies and their use in spinal surgery involving vertebral stabilization.

BACKGROUND

Spinal implants in general, and bone anchors or screws in particular, are used in many types of spinal surgery in order to secure various implants to vertebrae along the spinal column for the purpose of stabilizing and/or adjusting spinal alignment. Although both closed-ended and open-ended bone screws are known, open-ended screws can be particularly well suited for connections to rods and connector arms because such rods or arms do not need to be passed through a closed bore, but rather can be laid or urged into an open channel within a receiver or head of such a screw. Typical open-ended bone screws include a threaded shank connected to a receiver with a pair of upwardly-projecting branches or arms that form a yoke defining a slot or channel that can have different shapes, such as, for example, a U-shape or a square shape, to receive a rod. Hooks and other types of bone anchors or connectors, as are also used in spinal fixation techniques, may also include open ends for receiving rods or portions of other structure.

A common mechanism for providing vertebral support is to implant the bone screws into certain bones which then in turn support a longitudinal structure such as an elongate rod, or are supported by such a rod. Bone screws of this type may have a fixed head or receiver relative to a shank thereof. In the fixed bone screws, the fixed head cannot be moved relative to the shank and the rod must be favorably positioned in order for it to be placed within the rod-receiving channel. This is sometimes very difficult or impossible to do. Therefore, pivotal, multiaxial, or polyaxial bone anchors or screws, or bone anchor assemblies, are commonly preferred. Open-ended polyaxial bone screw assemblies typically allow for pivoting and rotation of the separate receiver (or receiver sub-assembly) about the head or upper capture portion of the shank in one or more planes, until a desired rotational position of the receiver is achieved. This can be accomplished by fixing the position of the receiver relative to the shank upon its initial assembly with the head or upper capture portion of the shank, and/or during a final stage of a medical procedure when an elongate rod or other longitudinal connecting member is inserted into the receiver, followed by a locking set screw, a plug, a closure, or other type of locking mechanism known in the art.

The above-referenced spinal implants, or bone anchor assemblies, generally include a variety of components that require some assembly, such as rods, receivers, shanks, and closures or plugs, with each having specific features with respect to structure and function. Moreover, the receivers can further include additional sub-components, such as pressure inserts, spring rings and separate retainers of different types that are operable to connect the heads of the threaded shanks or bone anchors with the receivers. The inserts, rings, and retainers can be top or bottom loaded into the receivers, and once pre-assembled together within the receivers can define receiver sub-assemblies in a shipping state configuration, in which the receiver sub-assemblies are ready for final assembly with the shanks and the closures or plugs.

The shanks can also be top or bottom loaded into the receiver sub-assemblies. With bottom loaded bone anchor assemblies, for example, some designs known in the art require a separate retainer to hold the shank in the receiver sub-assembly (which retainer may or may not pivot with respect to the receiver), with the receiver having a bottom opening large enough to allow for the head or upper capture portion of the shank to be uploaded into the central bore or cavity of the receiver. There are other types of bottom loaded bone anchor assemblies that do not include a separate retainer, however, and instead include a receiver having a bottom opening that is configured to directly threadably mate with the head or upper capture portion of the shank that is, in turn, configured as a threaded spherical head.

Further to the above, bottom loaded bone anchor assemblies can be fully assembled by the company before being shipped to a hospital, or can be shipped as a modular array of separate shanks and pre-assembled receiver sub-assemblies that can then be fully assembled, for example, at the hospital or surgical center during a surgery. Additionally, the modular spinal implants can be fully assembled at the hospital either before insertion into the patient, or after the separate shank or bone screw has been inserted into the patient. The different procedures for the assembly of the modular parts of the bone anchor assemblies can be described as ex-vivo and in-vivo, respectively.

Depending on the design of the various parts and components of the bone anchor assembly, the bottom loading of the head or upper capture portion of the shank into a receiver sub-assembly may not be easy, especially with in-vivo assemblies and particularly when threads are involved, wherein getting the threads aligned and started can frequently be difficult given the surgical environment in which they are being used. Consequently, a need exists for an apparatus and method for providing an easier and more reliable engagement of the male and female threads, as well as a faster connection of the modular parts so as to save time during surgeries, which can also be important. It is toward such an apparatus and method that the present disclosure is directed.

SUMMARY

Briefly described, one embodiment of the present disclosure comprises a modular spinal fixation system for securing an elongate rod to a bone of a patient. The system includes a plurality of bone anchors, with each bone anchor having a universal shank head and an anchor portion opposite the universal shank head configured for fixation to the bone. The system further includes a plurality of pivoting and non-pivoting receiver sub-assemblies, with each receiver sub-assembly including a receiver with an upper portion defining a channel configured to receive the elongate rod and a base defining a lower portion of a central bore communicating with a bottom surface of the receiver through a bottom opening, and one of a shank head-engaging retainer or a rod-engaging insert positioned within the central bore. Furthermore, each of the universal shank heads is configured for uploading into both the pivoting and non-pivoting receiver sub-assemblies through the bottom opening of the receiver and for axial rotation about a longitudinal axis of the shank relative to the receiver prior to locking the receiver sub-assembly to the head of the shank with the elongate rod and a closure.

Another embodiment of the present disclosure comprises a pivotal bone anchor assembly that generally includes a shank having a longitudinal axis, a shank head at a proximal end having a rounded shape, and an anchor portion at a distal end that is configured for fixation to the bone of a patient. The shank head further includes a planar top surface at an upper end, a rounded outer side surface extending downward from the top surface to a neck portion that connects the shank head to the anchor portion, and a pair of helically wound upper threadforms located on the rounded outer side surface and extending upwards towards the top surface, with each upper threadform having an upper start structure with a concave surface adjacent the top surface.

The bone anchor assembly also includes a receiver with an upper portion defining a channel that is configured to receive an elongate rod, and a base defining a lower portion of a central bore that is formed around a vertical centerline axis and communicating with a bottom surface of the receiver through a bottom opening. The central bore extends upwardly from the bottom opening through the channel to a top of the receiver and includes a rounded lower seating surface adjacent the bottom opening, and a pair of helically wound lower threadforms located on the rounded lower seating surface and extending downwards into the bottom opening, with each lower threadform having a lower start structure adjacent the bottom surface. Rotation of the bottom opening of the receiver against the proximal end of the shank head is configured to simultaneously mate the upper starts of the shank head with the lower starts of the receiver, respectively, so as to threadably engage the shank head with the bottom opening for threadable uploading of the shank head into the central bore of the receiver.

Yet another embodiment of the disclosure comprises a modular spinal fixation or bone anchor system for securing an elongate rod to a spine of a patient that includes a plurality of bone anchors, with each bone anchor having a threaded universal shank head at a proximal end and an anchor portion at a distal end that is configured for fixation to one of the bones of the spine of the patient. The threaded universal shank head further includes a planar top surface at an upper end, a rounded outer side surface extending downward from the top surface to a neck portion that connects the shank head to the anchor portion, and at least one helically wound upper threadform located on the rounded outer side surface and extending upwards toward an upper start structure located adjacent the top surface.

The modular bone anchor system also includes one or more multiplanar or polyaxial receiver sub-assemblies, with each multiplanar receiver sub-assembly including a multiplanar receiver having an upper portion with a channel configured to receive the elongate rod, a base portion defining a lower portion of a central bore having a rounded lower seating surface adjacent a bottom opening that is configured to receive and support the threaded universal shank head of one of the bone anchors, and at least one helically wound lower threadform located on the rounded lower seating surface and extending downwards into the bottom opening toward a lower start structure adjacent a bottom surface of the multiplanar receiver. Each multiplanar receiver sub-assembly also includes a multiplanar insert positionable with the central bore of the multiplanar receiver above the threaded universal shank head with an upper surface configured for engagement by the elongate rod and a lower surface configured to engage the threaded universal shank head while providing for multiplanar pivotal motion of the multiplanar receiver relative to the bone anchor prior to locking the multiplanar receiver sub-assembly with a closure.

The modular bone anchor system further includes one or more monoplanar or uniplanar receiver sub-assemblies, with each monoplanar receiver sub-assembly including a monoplanar receiver having an upper portion with a channel configured to receive the elongate rod, a base portion defining a lower portion of a central bore having a rounded lower seating surface adjacent a bottom opening that is configured to receive and support the threaded universal shank head of another bone anchor, and at least one helically wound lower threadform located on the rounded lower seating surface and extending downwards into the bottom opening toward a lower start structure adjacent the bottom surface of the monoplanar receiver. Each monoplanar receiver subassembly also includes a monoplanar insert positionable with the central bore of the receiver above the threaded universal shank head with an upper surface configured for engagement by the elongate rod and a lower surface configured to engage the threaded universal shank head of the second bone anchor while providing for monoplanar pivotal motion of the monoplanar receiver relative to the bone anchor prior to locking the monoplanar receiver sub-assembly with a closure.

The modular bone anchor system further includes one or more non-pivotal or monoaxial receiver sub-assemblies, with each non-pivotal receiver sub-assembly including a non-pivotal receiver having an upper portion with a channel configured to receive the elongate rod and a base portion defining a lower portion of a central bore having a bottom opening. Each non-pivotal receiver sub-assembly also includes a rotatable sleeve or retainer configured for uploading into the lower portion of the central bore and having a threaded central aperture with a bottom end centralized within the bottom opening of the non-pivotal receiver, and at least one helically wound lower threadform formed into the threaded central aperture and extending downwards toward a lower start structure formed into the bottom end of the central aperture. Each of the threaded universal shank heads is configured for threaded uploading into the threaded central aperture of the rotatable sleeve, with the rotatable sleeve being configured to provide for non-pivotal but axially rotatable motion of the non-pivotal receiver about the longitudinal axis of the uploaded bone anchor prior to locking the at least one non-pivotal receiver sub-assembly with a closure.

Additional aspects and features of the present disclosure will be apparent from the detailed description set forth below taken in conjunction with the accompanying drawing figures, which are briefly described as follows.

BRIEF DESCRIPTION OF THE DRAWINGS

FIG. 1 is an exploded perspective view of a spinal fixation system, in accordance with a representative embodiment of the present disclosure.

FIG. 11 is perspective view of the multiplanar receiver shown in FIG. 2.

FIG. 12 is a top view of the multiplanar receiver of FIG. 11.

FIG. 13 is a cross-sectional perspective side view of the multiplanar receiver of FIG. 11.

FIG. 14 is a cross-sectional perspective front view of the multiplanar receiver of FIG. 11.

FIG. 58 is an exploded perspective view of the non-pivotal bone anchor assembly of the spinal fixation system of FIG. 1, in accordance with another representative embodiment of the present disclosure.

FIG. 59 is a perspective view of the bone anchor or shank shown in FIG. 58 having a threaded universal shank head.

FIG. 71 is an exploded perspective view of another spinal fixation system, in accordance with yet another representative embodiment of the present disclosure.

FIG. 72 is an exploded perspective view of the multiplanar pivotal bone anchor assembly of the spinal fixation system of FIG. 71, in accordance with another representative embodiment of the present disclosure.

FIG. 73 is a cross-sectional perspective side view of the multiplanar receiver of FIG. 72.

FIG. 74 is a cross-sectional perspective front view of the multiplanar receiver of FIG. 72.

FIG. 90 is an exploded perspective view of the monoplanar pivotal bone anchor assembly of the spinal fixation system of FIG. 71, in accordance with another representative embodiment of the present disclosure.

FIG. 91 is a cross-sectional perspective front view of the monoplanar receiver of FIG. 90.

FIG. 92 is a cross-sectional perspective side view of the monoplanar receiver of FIG. 90.

FIG. 109 is a partially cut-away front view of the aforementioned monoplanar receiver sub-assembly and the threaded universal shank head after being threadably coupled together.

FIG. 110 is another partially cut-away front view of the aforementioned monoplanar receiver sub-assembly and the threaded universal shank head after being threadably coupled together.

FIG. 111 is a schematic figure showing the range of rotation of the lower turret piece and shank relative to the monoplanar receiver.

FIG. 113 is an exploded perspective view of the monoplanar pivotal bone anchor assembly of the spinal fixation system of FIG. 71, in accordance with another representative embodiment of the present disclosure.

FIG. 114 is an upper perspective view of the upper insert piece of the monoplanar insert shown in FIG. 113.

FIG. 115 is an upper perspective view of the lower turret piece of the monoplanar insert shown in FIG. 113.

FIG. 118 is an exploded perspective view of the non-pivotal bone anchor assembly of the spinal fixation system of FIG. 71, in accordance with another representative embodiment of the present disclosure.

FIG. 119 is a cross-sectional front view of the non-pivotal receiver of FIG. 118.

FIG. 120 is a cross-sectional side view of the non-pivotal receiver of FIG. 118.

FIG. 121 is an upper perspective view of the rotatable sleeve shown in FIG. 118.

FIG. 122 is an upper perspective view of the wave spring shown in FIG. 118.

FIG. 123 is a side view of the wave spring shown in FIG. 118.

FIG. 124 is a partially cut-away lower perspective view of the non-pivotal receiver of FIG. 118 after assembly of the rotatable sleeve, wave spring, and snap-in-place retainer into the central bore of the non-pivotal receiver to form the completed non-pivotal receiver sub-assembly.

FIG. 125 is a partially cut-away upper perspective view of the non-pivotal receiver of FIG. 118 after assembly of the rotatable sleeve, wave spring, and snap-in-place retainer into the central bore of the non-pivotal receiver to form the completed non-pivotal receiver sub-assembly.

FIG. 126 is a close-up perspective view of the rotatable sleeve, wave spring, and snap-in-place retainer assembled with the threaded universal shank head.

FIG. 127 is a partially cut-away front view of the aforementioned non-pivotal receiver sub-assembly and the threaded universal shank head after being threadably coupled together.

FIG. 128 is a partially cut-away perspective view of the aforementioned non-pivotal receiver sub-assembly and shank after assembly together and with the elongate rod and closure of FIG. 118 into a fully assembled and locked non-pivotal bone anchor assembly.

FIG. 129 is an upper perspective view of a multiplanar pressure ring, in accordance with another representative embodiment of the present disclosure.

FIG. 130 is a partially cut-away front view of a multiplanar bone anchor assembly showing the multiplanar pressure ring of FIG. 129.

FIG. 131 is another partially cut-away front view of a multiplanar bone anchor assembly showing the multiplanar pressure ring of FIG. 129.

Figure 132:
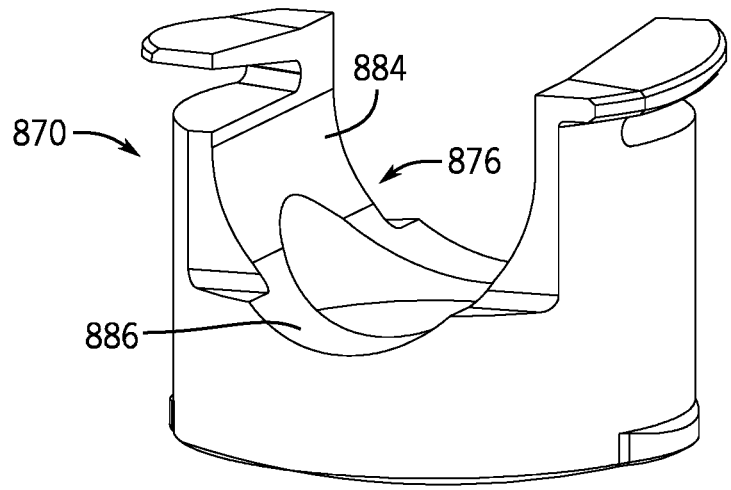

FIG. 132 is an upper perspective view of an axially biasing multiplanar insert, in accordance with another representative embodiment of the present disclosure.

Figures 133, 134:
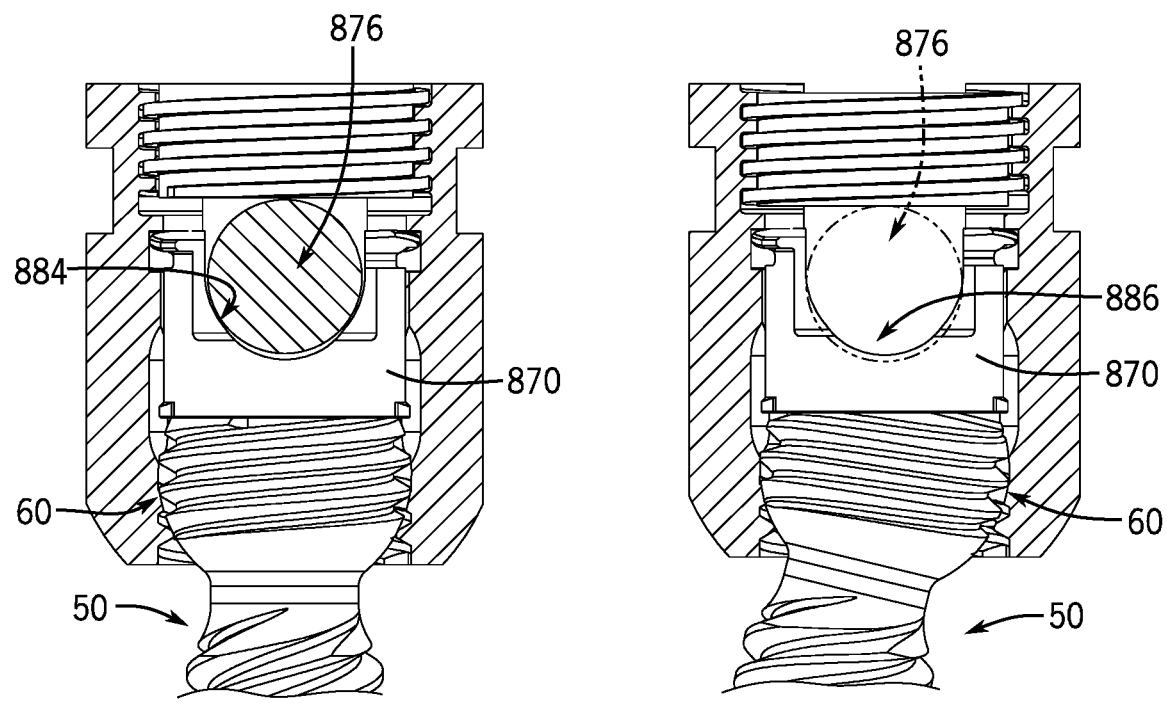

FIG. 133 is a partially cut-away front view of a multiplanar bone anchor assembly showing the multiplanar insert of FIG. 132.

FIG. 134 is another partially cut-away front view of a multiplanar bone anchor assembly showing the multiplanar insert of FIG. 132.

Figure 135:
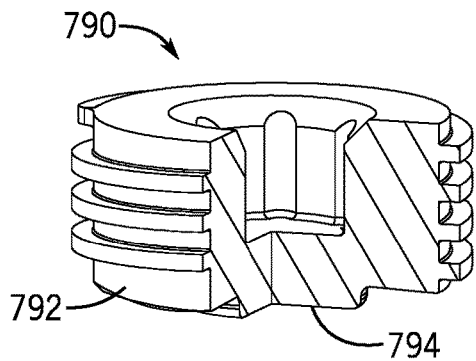

FIG. 135 is a partially cut-away perspective view of a single piece closure.

Figure 136:
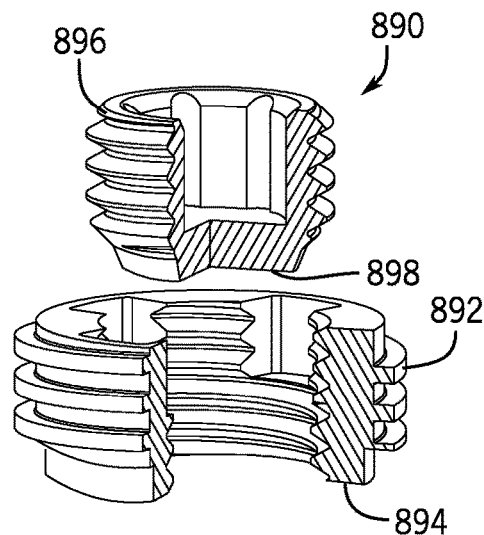

FIG. 136 is a partially cut-away perspective view of a two piece closure.

Figure 137:
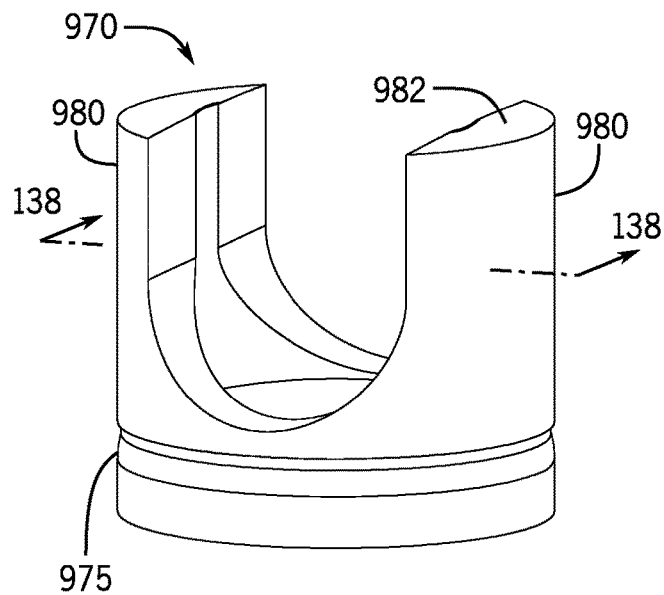

FIG. 137 is an upper perspective view of a multiplanar insert.

Figure 138:
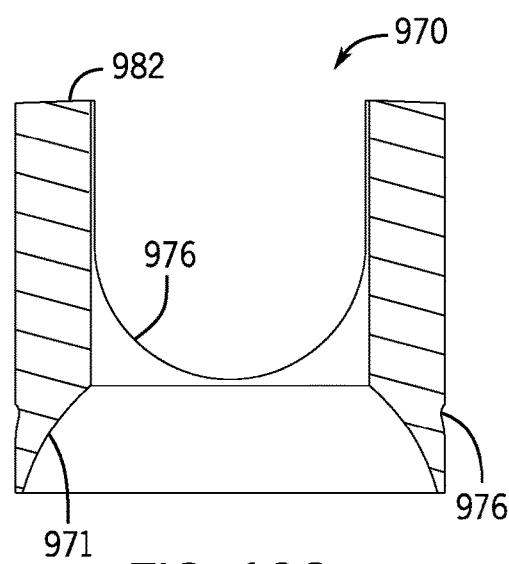

FIG. 138 is a cross-sectional side view of the multiplanar insert of FIG. 137.

Figure 139:
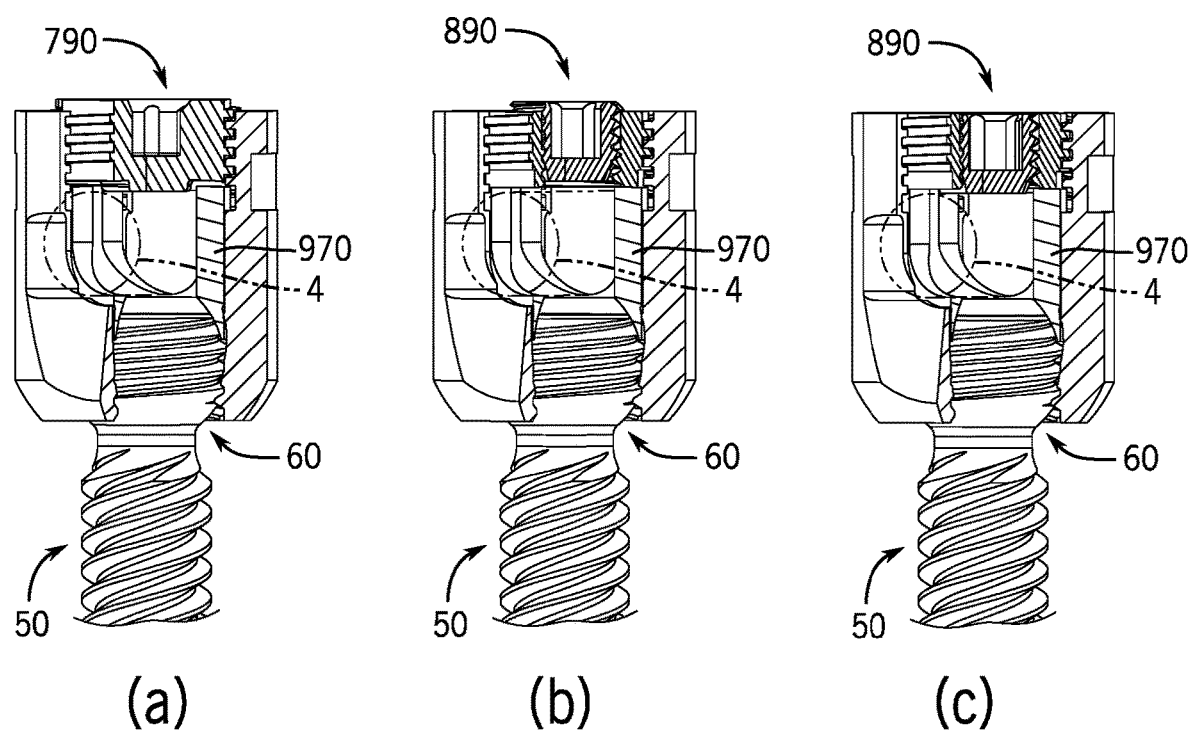

FIG. 139 are partially cut-away perspective views of a multiplanar bone anchor assembly showing combinations of the aforementioned closures and insert, in accordance with another representative embodiment of the present disclosure.

Those skilled in the art will appreciate and understand that, according to common practice, various features and elements of the drawings described above are not necessarily drawn to scale, and that the dimensions and relative positions between the features or elements may be expanded, reduced or otherwise altered to more clearly illustrate the various embodiments of the present disclosure depicted therein.

DESCRIPTION OF THE INVENTION

The following description, in conjunction with the accompanying drawings, is provided as an enabling teaching of bone anchors having a representative type of universal shank head configured for use with an array or collection of complementary pivotal and non-pivotal receiver sub-assemblies in a modular spinal fixation system, together with methods for assembling and employing the bone anchors and receiver sub-assemblies into a spinal construct for securing elongate rods to patient bone in spinal surgery. As described below, the individual bone anchor assemblies, systems, and/or methods for the modular spinal fixation system and the universal shank head disclosed herein can provide several significant advantages and benefits over other pivotal and/or non-pivotal bone anchors and spinal fixation systems known in the art due to, in one aspect, the degree of versatility and adaptability provided by the shank head universality (i.e. a shank head having a standard geometry that is connectable with each of the complementary receiver sub-assemblies) that is incorporated into the different embodiments of the modular spinal fixation system. The recited advantages are not meant to be limiting in any way, however, as one skilled in the art will appreciate that other advantages and benefits may also be realized upon practicing the present disclosure.

Furthermore, those skilled in the relevant art will recognize that changes can be made to the representative embodiments of the modular spinal fixation system and universal shank head of the present disclosure, beyond those described, while still obtaining the beneficial results. It will also be understood and appreciated that some of the advantages and benefits of the embodiments can be obtained by selecting some of the features (e.g. elements, structures, or components) of the disclosed receiver sub-assemblies without utilizing other features, and that features from one sub-assembly embodiment may be interchanged or combined with features from other sub-assemblies in any appropriate combination. For example, any individual feature or collective features of method embodiments may be applied to apparatus, product or system embodiments, and vice versa. Likewise, structural or functional features from one embodiment may also be combined with or replaced by structural or functional features from one or more alternative embodiments in any suitable manner. Those who work in the art will therefore recognize that many modifications and adaptations to the representative embodiments described herein are possible and may even be desirable in certain circumstances, and are to be considered part of the present disclosure. It will thus be appreciated that the present disclosure is provided as an illustration of the principles for the representative embodiments of the modular spinal fixation system and universal shank head shown and discussed therein, since the scope of the invention is to be defined by the claims.

With initial reference to FIG. 1, the present disclosure generally relates to a modular spinal fixation system 10 and associated methods for performing spinal fixation surgeries with the use of bone anchor assemblies having bone attachment structures 50 (such as screws, hooks, shanks, and other known anchor components) attached to longitudinal connecting members (such as rods, cords, connectors, and other known longitudinal connecting members) with threaded universal shank heads 60 that can be bottom loaded into receiver sub-assemblies (i.e. housings or heads), and wherein the receiver sub-assemblies and at least some of their associated internal components can pivot and/or rotate axially in different selected directions relative to their bone attachment structures. More specifically, receivers that are configured to provide different functionalities, such as multiplanar pivotal movement, monoplanar pivotal movement, non-pivotal but axial rotatable movement (i.e. monoaxial), pre-lock friction fit with or without tool deployment, provisional independent locking, and the like, can be pre-assembled with their internal components into receiver sub-assemblies that are configured to be threaded onto the same type of threaded universal shank head, or upper end capture portion geometry, of one or more bone attachment structures. This allows for the bone attachment structures 50 (which can be cannulated) to be affixed to the bony anatomy either before or after being connected with their respective pivoting or non-pivoting receiver sub-assemblies. For instance, in some cases it may be desirable to implant or attach the bone attachment structures 50 into or on the spine of the patient independent of their larger and somewhat bulky receiver sub-assemblies, and decide later on in the surgical procedure where each of the multiplanar receiver sub-assemblies 11, monoplanar receiver subassemblies 13, or non-pivotal receiver sub-assemblies 15 should be placed and utilized on the implanted spinal construct. This type of modular capability can be advantageous for both midline and pedicle screw placement trajectories into the vertebral bodies.

The modular spinal fixation system 10 shown in FIG. 1 is directed toward eliminating or at least improving upon shortcomings of the prior art through the introduction of a bone attachment structure, such as a bone screw 50, having an upper end capture structure 60 comprising a threaded "universal" shank head with both modularity and bone debris clearance capabilities. As described below, the type of threaded universal shank head 60 of the present disclosure is generally configured to be cleared of bone debris and soft tissue simultaneous during the process or motion of being upwardly threadably rotated into either a multiplanar receiver sub-assembly 11, a monoplanar receiver sub-assembly 13, or a non-pivotal receiver sub-assembly 15. Moreover, and as noted above, each of the different types of receiver sub-assemblies can further include a pre-lock friction fit feature that can be created with or without tool deployment and prior to securing the elongate rod within the receiver sub-assembly with the closure.

With reference to FIG. 1(a), for instance, the representative embodiment of the multiplanar pivotal and axially rotatable receiver sub-assembly 11 can be combined with a bone screw 50 having the threaded universal shank head 60 to form a multiplanar pivotal bone anchor assembly 12 further described in reference to FIGS. 2-44. The multiplanar pivotal bone anchor assembly 12 can include components having features or aspects configured to provide for pre-lock frictional pivotal motion of the bone anchor relative to the receiver sub-assembly around a 360-degree range, and also to provide for pre-lock frictional axial rotation relative to a longitudinal axis of the bone anchor around a 360-degree range, and is hereinafter interchangeably referred to as a polyaxial, multi-axial, or 'multiplanar' pivotal bone anchor assembly.

Similarly, the representative embodiment of the monoplanar pivotal and independently axially rotatable receiver sub-assembly 13 shown in FIG. 1(*b*) can be combined with the same threaded universal bone screw 50 to form a monoplanar pivotal bone anchor assembly 14 further described in reference to FIGS. 45-57. The monoplanar pivotal bone anchor assembly 14 can include alternative components having features or aspects configured to limit the pre-lock frictional pivotal motion of the bone anchor relative to the receiver sub-assembly (or vice versa) to a single plane (i.e. sagittal, medial-lateral) while still providing for pre-lock frictional axial rotation around a 360-degree range, and is hereinafter interchangeably referred to a uniplanar or "monoplanar" pivotal assembly. In one aspect the pivot plane of the monoplanar assembly 14 can be fixed relative to the transverse axis of the channel of the receiver using a rocker-type lower insert body. As shown in the drawings, the threaded universal shank head or capture portion of the universal bone screw can be included into this monoplanar functionality without the use of parallel flat or planar side surfaces formed into the outer surfaces of the capture portion.

Likewise, the representative embodiment of the non-pivotal but axially rotatable receiver sub-assembly 15 shown in FIG. 1(*c*) can be combined with the same threaded universal shank head 60, or upper end capture portion geometry, to form a non-pivotal bone anchor assembly 16 further described in reference to FIGS. 58-70. The non-pivotal bone anchor assembly can also include alternative components having features or aspects configured to prevent or inhibit pivotal motion of the bone anchor relative to the receiver sub-assembly (or vice versa) while still providing for pre-lock frictional axial rotation around a 360-degree range, and is hereinafter interchangeably referred to as a non-pivotal, fixed, or 'monoaxial' assembly with some possible limited toggle. Again, as shown in the drawings, the universal shank head or capture portion of the universal bone screw can be included into this non-pivotal monoaxial functionality without the use of parallel flat or planar side surfaces formed into the outer surfaces of the capture portion.

Thus, regardless of the type, degree or amount of pivotal motion, each of the three major motion modalities or embodiments is configured to provide a bone anchor assembly wherein the bone anchor can axially rotate around its longitudinal or spin axis relative to the receiver sub-assembly (or vice versa) at least prior to locking the bone anchor assembly with the closure in the final locked position and generally with at least some degree of a pre-lock axial friction fit. It will be appreciated that this feature can allow for the rotatable implantation, or screwing in, of only the anchor portion of a pre-assembled bone anchor assembly to a desired depth in the bone of a patient without rotation of its respective receiver sub-assembly, thereby allowing the receiver sub-assembly to be secured by separate tooling, or maintained in a desired alignment, throughout the rotatable implantation of the bone anchor. In addition, this feature can also allow for the height of the receiver sub-assembly above the bone, or the length of the anchor portion of the bone anchor that is implanted in the bone, to be more precisely controlled, and wherein more aggressive thread forms having larger pitches for faster insertions with fewer rotations can also be utilized, especially with robot assisted surgeries. The upper end capture portion geometry of the screw can further provide for a very strong and secure connection with a driving tool for manual or robotic insertions.

Figure 2:
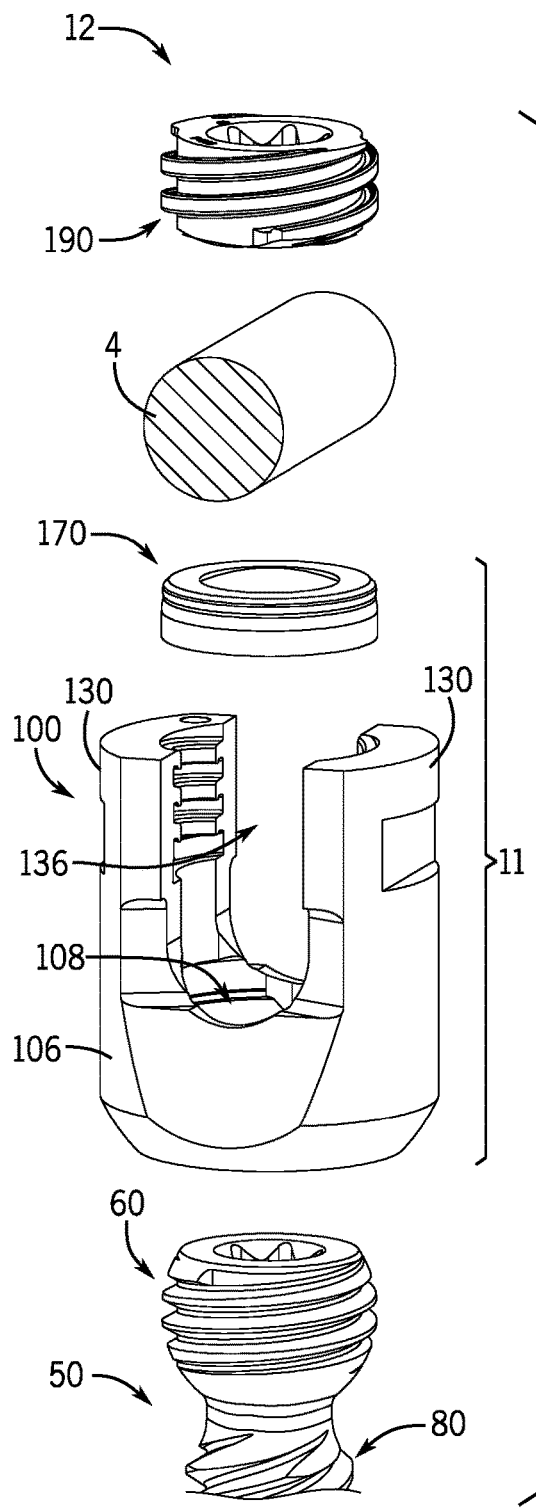
FIG. 2 is an exploded perspective view of the multiplanar pivotal bone anchor assembly of the spinal fixation system of FIG. 1, in accordance with another representative embodiment of the present disclosure.

Referring now in more detail to the drawing figures, wherein like parts are identified with like reference numerals throughout the several views, FIG. 2 illustrates one representative embodiment of a multiplanar pivotal bone anchor apparatus or assembly 12 for securing an elongate rod 4 to the bone of a patient. The multiplanar assembly 12 generally includes a bone anchor, such as a shank 50 having a capture portion or head 60 with a rounded shape at a proximal end 51, and a body 80 extending distally from the threaded head 60 with an anchor portion 84 at a distal end 99 that is configured for securement to the bone. As discussed in detail below, the threaded head 60 of the shank 50 can further include an annular planar top surface 62 at an upper end and a pair of helically wound upper threadforms 68*a*, 68*b* formed into a rounded or partial spherical outer surface 64 that extends to the top surface 62, with each of the upper threadforms 68*a*, 68*b* having an upper start structure or 'start' extending upwards towards the top surface 62 of the shank head 60 (see FIGS. 5-7).

The multiplanar bone anchor assembly 12 also includes a receiver 100 having a cylindrical base portion 106 defining an internal cavity 108 portion of a central bore, and two upright arms 130 extending upwardly from the base portion 106 to define a rod channel 136 configured for receiving the elongate rod 4. As discussed in detail below, the internal cavity 108 further includes a bottom opening 104 and a pair of helically wound lower threadforms 114*a*, 114*b* located on a partial spherical lower seating surface 110 adjacent the bottom opening 104, with each of the pair of lower threadforms 114*a*, 114*b* having a lower start structure or 'start' extending downwards into the bottom opening of the receiver (see FIGS. 15-18).

The multiplanar bone anchor assembly 12 can further include a multiplanar insert, such as pressure ring 170, that can be pre-assembled into the rod channel 136 and internal cavity 108 of the receiver to form the receiver sub-assembly 11, after which the threaded universal shank head 60 of the shank 50 (also referenced hereinafter as the shank head 60) can be threadably uploaded into the internal cavity 108 and pivotably coupled or secured to the multiplanar receiver sub-assembly 11.

Upon the multiplanar receiver sub-assembly 11 being coupled to the threaded universal shank head 60, the elongate rod 4 can be positioned within the rod channel 136 and a closure 190 can then be threadably or otherwise secured into the rod channel 136 above the elongate rod 4 so as to apply a force or pressure against an upper surface of the elongate rod 4. This force or pressure is transmitted downward through the elongate rod 4, the pressure ring 170, the shank head 60, and ultimately through to a lower portion of the receiver 100, thereby locking both the elongate rod 4 and the multiplanar bone anchor assembly 12 into a final locked position.

Figure 3:
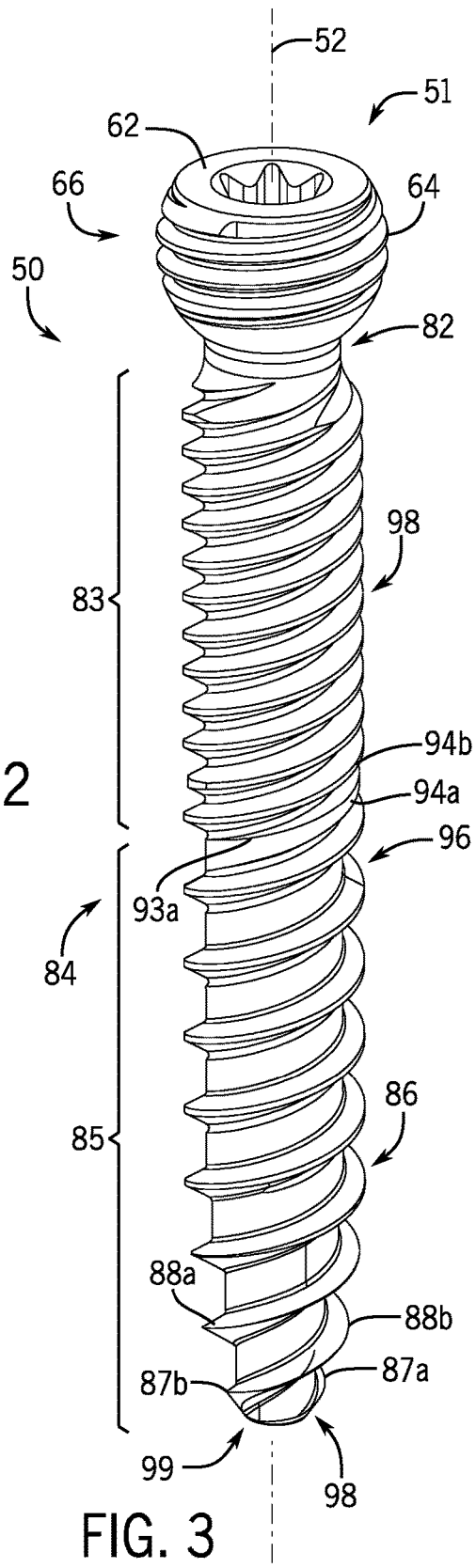
FIG. 3 is a perspective view of the bone anchor or shank shown in FIG. 2 having a threaded universal shank head.
Figure 4:
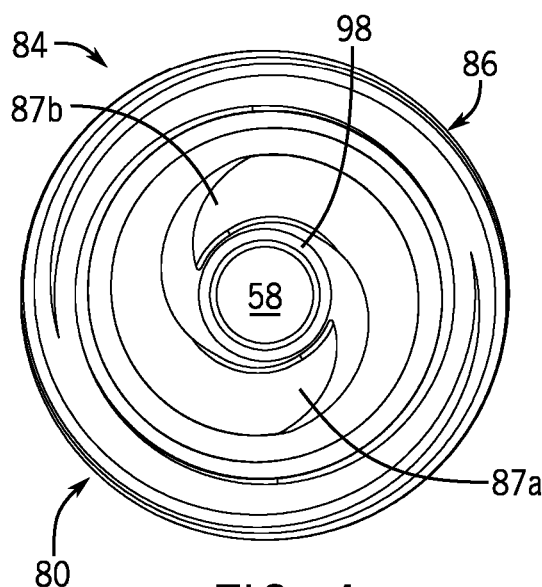
FIG. 4 is a bottom view of the shank of FIG. 3.

With reference to FIG. 3, the shank 50 or bone anchor can have a generally-spherical capture portion or head 60 at a proximal end 51 that includes a plurality of threads formed therein, and an elongate body 80 (also referenced as the shank body 80) extending distally from the shank head 60 with a threaded anchor portion 84 extending toward a distal end 99 that is configured for fixation to the bone of a patient. The shank 50 generally has a longitudinal axis 52, or axis of rotation, extending from the shank head 60 at the proximal end 51 down through the distal tip 98 at the distal end 99. In one aspect the body 80 of the shank 50 can comprise both the anchor portion 84 and a narrower neck portion 82 extending longitudinally between the anchor portion 84 and the shank head 60. Although shown in the figures as an elongate shank body 80 with bone engagement threads, it is foreseen that in other embodiments of the bone anchor that the anchor portion could also be configured as a hook blade extending upwardly to the narrower neck portion 82, a spinal implant configured as a lateral rod connector, and the like.

The shank body 80 can have a first bone implantable thread form 86 (hereinafter also referenced as "the first implantable thread form 86"), which may be a single-, dual-, or multiple-lead thread form, each thread form beginning from a respective start at or near the distal tip 98 and extending to near the neck portion 82 located adjacent the shank head 60. In the illustrated embodiment, the first implantable thread form 86 is a dual-lead helically wound thread form having first and second threads 88a, 88b and respective first and second starts or run-outs 87a, 87b (see FIG. 4). The shank body 80 may also include a second bone implantable thread form 92 (hereinafter also referenced as "the second implantable thread form 92"), which may be a single-, dual-, or multiple-lead thread form, each thread form beginning from a respective start at an intermediate location on the anchor portion 84 of the shank body 80 and extending to near the neck 82. In the illustrated embodiment, the second implantable thread form 92 is a dual-lead helically wound thread form having third and fourth threads 94a, 94b and respective third and fourth starts 93a, 93b.

In one aspect the anchor portion 84 of the shank body 80 can be divided into a upper anchor portion 83 and an lower anchor portion 85 by a transition area 96, defined by the length of the shank body between the third and fourth starts 93a, 93b. In the illustrated embodiment, the third and fourth starts 93a, 93b lie together in a single plane that is orthogonal to the longitudinal axis 52. In other embodiments not shown, the third and fourth starts may be axially spaced apart. As shown in FIG. 3, the first implantable thread form 86 can have a constant lead as it extends through both the lower anchor portion 85 and the upper anchor portion 83. The upper anchor portion 83 can have both the first implantable thread form 86 and the second implantable thread form 92 extending through it compared to the lower body 85, giving the combined first and second thread forms 86, 92 of the upper shank body 83 twice the pitch as first thread form 86 of the lower anchor portion 85.

In one aspect the greater number of threads in the upper anchor portion 83 may provide better anchoring in cortical bone tissue compared to the smaller number of threads in the lower anchor portion 85, which may provide better anchoring in cancellous bone tissue. The location of the transition area 96 may be defined by a ratio of the length of the upper anchor portion 83 divided by the length of the lower anchor portion 85. This ratio may vary from 0.1 to 0.9. In the illustrated embodiment, the ratio is approximately 0.45. During use, the anchor portion 84 may be driven into the patient bone leading with the distal tip 98 using an installation or driving tool (not shown). The first and second implantable thread forms 86, 92 may then be advanced into the vertebra to near the neck 82 of the shank 50 for fixation to the patient bone.

Figure 5:
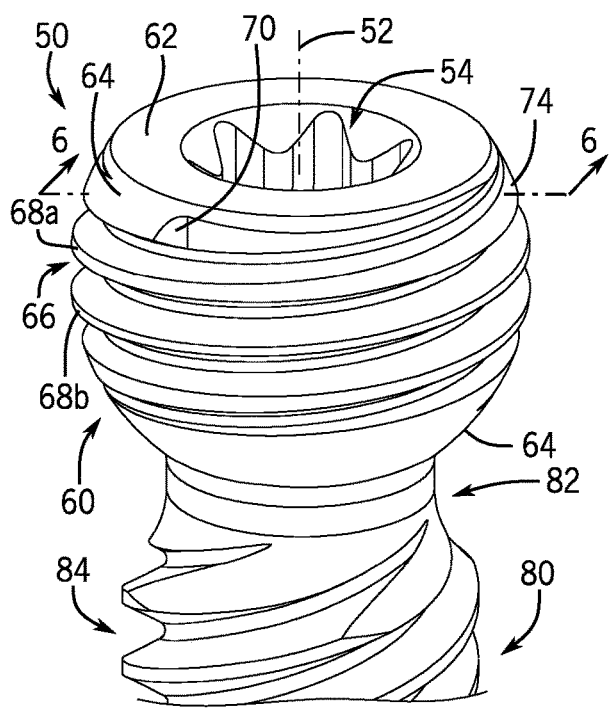
FIG. 5 is a perspective view of the threaded universal shank head shown in FIG. 3.
Figure 6:
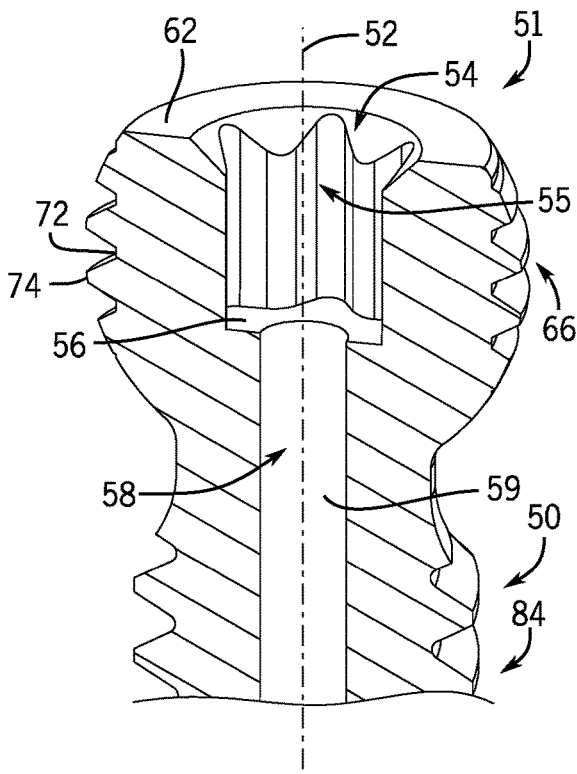
FIG. 6 is a cross-sectional perspective view of the shank head of FIG. 5.

With reference to FIGS. 5-6, the neck 82 of the shank 50 can be considered a part of the shank body 80 that is generally non-threaded and that separates or spaces the shank head 60 from the anchor portion 84. In one aspect the neck 82 can also be defined as a narrowing section having a diameter less than that of the adjacent shank head 60 and anchor portion 84 that can provide for increased clearance between the body 80 of the shank 50 and the bottom opening of the receiver. As known to one of skill in the art, the increased clearance can provide for an increased range of angulation between the shank and the receiver upon their assembly together.

Figure 7:
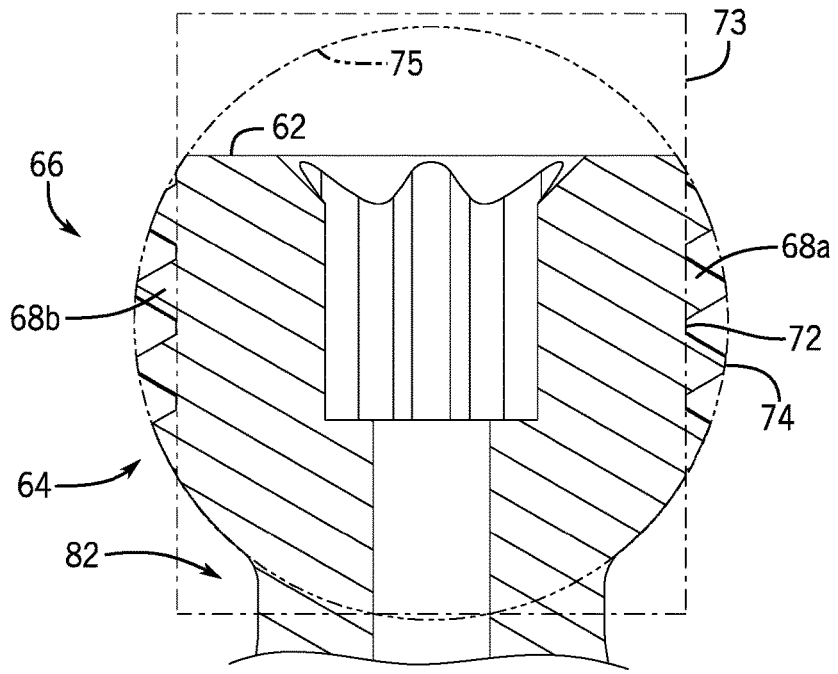
FIG. 7 is a cross-sectional front view of the shank head of FIG. 5 with a virtual cylinder and a virtual sphere superimposed thereon.

With continued reference to FIGS. 5-7, the shank head 60 may have a rounded outer side surface extending from the neck 82 to the top surface 62 at the proximal end 51, at least a portion of which can be further defined as partial spherical outer surface 64. As noted above, in one aspect the top surface 62 may be an annular planar surface that surrounds an internal drive feature 54 or drive socket. For example, the internal drive feature 54 of the bone anchor illustrated in the figures is an aperture formed in the top surface 62, and in one aspect may be a multi-lobular or star-shaped aperture, such as those sold under the trademark TORX, or the like, having internal faces 55 designed to receive a multi-lobular or star-shaped tool for rotating and driving the shank body 80 into the vertebra. It is foreseen that such an internal drive feature may take a variety of tool-engaging forms and may include one or more apertures of various shapes, such as a pair of spaced apart apertures or a hex shape designed to receive a hex tool (not shown) of an Allen wrench type. A seat or base surface 56 of the internal drive feature 54 can be disposed perpendicular to the shank longitudinal axis 52, with the internal drive feature 54 otherwise being coaxial with the shank longitudinal axis 52. In operation, a driving tool is received in the internal drive feature 54, being seated at the base surface 56 and engaging the internal faces 55 of the internal drive feature 54 for both driving and rotating the anchor portion 84 of the shank body 80 into the vertebra, either before or after the shank 50 is attached or coupled to the multiplanar receiver sub-assembly 11. If attached, the threaded anchor portion 84 of the shank body 80 can be driven into the vertebra with the driving tool extending into and through the receiver 100.

Figure 8:
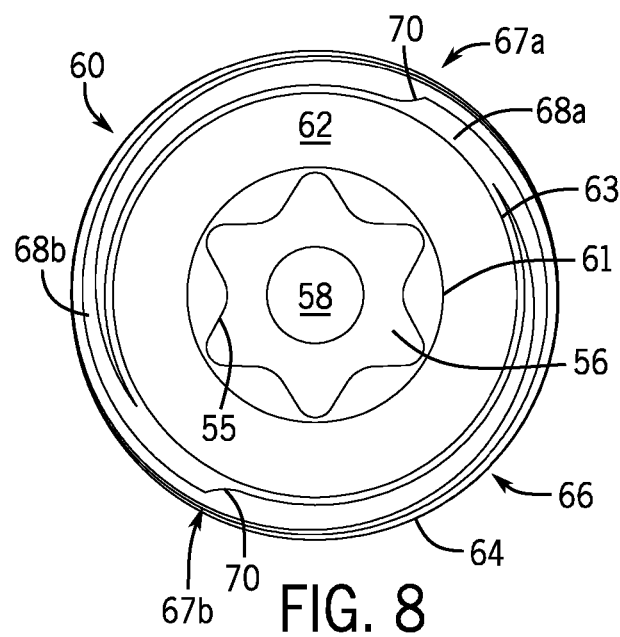
FIG. 8 is a top view of the shank head of FIG. 5 showing a pair of upper starts.

Also shown in the drawings, in some embodiments the shank 50 can be cannulated with an axial bore 58 extending through the entire length thereof and centered about the longitudinal axis 52 of the shank 50. The axial bore 58 can be defined by an inner cylindrical wall 59 of the shank 50 having a circular opening at the distal tip 98 (FIG. 4) and an upper opening communicating, in one aspect, with the internal aperture of the drive socket 54 at the base surface 56 (FIGS. 6-8). The axial bore 58 is generally coaxial with the shank body 80 and the shank head 60, and can provide a passage through the shank 50 interior for a length of wire (not shown) to provide a guide for insertion of the shank body 80 into the vertebra. The axial bore 58 of the cannulated shank 50 can also provide for a pin to extend therethrough and beyond the shank tip 98, the pin being associated with a tool to facilitate insertion of the anchor portion 84 of the shank body 80 into the vertebra.

With continued reference to FIGS. 5-7, the threaded universal shank head 60 of the present disclosure generally includes a plurality of thread forms formed into the rounded or partial spherical outer surface 64 and extending from near the top surface 62 radially and axially toward the neck 82. For example, the shank head 60 can have an upper thread form 66 having helically wound first and second upper threads 68a, 68b resulting in a dual thread/dual lead-in configuration. It will be appreciated that each of the first and second upper threads 68a, 68b will comprise multiple surfaces including an outwardly-facing root surface 72 helically disposed parallel to the shank longitudinal axis 52 and having a cylindrical contour 73 with a constant radius with respect to the shank longitudinal axis 52. Radially farther outward to the outwardly-facing root surface 72 is an outwardly-facing crest surface 74 helically disposed with respect to the shank longitudinal axis 52 having a spherical contour 75 with a constant radius with respect to a center point of the spherical contour located on the shank longitudinal axis 58, and with the sum of the crest surfaces 74 of the first and second upper threads 68a, 68b together defining a discontinuous central portion of the partial spherical outer surface 64.

In other words, the upper thread form 66 can define the spherical shape of the partial spherical outer surface 64 at the crest surfaces 74 thereof, but may be otherwise described as a substantially buttress thread form, sized and shaped to mate with a cooperating lower thread form 156, also having helically wound first and second lower threads 114a, 114b, formed into a partial spherical lower seating surface 110 of the receiver 100 disposed adjacent to a bottom opening 104 at the base portion 106 of the receiver 100 (see FIGS. 13-14). Preferably, the upper thread form 66 of the threaded universal shank head 60 can be relatively thick and heavy to give strength to the thread and prevent the thread from being easily bent or deformed when axial pressure is applied to the shank 50 to maintain the shank head 60 in the receiver 100. In one aspect the upper thread form 66 can wind about the threaded universal shank head 60 in a generally helical pattern or configuration that is typical of threads and can have various pitches, be clockwise or counterclockwise advanced, or vary in most of the ways that conventional buttress or square threads vary. Although the upper thread form 66 of the shank head 60 is shown and described herein as comprising two threads, it is foreseen that in other embodiments not shown, the helically wound upper thread form 66 may have one, three, four, or more threads.

Illustrated in FIG. 7 is a cross-sectional side view of the threaded universal shank head 60 on which a virtual cylinder defined by the cylindrical contour 73 and a virtual sphere defined by the spherical contour 75 are superimposed. The radius of the spherical contour 75 can be greater than the radius of the cylindrical contour 73 such that the intersections of these contours define the beginning and ending of each thread 68a, 68b at respective upper and lower axial positions on the shank head 60. For instance, the axial upper position can be a circle on the shank head 60 represented by the upper intersection of the virtual cylinder 73 and the virtual sphere 75, whereas the axial lower position is a circle on the shank head 60 represented by the lower intersection of the virtual cylinder 73 and the virtual sphere 75. Together, the plurality of outwardly-facing crest surfaces 74 can form a discontinuous central portion of the partial spherical outer surface 64 of the shank head 60.

Figure 10:
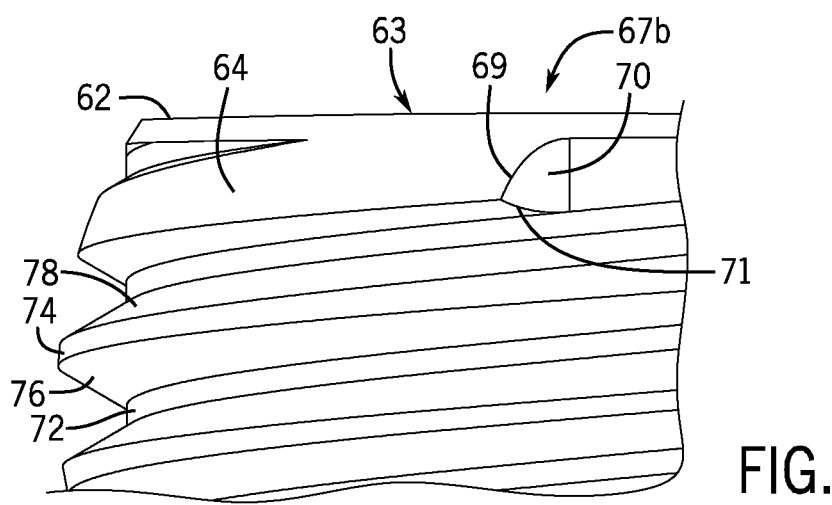
FIG. 10 is a close-up side view of the shank head of FIG. 5 showing a start structure and the upper thread form of the shank head.

With reference to FIG. 10, the axial width of the outwardly-facing crest surfaces 74 at any particular location may be defined by edges formed by the intersection of a load-flank surface 76 and a clearance-flank surface 78. The load-flank surface 76 is generally located on a lower or distal side of the outwardly-facing crest surface 74, between the outwardly-facing root surface 72 and crest surface 74, and also faces downward toward the shank body 80 at a load-flank angle with respect to the outwardly-facing root surface 72. The clearance-flank surface 78 is generally located on an upper or proximal side of the outwardly-facing crest surface 74 that is opposite the load-flank surface 76, and also faces upward toward the top surface 62 of the shank head 60 at a clearance-flank angle with respect to the outwardly-facing root surface 72. The load-flank and clearance-flank surfaces 76, 78 may be flat, or in other embodiments not shown they may be curvate or curvilinear.

Figure 9:
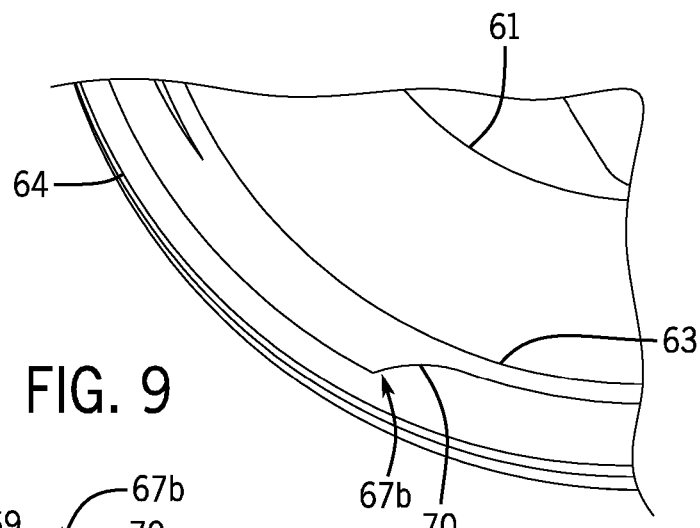
FIG. 9 is a close-up top view of the shank head of FIG. 5 showing a start structure of the upper thread form of the shank head.

As shown in FIGS. 8-10, each of the helically wound first and second upper threads 68a, 68b of the upper thread form 66 may have a respective upper start structure 67a, 67b located at or near the annular planar top surface 62 of the shank head 60, which top surface 62 can be further defined as having a circular inner edge 61 and a circular outer edge 63. The upper starts 67a, 67b may have a geometry that facilitates alignment of the first and second upper threads 68a, 68b with corresponding threads located in the bottom opening 104 and internal cavity 108 of the receiver 100, as described below. In particular, each of the upper starts 67a, 67b may have a leading face 70 having at least one radius of curvature. In one aspect the leading face 70 can comprise a concave surface extending parallel to the shank longitudinal axis 52, and which tangentially merges with the cylindrical contour or the outwardly-facing root surface 72 from the adjacent thread. The leading face 70 can also share a first upper edge 69 with the outwardly-facing crest surface 74 and a second lower edge 71 with the load-flank surface 76. In one aspect the first and second edges 69, 71 can also abruptly meet at a point. As shown in the drawings, the first and second edges 69, 71 and the leading face 70 can also be spaced a short distance below the circular outer edge 63 of the annular planar top surface 62.

In other embodiments not shown, the leading face 70 may comprise the concave surface described above together with a convex surface, such that the first and second edges 69, 71 tangentially merge together. Moreover, the leading face 70 may not be entirely parallel with the shank longitudinal axis 52, such that the leading face 70 may face upwardly toward the proximal end 51 or downwardly toward the distal end 99 of the shank 50, such that the leading face 70 can form at least a portion of a beveled surface.

With reference to FIG. 8, the upper starts 67a, 67b may be equal-angularly spaced apart about the circumference of the shank head 60. Or in other words, the starts may be spaced apart by 360 degrees divided by the number of starts such as, for example, the two starts 67a, 67b being spaced apart by 180 degrees. However, it is foreseen that the upper starts may also be unequal-angularly spaced apart, such as to define a definitive or 'keyed' starting orientation between the two threadably-engageable components. For example, such an embodiment (not shown) may have two upper starts spaced apart by more than or less than 180 degrees from each other, such as 190 degrees/170 degrees.

To provide a biologically active interface with the bone, the shank body 80 may be coated, perforated, made porous, or otherwise treated. The treatment may include, but is not limited to a plasma spray coating or other type of coating of a metal or, for example, a calcium phosphate; or a roughening, perforation, or indentation in the shank surface, such as by sputtering, sand blasting, or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate (Ca3 (PO4)2, tetra-calcium phosphate (Ca4P2O9), amorphous calcium phosphate, and hydroxyapatite (Ca10(PO9)6(OH)2). Coating with hydroxyapatite, for example, is desirable as hydroxyapatite is chemically similar to bone with respect to mineral content and has been identified as being bioactive and thus not only supportive of bone ingrowth, but actively taking part in bone bonding.

Illustrated in FIGS. 11-14 is the receiver 100 of the multiplanar bone anchor assembly 12 having a generally U-shaped appearance with a partially discontinuous substantially cylindrical inner profile and a partially-cylindrical and partially-faceted outer profile, although other profiles are contemplated. The receiver 100 has a vertical centerline axis 101, or axis of rotation, that is shown in FIG. 2 as being alignable with the longitudinal axis 52 of the shank 50 during the threaded assembly of the receiver 100 with the shank 50. After the receiver 100 is pivotally attached to the shank head 60, either before or after the shank 50 is implanted in a vertebra, the vertical centerline axis 101 of the receiver is typically disposed at an angle with respect to the longitudinal axis 52 of the shank as shown, for example, in FIGS. 42-44.

The multiplanar receiver 100 generally comprises a base portion 106 defining an internal cavity 108 or lower portion of a generally cylindrical central bore 120 that is centered around the receiver's vertical centerline axis 101, and which communicates with a bottom surface 102 of the receiver 100 through a bottom opening 104 at the distal end 103. As shown, a pair of upright arms 130 can extend upwardly from the base 106 to form the upper portion of the receiver and to define an upwardly-open rod channel 136 configured for receiving the elongate rod, and which rod channel 136 opens laterally onto a front face 140 and a back face 141 of the receiver 100, respectively. Furthermore, each of the upright arms 130 has an interior face 131 that can include a discontinuous upper portion of the central bore 120 that extends upward from the bottom opening 104 through the cavity 108 and the rod channel 136 to top surfaces 138 of the upright arms 130 at the proximal end 139 of the receiver 100. While the different portions of the receiver 100 described above are generally formed together as one integral piece, it is foreseen that in other aspects the different portions can be formed as separate pieces that are subsequently assembled together to form the multiplanar receiver.

The interior faces 131 of the upright arms 130 can include opposed parallel planar surfaces 132 on either side of the upper discontinuous portion of the central bore 120 that serve to define the width of the rod channel 136. In addition, lower portions of the opposed planar surfaces 132 can curve downwardly and inwardly to form U-shaped saddle surfaces 134 adjacent the front and back faces 140, 141 that define the lower extent of the channel 136. In one aspect the saddle surfaces 134 can be U-shaped so as to accommodated an elongate rod 4 (see FIG. 2) having a rounded cross-section, although other shapes for the saddle surfaces 134 and the elongate rod are possible and considered to fall within the scope of the present disclosure. In addition, a pair of front/back tool engagement cutouts or recesses 144 may also be formed into the front face 140 and back face 141 of the upright arms 130, respectively, that interrupt the U-shaped saddles 134 into upper portions that curve inwardly from the opposed parallel planar surfaces 132 and a lower saddle portion that defines the bottom-most portion of the U-shaped saddle 134. As shown in the drawings, each side of the front/back tool engagement recesses 144 can extend into the front face 140 or the back face 141 of the upright arms 130 at an angle so as to form an inwardly-extending triangularly-shaped recess.

The interior faces 131 of the upright arms 130 can further include a discontinuous guide and advancement structure 135 formed into the upper discontinuous portion of the cylindrical central bore 120 adjacent the top surfaces 138 of the upright arms 130. The guide and advancement structure 135 is shown as a discontinuous dual thread interlocking flangeform having first and second receiver threads configured to mate under rotation with a closure having a continuous dual thread/dual lead-in guide and advancement structure, such as a similar structure on the closure 190 (see FIGS. 22-25) and as described more fully below. In one aspect, the discontinuous guide and advancement structure 135 can comprise helically wound flanges with splay-resisting or splay-controlling flange profiles for operably guiding and advancing the closure 190 downward under rotation between the arms 130 and having such a nature so as to resist, inhibit, limit, or preferentially control the splaying of the arms 130 (so as to allow a specific amount of splay) while the closure 190 is advanced into the rod channel 136, as well as during the eventual abutting, for example, and continued torquing of the closure 190 against the elongate rod to lock the multiplanar bone anchor assembly 12. In other aspects, it is foreseen that the discontinuous helically wound guide and advancement structure 135 may take on a variety of alternative forms, including but not limited to a square-shaped thread, a buttress thread, a modified buttress thread, a reverse angle thread or other thread-like or non-thread-like guide and advancement structures (such as a twist-in-place mechanism).

In configurations or embodiments where the rod channel 136 of the receiver 100 is an open channel, the receiver 100 can further include breakoff extensions or tabs (not shown) that can be integrally formed with the upright arms 130, and which extend upwardly from the top surfaces 138 of the upright arms 130 so as to provide additional structure for extending the partial helically wound guide and advancement structure 135 continuously upwards for the outer threads of the closure 190 (FIGS. 22-25) to follow. In one aspect the breakoff extensions can allow for the elongate rod to be captured at a greater distance from the anchored receiver 100 and for urging the elongate rod toward the open channel 136 of the receiver 100 during a reduction procedure. As known in the art, the breakoff extensions or tabs can be connected to the upper portions of the upright arms 130 with weakened break regions that provide for the extensions to be broken off and removed from the upright arms 130 to provide the desired low-profile bone anchor assembly or implant after the assembly is complete.

Although shown in the drawings with fully separate upright arms 130 that define an open channel 136, it is foreseen that the upper portion of the receiver in other embodiments of the bone anchor assembly can include upright arms that are connected together at their upper ends so as to form a closed top receiver, with the rod channel becoming a rod aperture, and in which the elongate rod is introduced into the receiver from the side rather than from the top. With the upright arms being connected at their upper ends, moreover, the guide and advancement structure located adjacent the top surface of the receiver and configured to mate under rotation with the closure can be continuous rather than discontinuous, and which structure can substantially eliminate splay between inner surfaces of the upright arms forming the rod aperture. This feature may be especially useful when implanting a long series of pivotal bone anchor assemblies along a patient's spine, and it is determined that it would be beneficial to use a closed top receiver at one end to better secure the elongate rod at the beginning of the series.

With reference to FIGS. 13-14, the upper discontinuous portion of the central bore 120 immediately below the guide and advancement structure 135 and between the opposed parallel planar surfaces 132 can be defined by an inwardly-facing discontinuous upper cylindrical surface 128 that extends downward from the guide and advancement structure 135 toward a downwardly-facing discontinuous annular step surface 127. The discontinuous annular step surface 127 can demark the bottom of the discontinuous upper cylindrical surface 128 and the top of the internal cavity 108.

The internal cavity 108 itself may include an upper chamber 124, a middle chamber 122, and a lower seating surface 110. The upper chamber 124 is generally defined by an inwardly-facing discontinuous lower cylindrical surface 126 that extends downwardly below the discontinuous annular step surface 127 to a discontinuous retaining ridge 125, together with a pair of opposed vertically-aligned clearance recesses 129 that are formed into the interior edges of the lower saddle surfaces 134, and which can bifurcate both the discontinuous lower cylindrical surface 126 and the discontinuous retaining ridge 125. The discontinuous lower cylindrical surface 126 may have a diameter that is greater than the diameter of the upper discontinuous cylindrical surface 128, as well as a smooth finish, so as to permit axial movement of the pressure ring 170 within the upper chamber portion 124 of the internal cavity 108, as described below.

As shown in the figures, the discontinuous retaining ridge 125 generally includes a pair of inwardly-projecting ridge arcs that extend circumferentially between the vertically-aligned clearance recesses 129, and which can serve to axially separate the upper chamber 124 from the middle chamber 122. The retaining ridge 125 may have a curvate cross-section with a convex portion projecting into the central bore and upper and lower concave portions transitioning into the inwardly-facing discontinuous lower cylindrical surface 126 on the upper side and an inwardly-facing partial spherical surface 123 on the lower side, respectively. As discussed in more detail below, the retaining ridge 125 may retain the pressure ring 170 in a pre-assembled shipping state within the receiver 100 prior to assembly with the shank 50 and remaining components of the bone anchor assembly. It is foreseen that the location of the retaining ridge 125 could be adjusted within the receiver assembly and/or be replaced with a groove and snap ring.

The middle chamber 122 is generally defined by the inwardly-facing partial spherical surface 123 up to and beneath the discontinuous retaining ridge 125 and extending downward to a circular transition edge 121 demarking a transition to the lower seating surface 110. The transition edge 121 may lie in a plane substantially perpendicular to the vertical centerline axis 101 of the receiver. As with the discontinuous lower cylindrical surface 128 and the retaining ridge 125, the partial spherical surface 123 may be partially interrupted by the vertically-aligned clearance recesses 129. The partial spherical surface 123 may also have a smooth finish to allow rotation and axial articulation of the pressure ring 170 within the middle chamber 122.

Each of the vertically-aligned clearance recesses 129 generally provides a widening to the upper chamber 124 and an opening to the middle chamber 122, so as to provide for the insertion of the pressure ring 170 into the internal cavity 108. As shown in the figures, the clearance recesses 129 may have a partially elliptical profile, but in other embodiments not shown the clearance recesses 129 may have an oblong, rectangular, or circular opening. Each of the clearance recesses 129 may also have a taper such that it is radially wider with respect to the vertical centerline axis 101 of the receiver at the lower saddle surface 136 and narrower at its intersection and termination with the partial spherical surface 123. In addition, the width of the clearance recesses 129 may be the same as or larger than the axial height of the partial inwardly-facing spherical surface 123, which in turn can be about the same as the axial height of the pressure ring 170, for reasons discussed in more detail below.

Figure 16:
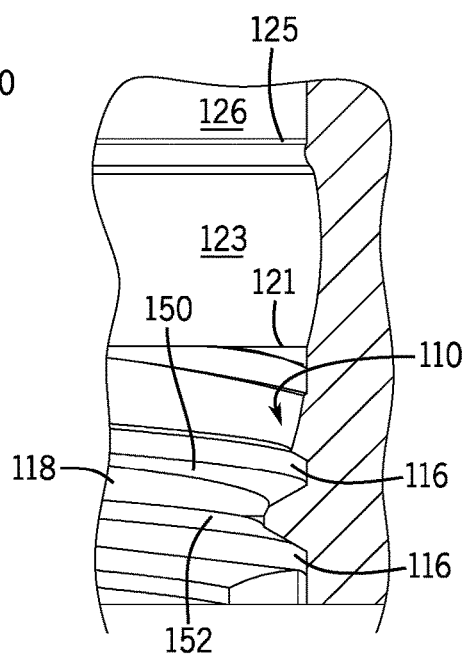
FIG. 16 is a close-up of the cross-sectional front view of FIG. 15 showing a start structure and the lower thread form of the internal cavity.

The lower seating surface 110 is configured to receive and support the threaded universal head 60 of the shank 50 within a lower portion of the internal cavity 108 of the receiver 100, and generally comprises a discontinuous partial spherical surface curving downward and inward from the transition edge 121 to the bottom opening 104 that opens onto the bottom surface 102 of the receiver 100, and having a lower thread form 112 formed therein. In particular, the lower thread form 112 is configured to engage the dual thread/dual lead-in upper thread form 66 of the shank head 60 upon insertion and rotation thereof and can therefore include helically wound first and second lower threads 114*a*, 114*b* having respective first and second lower starts 113*a*, 113*b* (see FIG. 18). With reference to FIG. 16, each of the first and second lower threads 114*a*, 114*b* may also comprise multiple surfaces including an inwardly-facing root surface 116 helically disposed parallel to the vertical centerline axis 101 of the receiver and having a cylindrical contour 117 with a constant radius with respect to the vertical centerline axis 101 of the receiver. Radially closer to the inwardly-facing root surface 116 is an inwardly-facing crest surface 118 helically disposed with respect to the vertical centerline axis 101 of the receiver having a spherical contour 119 with a constant radius with respect to a virtual center point of the partial spherical contour located on the vertical centerline axis 101, and with the sum of the crest surfaces 18 of the first and second lower threads 114*a*, 114*b* together defining the discontinuous lower seating surface 110.

Figure 15:
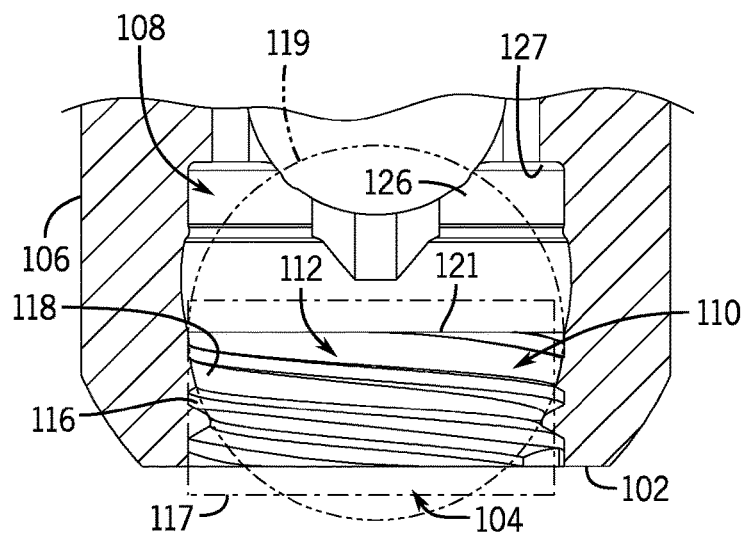
FIG. 15 is a cross-sectional front view of the internal cavity of the multiplanar receiver of FIG. 11 with a virtual cylinder and a virtual sphere superimposed thereon.

Illustrated in FIG. 15 is a cross-sectional side view of the receiver 100 on which a virtual cylinder defined by the cylindrical contour 117 of the root surfaces 164 and a virtual sphere 170 defined by the spherical contour 119 of the crest surfaces 118 are superimposed. In one aspect the radius of the spherical contour 119 can be substantially the same as the radius of the cylindrical contour 117, with the two contours coinciding at the transition edge 121 that defines the upper edge of the discontinuous lower seating surface 110.

With reference back to FIG. 16, the axial width of the inwardly-facing crest surface 118 may be defined by edges formed by the intersection of a load-flank surface 150 and a clearance-flank surface 152. For example, the load-flank surface 150 can be located on an upper or proximal side of the crest surface 118 between the inwardly-facing root and crest surfaces 116, 118, and faces upward toward the rod channel 136 at a complementary angle substantially the same as the load-flank angle of upper thread form 66 of the shank head 60 (see FIG. 10). In corresponding fashion, the clearance-flank surface 152 can be located on a lower or distal side of the inwardly-facing crest surface 118 between the inwardly-facing root and crest surfaces 116, 118 opposite the load-flank surface 150 and faces downward toward the bottom opening 104 at a complementary angle that is substantially the same as the clearance-flank angle of upper thread form 66 of the shank head 60. In some embodiments the load- and clearance-flank surfaces 150, 152 may be flat, while in other embodiments (not shown) they may be curvate or curvilinear.

Figure 17:
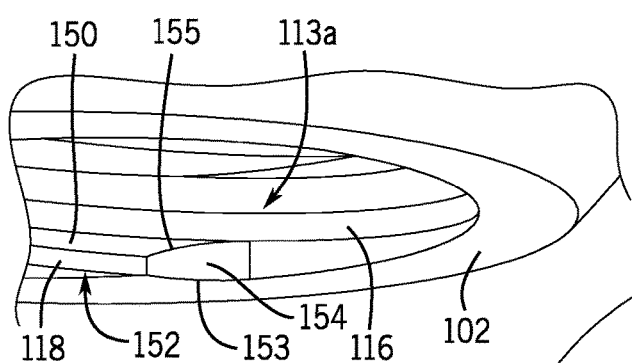
FIG. 17 is a close-up lower perspective view of the bottom of the multiplanar receiver of FIG. 11 showing a start structure of the lower thread form in the bottom opening.
Figure 18:
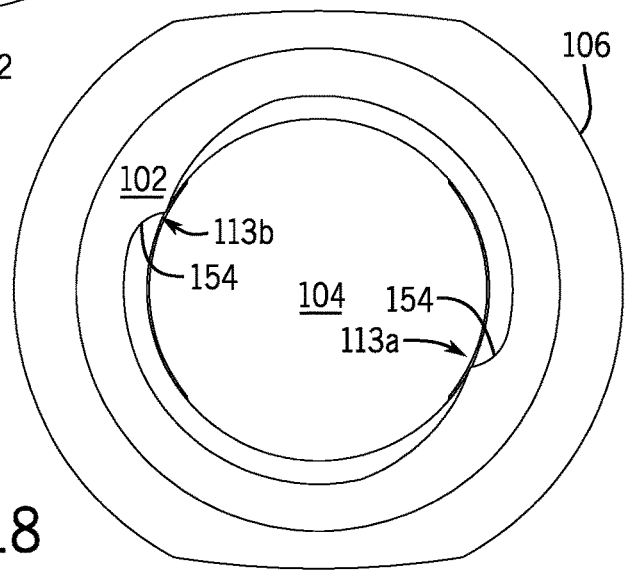
FIG. 18 is a bottom view of the multiplanar receiver of FIG. 11 showing a pair of lower starts.

As shown in FIGS. 17-18, each of the helically wound first and second lower threads 114a, 114b of the lower thread form 112 may have a respective lower start 113a, 113b located at or near the bottom opening 104 of the receiver 100. The lower starts 113a, 113b may have a geometry that facilitates alignment of the first and second lower threads 114a, 114b with corresponding threads of the shank head 60 (see FIG. 10). Each of the lower starts 113a, 113b may have a leading face 154 having at least one radius of curvature. In one aspect, the leading face 154 can have a concave surface extending parallel to the vertical centerline axis 101 of the receiver and tangentially merging with the cylindrical contour or the inwardly-facing root surface 116 from the adjacent thread. The leading face 154 can share a first edge 153 with the clearance-flank surface 152 and a second edge 155 with the load-flank surface 150, and the first and second edges 153, 155 can abruptly meet at an edge of the inwardly-facing crest surface 118. In other embodiments not shown, the leading face 154 may have both a concave surface as described above and a convex surface such that the first and second edges 153, 155 tangentially merge with edges of the inwardly-facing crest surface 118. Moreover, in other embodiments, the leading face 154 may not necessarily be parallel with the vertical centerline axis 101 of the receiver, such that the leading face 154 may face upwardly toward the rod channel 136 or downwardly toward the bottom opening 104 of the receiver 100. In addition, in one aspect the first edge 153 of the leading face 154 can be on the same plane as the bottom surface 103 of the receiver 100, wherein the bottom surface 103 can be formed perpendicular to the vertical centerline axis 101 of the receiver 100.

The lower starts 113a, 113b of the lower thread form 112 may be equal-angularly spaced apart about the circumference of the bottom opening 104 or in other words, the lower starts 113a, 113b may be spaced apart by 360 degrees divided by the number of starts. For example, as shown in FIG. 18, the first and second lower starts 113a, 113b are spaced apart by 180 degrees. In other embodiments not shown, however, the lower starts may be unequal-angularly spaced apart. For instance, an embodiment may have two lower starts spaced apart by more than or less than 180 degrees from each other, such as 190 degrees/170 degrees, and can correspond with the angular spacing between the upper starts formed on the head of the shank (as described above), so that the pairs of upper and lower starts still engage simultaneously. Alternatively, the upper starts on the shank head and the lower starts on the receiver may not correspond exactly with each other, so that one upper start on the shank head can engage with a lower start on the receiver prior to the engagement between the other upper and lower start structures.

With reference back to FIG. 11, the outer surface of the receiver 100 can have a partially-cylindrical and partially-faceted outer profile. For example, the outer surface may include an outwardly-facing partial cylindrical surface 142 that is concentric with and oppositely facing with respect to the upper and lower discontinuous cylindrical surfaces 126, 128 formed into the internal cavity 108 and the inner surfaces of the upright arms 130. The outer surface of the receiver 100 can further include faceted or planar portions that may or may not be parallel with the vertical centerline axis of the receiver. For example, in one aspect of the present disclosure the outer surface can include outer lower side planar faces 146 located on the base portion 106 of the receiver below the rod channel 136, and which extend upward and inward at an angle to the vertical centerline axis to intersect the lower saddle surfaces 134 and the front/back tool engagement recesses 144 described above. As can be seen, the front/back tool engagement recesses 144 include recessed planar surfaces 145 that extend in a direction parallel to the vertical centerline axis 101 of the receiver but at an acute angle with respect to the transverse axis of the rod channel 136. In addition, front/back upper planar faces 147 on opposite sides of the rod channel 136 can extend upward along the front and back edges of the upright arms 130 from the front/back tool engagement recesses 144 to the top surfaces 138 of the upright arms 130.

Each of the outer partial cylindrical surfaces 142 that define the outer surfaces of the upright arms 130 may also include a side or lateral tool engagement recess 148. The pair of lateral tool engagement recesses 148 can have recessed planar surfaces 149 that extend parallel to each other, to the vertical centerline axis 101 of the receiver, and also to the transverse axis of the rod channel 136. In one aspect recessed planar surfaces 149 and recessed planar surfaces 145 can serve together as tool engagement outer surfaces that allow for tooling to securely engage and hold the receiver 100 during an initial pre-assembly with the pressure ring 170 into the receiver 100 to form the multiplanar receiver sub-assembly 11, as well as during coupling of the multiplanar receiver sub-assembly 11 to the threaded head 60 of the shank 50 after or before the implantation of the body 80 of the shank 50 into a vertebra, and during further assembly of the multiplanar receiver sub-assembly 11 with the elongate rod 4 and the closure 190.

It will be appreciated by one of skill in the art that other shapes and configurations for the interior and exterior surfaces of the receiver 100 that are different from those shown in the drawings while providing for similar interaction and functionality of the various components of the bone anchor assembly, are also possible and considered to fall within the scope of the present disclosure. For example, in one aspect the front/back tool engagement recesses 144 and the lateral tool engagement recesses 148 may be replaced by horizontally-extending "top notch" type tool receiving grooves formed around the upper periphery of the upright arms 130. In other aspects additional planar faces can be formed into the outer partial cylindrical surfaces 142 of the receiver 100 (which may or may not be orthogonal to the lateral tool engagement recesses 148) or elsewhere on the outer surface of the receiver. Moreover, additional tool engagement structures or recesses formed on the outer faces of the breakoff extensions described above are also possible.

Figure 19:
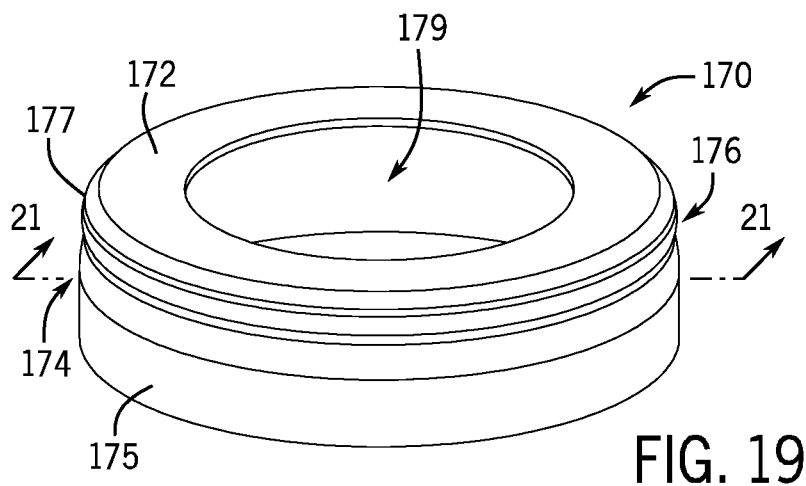
FIG. 19 is an upper perspective view of the multiplanar insert or pressure ring shown in FIG. 2.
Figure 20:
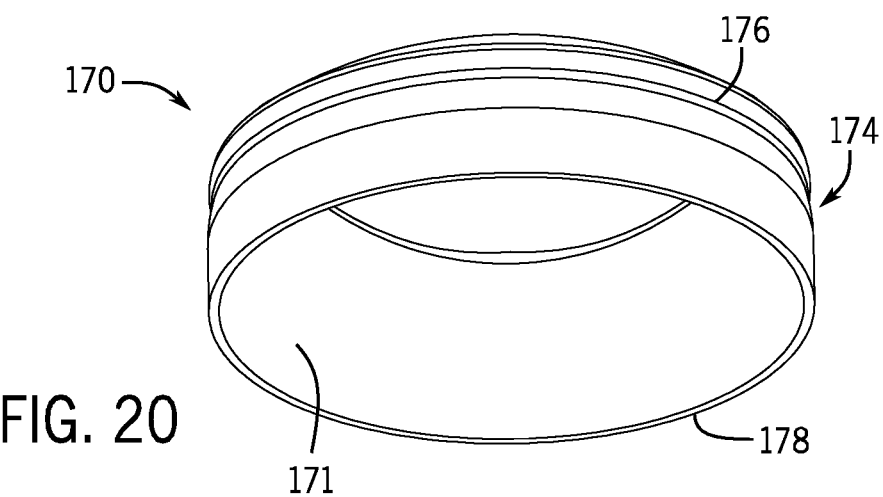
FIG. 20 is a lower perspective view of the multiplanar pressure ring of FIG. 19.
Figure 21:
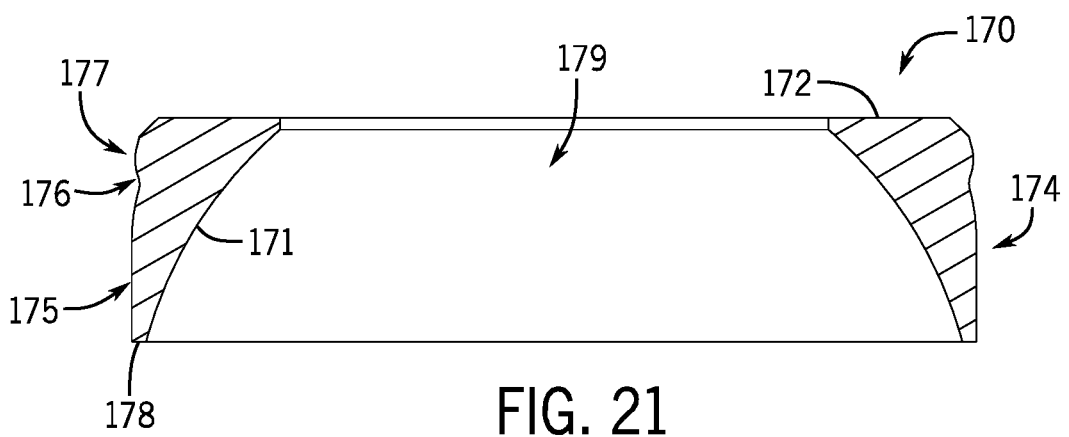
FIG. 21 is a cross-sectional side view of the multiplanar pressure ring of FIG. 19.
Figure 22:
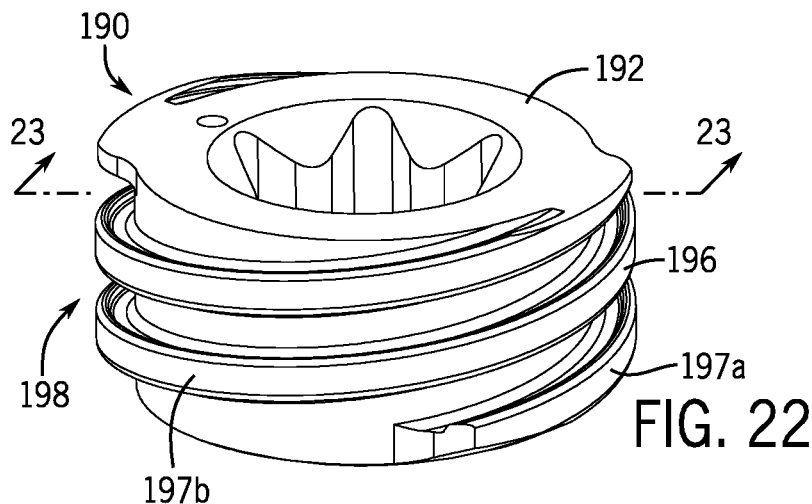
FIG. 22 is a perspective view of the closure shown in FIG. 2.
Figure 23:
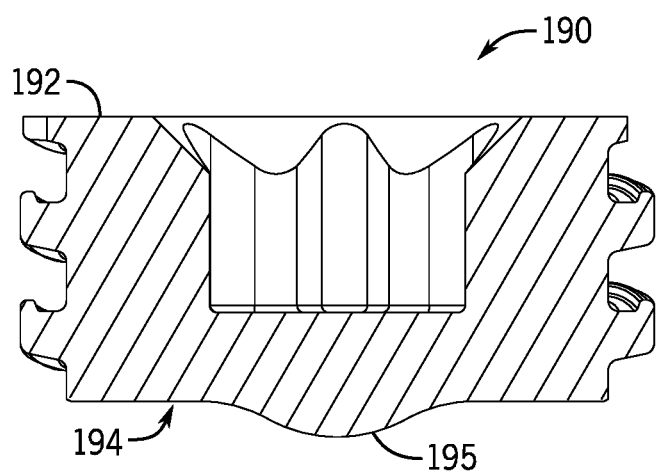
FIG. 23 is a cross-sectional side view of the closure of FIG. 22.
Figure 24:
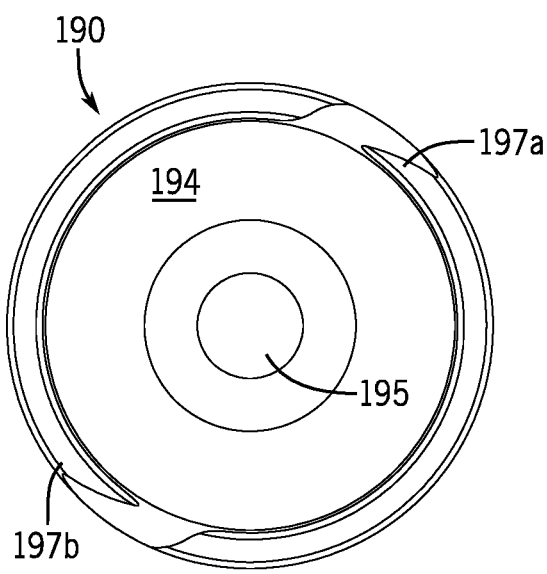
FIG. 24 is a bottom view of the closure of FIG. 22.
Figure 25:
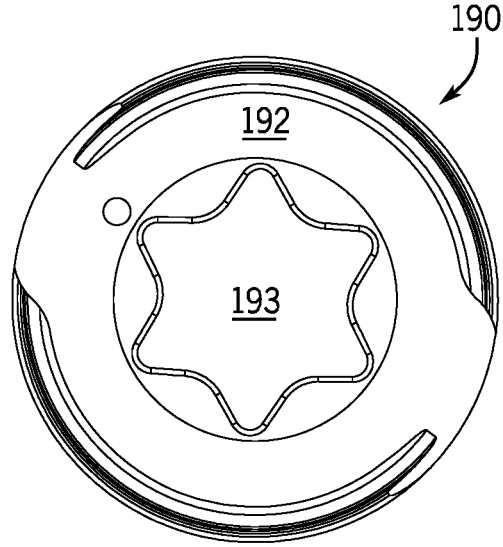
FIG. 25 is a top view of the closure of FIG. 22.

Illustrated in FIGS. 19-21 is the multiplanar insert or pressure ring 170 that is operable to transfer the locking force or pressure created by the closure downwardly through the elongate rod 4 and the pressure ring 170 to the partial spherical outer surface 64 of the shank head 60 defined in part by the outwardly-facing crest surfaces 74 of the upper thread 66. The pressure ring 170 can have a ring shaped body with a top surface 172, a bottom edge surface 178, and a side or lateral outer surface 174 having a generally cylindrical profile in cross-section that can be sized and shaped for slidable interference engagement with the inwardly-facing discontinuous lower cylindrical surface 128 of the internal cavity 108. In particular, the lateral outer surface 174 may have a lower cylindrical portion 175 and an upper cylindrical or toroidal portion 177 separated by a circumferential recess 176 that is sized and shaped to receive the discontinuous retaining ridge 125 projecting inward from the sidewall surfaces of the internal cavity 108, as described above. In addition, the upper cylindrical or toroidal portion 177 may connect to the annular top surface 172 via a chamfer that can provide additional clearance during insertion and rotation of the pressure ring 170 within the internal cavity 108.

As shown in the drawings, the pressure ring 170 can further include a downwardly-opening partial spherical lower surface 171 that, as noted above, is configured to engage with an upper portion of the partial spherical outer surface 64 of the shank head 60 defined in part by the outwardly-facing crest surfaces 74 of the upper thread form 66. In one aspect the partial spherical lower surface 171 can be textured, ridged, coated, and the like, to improve the frictional engagement with the crest surfaces 74 of the upper thread form 66.

In addition, the annular top surface 172 of the pressure ring 170 is generally configured to engage the bottom or lowermost or underside surface of the elongate rod 4 when the elongate rod is positioned within the rod channel 136 of the receiver. As shown in the drawings, in one aspect the top surface 172 can be a substantially-planar annular surface with a flat symmetrical shape that allows for positioning or loading the pressure ring 170 into the receiver 100 in any rotational orientation relative to the vertical centerline axis 101 of the receiver. However, and as described in more detail below, in other aspects the top surface can include one or more curvate surfaces forming an insert channel that is configured to closely receive a lower portion of the elongate rod. A central tool receiving aperture 179 can also be formed through the top surface 172 to allow passage of a driving tool to engage the internal drive feature 54 of the shank head 60. The central tool receiving aperture 179, in one aspect, can be defined by a cylindrical inner surface that is smooth and non-threaded.

Although shown in the drawings as having a continuous solid body for providing a desired stiffness and rigidity, it is foreseen that the pressure ring could alternatively have an open ring body with a slit or slot extending entirely through the thickness of the ring body between the top and the bottom and from the outer surface to the inner surface. This aspect may be advantageous for mitigating the need for the vertical alignment recesses 129 formed into the interior edges of the lower saddle surfaces 134. In yet other embodiments of the bone anchor assembly, the body of the pressure ring could include one or more partial slots or recesses extending into the thickness from any side, whether from the top, the bottom, the inside or the outside, and having any shape and depth. These and other modifications configured to provide the pressure ring with a desired compliance or other structural property are also considered to fall within the scope of the present disclosure. It is also foreseen, moreover, that the bone anchor assembly could be configured without the lower pressure ring, with the functionality of the lower pressure ring being provided by other components of the bone anchor assembly or being done without altogether.

With reference to FIGS. 22-25, in one embodiment the closure 190 can comprise a generally cylindrical closure body having a top surface 192, a bottom surface 194, and an outer continuous guide and advancement structure 196 formed into the outer side surface 198 of the closure body that operably joins with the discontinuous guide and advancement structure 135 formed into the upright arms 130 of the receiver 100. As illustrated, the outer continuous guide and advancement structure 196 can be a dual thread/dual lead-in guide and advancement structure having first and second closure threads 197a, 197b and corresponding first and second closure starts. In other embodiments not shown, the outer continuous guide and advancement structure 196 may have one or more than two threads and corresponding starts. In one aspect, the outer continuous guide and advancement structure 196 can comprise helically wound flanges with splay-resisting or splay-controlling flange profiles for operably guiding under rotation and advancing the closure 190 downward between the upright arms 130 and having such a nature so as to resist, inhibit, limit, or preferentially control the splaying of the upright arms 130 when the closure 190 is advanced into the rod channel 136. In other aspects, the guide and advancement structure 196 may take on a variety of alternative forms, including but not limited to buttress threads, square threads, reverse angle threads, or other thread-like or non-thread-like helically wound advancement structures.

As shown in the drawings, in one aspect the bottom surface 194 of the closure 190 can include a downwardly-projecting central projection 195 for engaging and securing the elongate rod 4, and for controlling the closure torque to thrust ratio. In other embodiments the bottom surface can include an annular projection, a point ring (i.e. an annular ring surrounding a central point or projection), a recessed surface surrounded by a low outer ridge, and the like. In yet other embodiments the bottom surface can be substantially planar across the extent thereof. In yet other embodiments the closure can have a through-and-through central opening.

The top surface 192 of the closure 190 can further include a driving tool engagement structure, such as an internal drive socket 193, which extends downward or inward into the body of the closure 190. The internal drive socket 193 can be used for closure installation or removal. Similar to the internal drive feature 54 formed into the shank head 60, the internal drive socket 193 of the illustrated closure 190 is an aperture formed in the top surface 192, and in one aspect can be a multi-lobular or star-shaped aperture, such as those sold under the trademark TORX, or the like, having internal faces designed to receive a multi-lobular or star-shaped tool for rotating and driving the closure 190. It is foreseen that such a driving tool engagement structure 193 may take a variety of tool-engaging forms and may include one or more apertures of various shapes, such as a pair of spaced apart apertures or a hex shape designed to receive a hex tool (not shown) of an Allen wrench type. The seat or base surface of the internal drive socket 193 is disposed perpendicular to a closure axis, with the internal drive socket 193 otherwise being coaxial with the axis. In yet other embodiments the internal drive socket can extend entirely through the closure.

In another aspect of the present disclosure, a break-off extension (not shown) can be attached the upper end or top surface of the closure, and extend upwardly away therefrom to provide an external tool engagement structure that can be used for rotatably advancing the closure downward between the upright arms 130 of the receiver 100. In one aspect the break-off extension can be designed to allow the extension to break from the closure at a preselected torque, for example, 60 to 140 inch pounds. It is further foreseen that closures having other shapes, configurations, thread forms or non-threaded engagement alternatives, and the like, that are different from those shown in the drawings while providing for similar interaction and functionality of the various components of the bone anchor assembly, are also possible and considered to fall within the scope of the present disclosure.

Illustrated in FIGS. 26-29 are the receiver 100 and the multiplanar insert or pressure ring 170 of the multiplanar bone anchor assembly 12 during their pre-assembly together into a receiver sub-assembly 11. The pre-assembly can generally take place at a manufacturing facility or factory, prior to shipping to a hospital or surgery center and subsequent engagement with the threaded head 60 of the bone anchor or shank 50 in the surgical setting. In one aspect the pre-assembled receiver 100 and multiplanar insert or pressure ring 170 can also be defined as the multiplanar receiver sub-assembly 11 in a shipping state configuration. Nevertheless, it foreseen that in other aspects the pre-assembled shipping state can also include the further assembly of the multiplanar receiver sub-assembly 11 (i.e. the receiver 100 and the pressure ring 170) together with the bone anchor or shank 50 at the factory or manufacturing facility. It will be further appreciated that in yet other embodiments the individual components described above can also shipped separately from the manufacturing facility for pre-assembly into a receiver sub-assembly at the company prior to shipping, or even at the hospital or surgery center prior to implantation in a patient.

Figure 26:
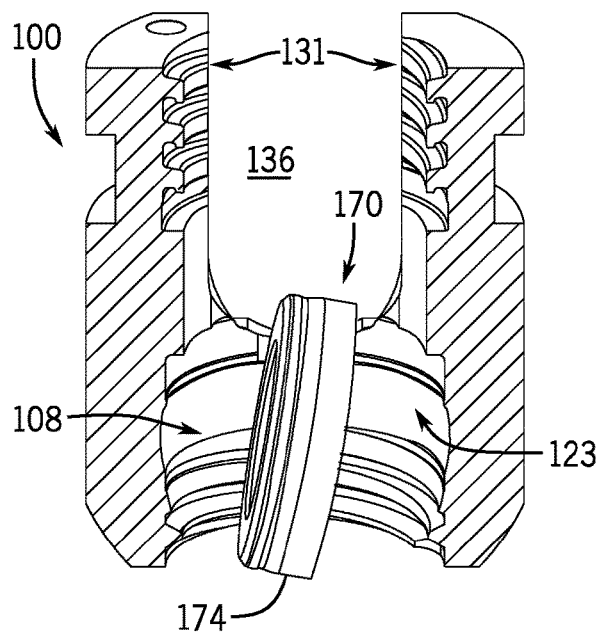
FIG. 26 is a partially cut-away perspective view of the multiplanar receiver and pressure ring of FIG. 2, with the pressure ring being inserted into the axial bore or cavity of the receiver during pre-assembly of the multiplanar receiver sub-assembly.
Figure 27:
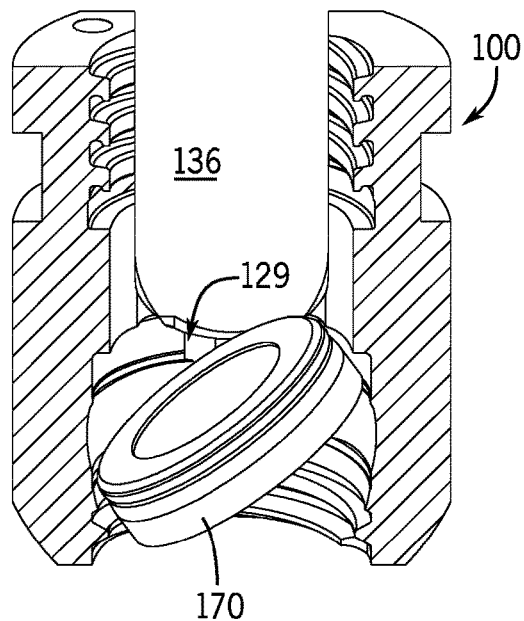
FIG. 27 is a partially cut-away perspective view of the multiplanar receiver and pressure ring of FIG. 26, with the pressure ring being rotated inside the receiver.
Figure 28:
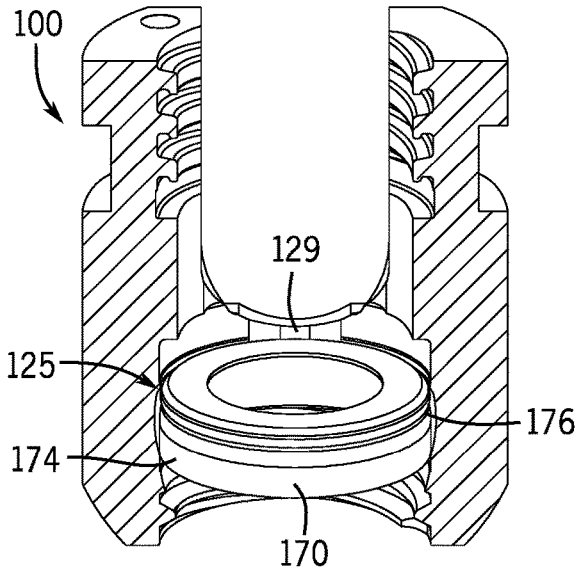
FIG. 28 is a partially cut-away perspective view of the multiplanar receiver and pressure ring of FIG. 26, with the longitudinal axes of the pressure ring and receiver aligned and before the pressure ring is moved upwards into a shipping state position.
Figure 29:
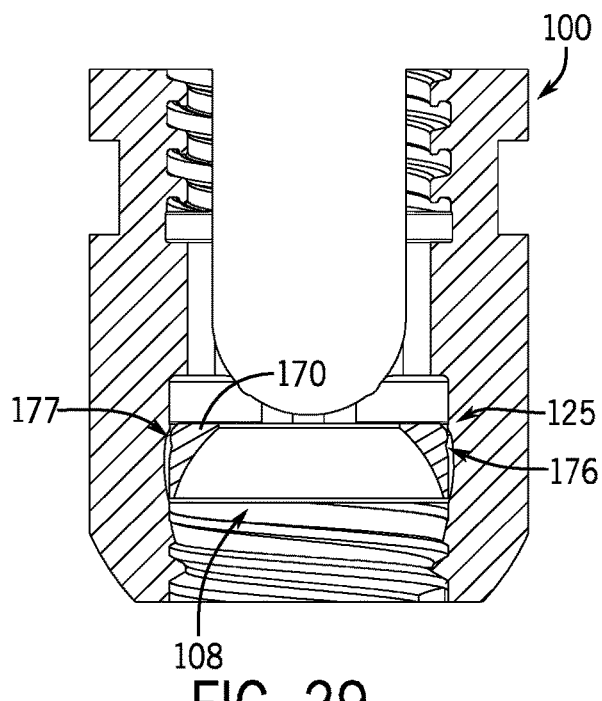
FIG. 29 is a cross-sectional side view of the multiplanar receiver and pressure ring of FIG. 28.

To begin the pre-assembly of the receiver sub-assembly, the pressure ring 170 can first be top-loaded into the receiver 100 as shown in FIG. 26. This can be achieved, for instance, by rotating the pressure ring 170 to a substantially vertical position so that the top and bottom surfaces of the pressure ring 170 face the interior faces 131 of the receiver upright arms 130 and body of the pressure ring 170 aligns with the vertically-aligned clearance recesses 129. The pressure ring 170 can then be downloaded through the open rod channel 136 and into the internal cavity 108 or lower portion of the central bore 120. Once the lateral outer surface 174 of the pressure ring 170 contacts the portions of the inwardly-facing partial spherical surface 123 of the internal cavity 108 that are directly below the clearance recesses 129, the bottom surface of the pressure ring 170 can then be rotated downward, as shown in FIG. 27, until the top and bottom surfaces are in a horizontal position and having outer circular top and bottom edges that are loosely contacting the discontinuous retaining ridge 125 and the circular transition edge 121, respectively, as shown in FIGS. 28-29. It will be appreciated that, in one aspect, the inwardly-facing partial spherical surface 123 that defines the middle chamber 122 of the internal cavity 108 can be sized and shaped to provide clearance for the outer circular top and bottom edges of the lateral outer surface 174 of the pressure ring 170 during the downward rotation to horizontal.

Figure 30:
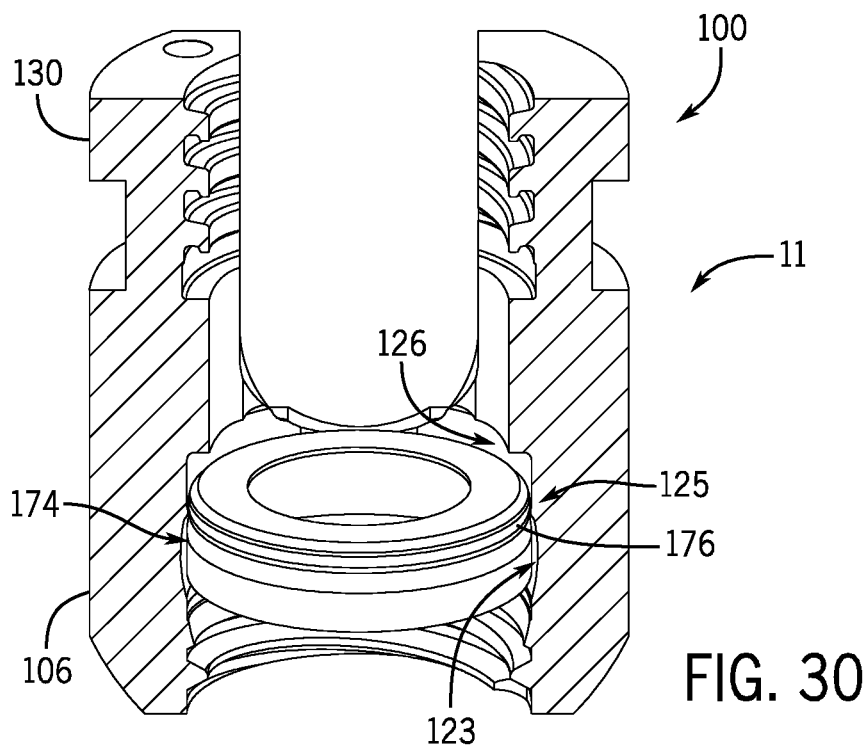
FIG. 30 is a partially cut-away perspective view of the multiplanar receiver and pressure ring of FIG. 28 after the pressure ring has been moved upward into the shipping state position to form the pre-assembled multiplanar receiver sub-assembly.
Figure 31:
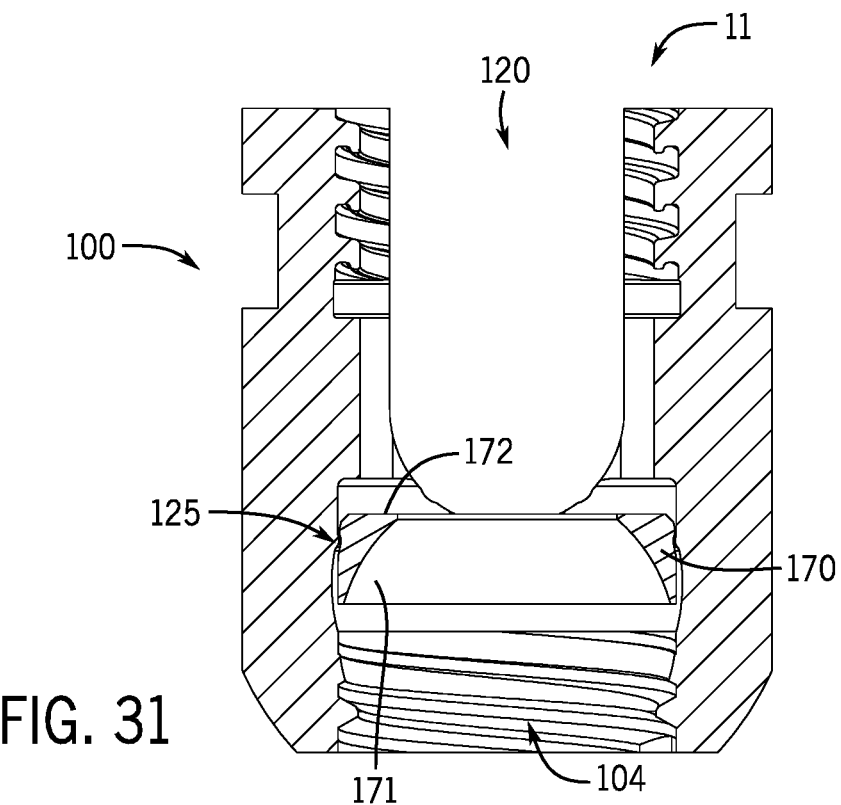
FIG. 31 is a cross-sectional side view of the multiplanar receiver sub-assembly of FIG. 30.
Figure 32:
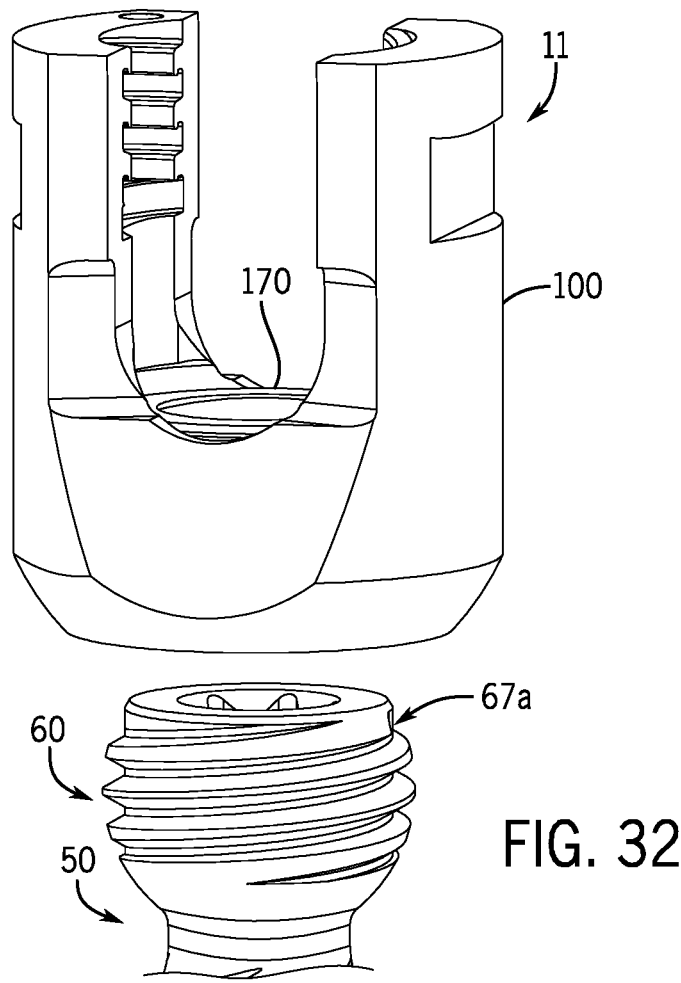
FIG. 32 is a perspective side view of the multiplanar receiver sub-assembly of FIGS. 30-31, prior to the shank head being threadably uploaded through the bottom opening of the receiver.

After reaching the intermediate position shown in FIGS. 28-29, the pressure ring 170 can then be pushed upwards within the internal cavity 108 relative to the receiver 100, so that the upper cylindrical or toroidal portion 177 of the lateral outer surface 174 slides across the retaining ridge 125 with a slight interference fit, until the circumferential recess 176 reaches and snaps onto the retaining ridge 125, as shown in FIGS. 30-31. With the circumferential recess 176 engaging the retaining ridge 125 of the internal cavity 104, the pressure ring 170 is now captured and secured within the receiver to form the multiplanar receiver sub-assembly 11 in the pre-assembled shipping state position. It will be appreciated that with the circumferential recess 176 being firmly engaged by the retaining ridge 125 around a majority portion of its circumference, the pressure ring 170 is thereby restrained or inhibited from axial movement up or down within the central bore 120 until further acted upon either by tooling or by the threaded head 60 of the shank, and with the downwardly-opening partial spherical lower surface 171 of the pressure ring being centralized and stabilized over the bottom opening 104 of the central bore 120. Accordingly, the pre-assembly of the multiplanar receiver sub-assembly 11 is now complete, and the multiplanar receiver sub-assembly 11 is ready for storage and/or shipping and handling, and for eventually attachment to the threaded head 60 of the shank 50 or bone anchor either prior to or during spinal surgery.

Furthermore, it is foreseen that other structures and interconnections between the components of the multiplanar receiver sub-assembly 11 may also be used to secure the pressure ring 170 in its pre-assembled position within the internal cavity 104 of the receiver, with its partial spherical lower surface 171 aligned and centered with the bottom opening 104 at the base portion 106 of the receiver 100, and are considered to fall within the scope of the present disclosure.

One representative method for assembling the multiplanar receiver sub-assembly 11 to the threaded head 60 of the shank 50 is illustrated in FIGS. 32-41. For instance, and with initial reference to FIGS. 32-33, the multiplanar receiver sub-assembly 11 can first be positioned above the proximal end 51 of the shank 50 or bone anchor with the vertical centerline axis 101 of the receiver 100 being substantially co-linear with the longitudinal axis 52 of the shank. The multiplanar receiver sub-assembly 11 is then moved downward (or the shank 50 is moved upward, depending on the frame of reference of the reader) until the top surface 62 of the shank head 60 begins to enter the bottom opening 104 of the receiver 100. In situations where the lower starts 113a, 113b of the lower threads 114a, 114b formed into the bottom opening 104 of the receiver 100 are not initially angularly aligned with the upper starts 67a, 67b of the upper threads 68a, 68b formed into the proximal end of the shank head 60, the leading clearance flanks of the respective threads will abut each other to prevent further axial travel until the receiver is rotated (in a clockwise direction for the embodiment shown in the drawings) so that the respective starts become angularly aligned. Given the opposing 180 degree dual thread/dual lead-in configurations of both the upper thread form 66 of the shank head 60 and the lower thread form 112 of the receiver 100, the amount of rotation needed before the upper and lower starts align will always be less than 180 degrees so as to make the assembly easier and faster.

Figure 33:
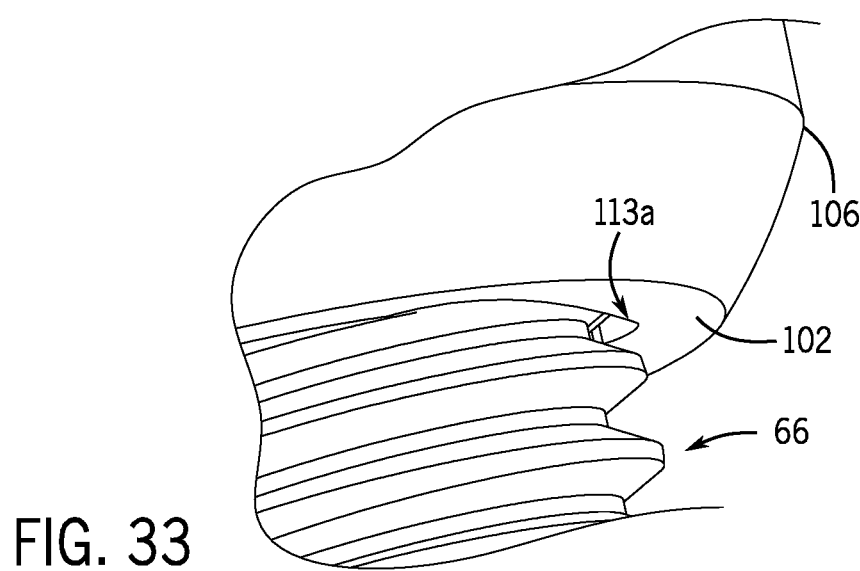
FIG. 33 is a close-up perspective bottom view of the multiplanar receiver sub-assembly of FIGS. 30-31, with the shank head being threadably uploaded through the bottom opening.
Figure 34:
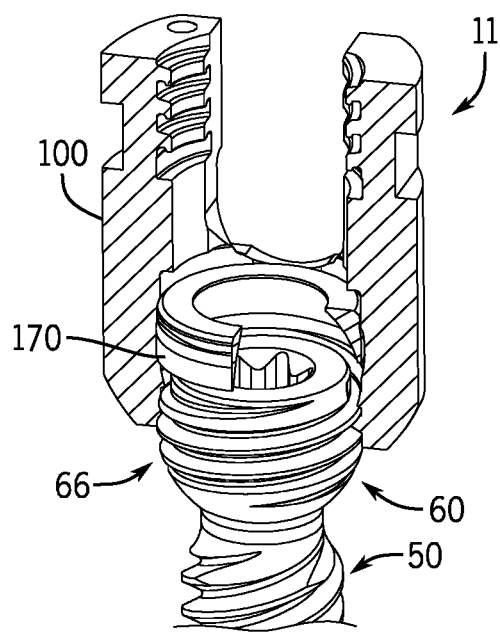
FIG. 34 is a partially cut-away perspective view of the aforementioned multiplanar receiver sub-assembly and shank, with the shank head being partially threadably uploaded into the receiver.
Figure 35:
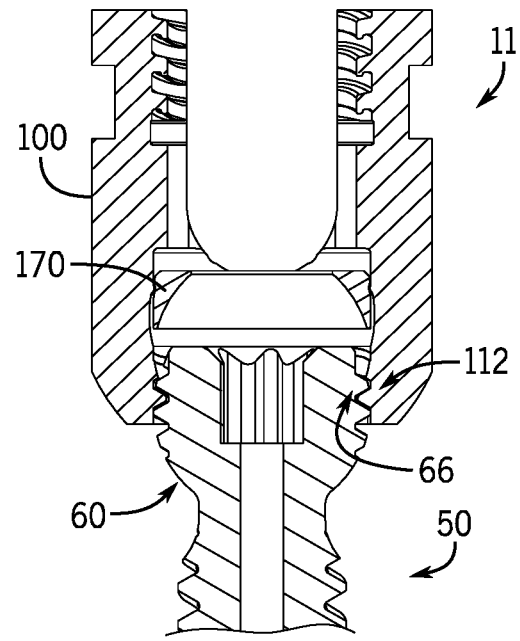
FIG. 35 is a cross-sectional side view of the multiplanar receiver sub-assembly and shank of FIG. 34.

Once the first and second lower starts 113a, 113b of the receiver 100 are angularly aligned with the first and second upper starts 67a, 67b of the shank head 60, the receiver can then drop slightly further down onto the shank head so that the leading faces 154 of the first and second lower starts 113a, 113b can become slidably engaged with the leading faces 70 of the first and second upper starts 67a, 67b. Once the leading faces clear, continued rotation of the receiver 100 relative to the shank head 60 can then cause the leading faces 70, 174 to rotate across each other until the load-flank surfaces 150 of the lower thread form 112 become slidably engaged with load-flank surfaces 76 of the upper thread form 66 of the shank head 60, as shown in FIG. 33. Continued threaded advancement of the multiplanar receiver sub-assembly 11 onto the shank head 60 can be accomplished by rotating the receiver in a clockwise direction (or counterclockwise direction if the threads were reversed) about axes 52 and 101 and onto the shank head 60, as shown in FIGS. 34-35.

Figure 36:
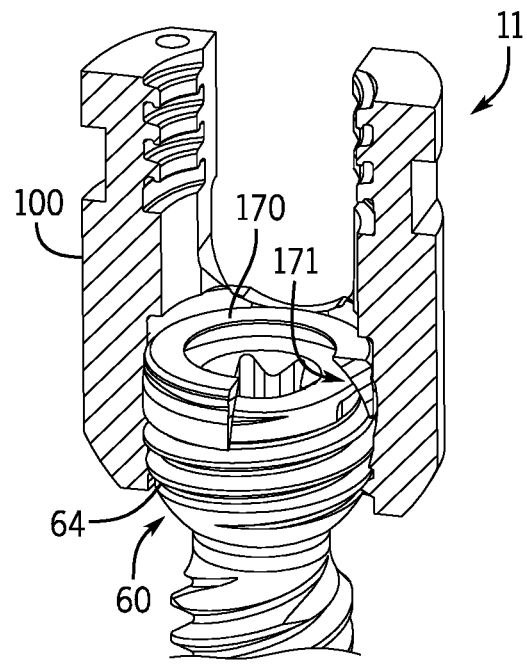
FIG. 36 is another partially cut-away perspective view of the aforementioned multiplanar receiver sub-assembly and shank, with the shank head being further threadably uploaded into the receiver until the shank head engages the partial spherical lower surface of the pressure ring.
Figure 37:
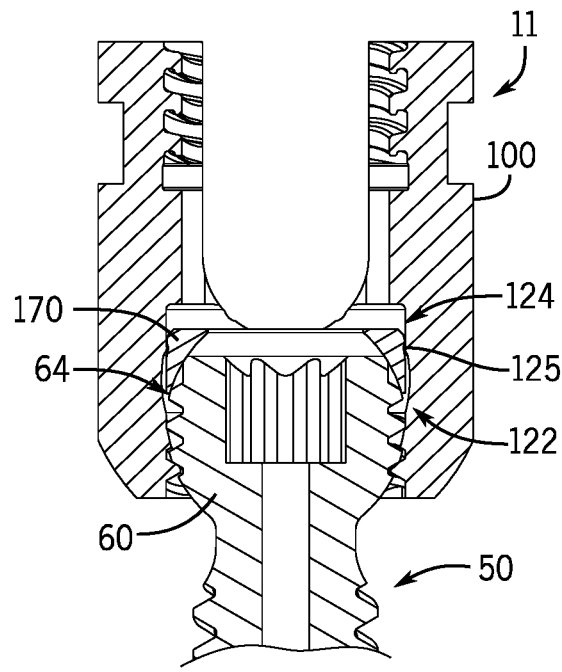
FIG. 37 is a cross-sectional side view of the multiplanar receiver sub-assembly and shank of FIG. 36.

Referring now to FIGS. 36-37, the multiplanar receiver sub-assembly 11 can be freely threadably advanced under rotation onto the shank head 60 until an upper portion of the rounded or partial spherical outer surface 64 of the shank head 60 engages the partial spherical lower surface 171 of the pressure ring 170 that is secured in its pre-assembled shipping state position in the center of the central bore 120.

After reaching this initial contact position, further threaded advancement of the multiplanar receiver sub-assembly 11 under rotation onto the shank head 60 will also then drive or thrust the pressure ring 170 (if present) upward into the upper chamber 124 of the internal cavity 108, with the discontinuous retaining ridge 125 moving downward to engage or ride against the lower cylindrical portion 175 of the lateral outer surface 174 of the pressure ring 170. In one aspect this engagement can be used to establish an interference fit between the pressure ring 170 and the receiver 100 that can create a resistance between the pressure ring 170, the internal cavity 108 of the receiver 100, and the discontinuous partial spherical outer surface 64 of the shank head 60. It will be appreciated that this resistance can be controlled by adjusting the surface profiles (e.g. ramp, curvature, height, etc.) of the lower cylindrical portion 175 of the pressure ring 170 and of the retaining ridge 125 (or by other structures formed into alternative embodiments of the present disclosure).

Figure 38:
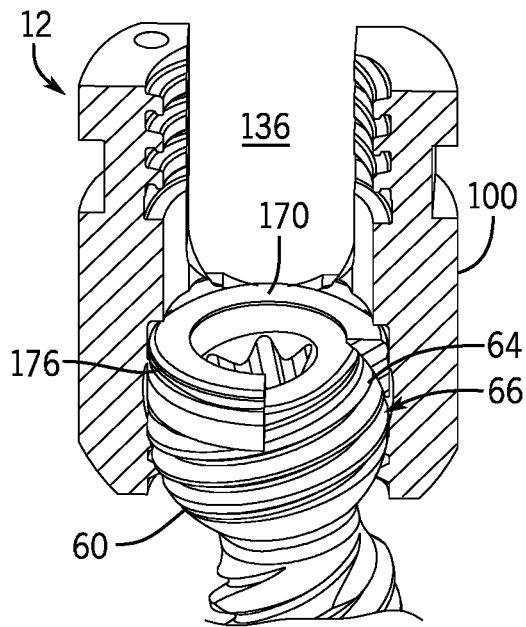
FIG. 38 is a partially cut-away perspective view of the aforementioned multiplanar receiver sub-assembly and shank, with the shank head being fully threadably uploaded to the cavity of the receiver to force the pressure ring upwards from the shipping state position to a friction fit position, prior to and in preparation for installing the elongate rod and closure.
Figure 39:
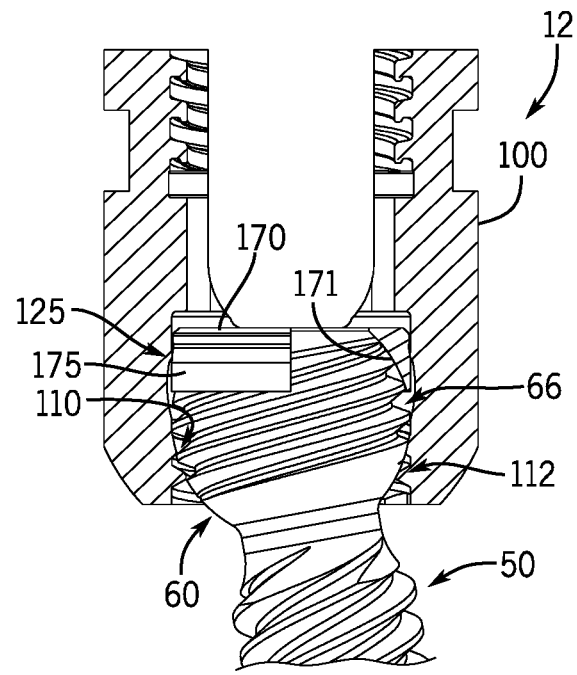
FIG. 39 is a cross-sectional side view of the multiplanar receiver sub-assembly and shank of FIG. 38.

With reference to FIGS. 38-39, continued rotation of the multiplanar receiver sub-assembly 11 onto the shank head 60 will act to further threadably advance the shank head upwardly within the central bore, with the discontinuous partial spherical outer surface 64 of the shank head 60 continuing to drive the pressure ring 170 upwards against the resistance provided by the pressure ring 170, until the upper thread form 66 of the shank head 60 passes completely through and disengages from the lower thread form 112 of the receiver and the upward thrust provided by the engagement between the threadforms drops to zero. At this point the receiver 100 can now rotate and pivot relative to the shank head 60 so that the rod channel 136 of the receiver can be aligned with the eventual position of the elongate rod that will be installed between adjacent bone anchor assemblies to complete the spinal construct. Assuming the anchor portion 84 of the bone anchor or shank 50 is fixably secured to the bone of the patient, in this state or configuration the discontinuous partial spherical lower seating surface 110 of the internal cavity, as defined by the sum of the inwardly facing crest surfaces 118 of the first and second lower threads 114a, 114b, can slide over or around the partial spherical outer surface 64 of the shank head 60, as defined in part by the sum of the outwardly-facing crest surfaces 74 of the first and second upper threads 68a, 68b.

With the pressure ring 170 no longer being driven upwards, as shown in FIGS. 38-39, the threaded shank head 60 and pressure ring 170 are now in the lower friction fit position in which the shank head can be forcibly clamped between the pressure ring and the lower seating surface 110 of the receiver. Specifically, the partial spherical lower surface 171 of the pressure ring 170 can slidably frictionally engage the upper portion of the partial spherical outer surface 64 of the shank head 60 while the lower seating surface 110 of the internal cavity 108 can slidably frictionally engage the lower portion of the partial spherical outer surface 64. At the same time, the lower cylindrical portion 175 of the lateral outer surface 174 of the pressure ring can also continue to be engaged by the retaining ridge 125, thereby maintaining the interference fit between the pressure ring 170 and the receiver 100 that can hold the pressure ring 100 (or more specifically, the partial spherical lower surface 171) downward and in frictional engagement with the upper portion of the partial spherical outer surface 64 of the threaded shank head 60.

The pre-lock non-floppy friction fit provided by the pressure ring 170 (or structures) can be sufficient to hold the position of the multiplanar receiver sub-assembly 11 relative to the shank head 60 while still allowing for movement of the multiplanar receiver sub-assembly 11 relative to the shank 50 with an applied force. In other words, the pre-lock non-floppy friction fit can allow for rotation of the multiplanar receiver sub-assembly 11 around the shank head 60 only with an applied twisting force, and for angulation of the multiplanar receiver sub-assembly 11 relative the shank head 60 only with an applied moment force. As such, a user or surgeon may therefore establish and maintain an alignment of the rod channel 136 of the receiver 100 with the rod channels of one or more adjacent bone anchor assemblies in the spinal construct without further manipulation of the pressure ring 170.

Figure 40:
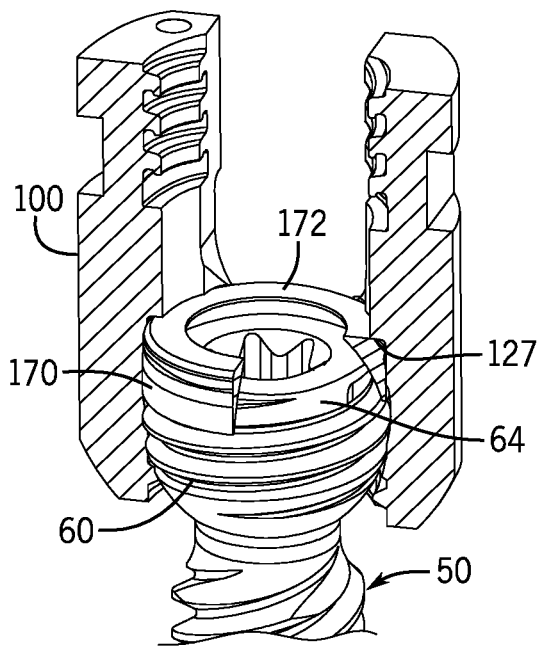
FIG. 40 is a partially cut-away perspective view of the aforementioned multiplanar receiver sub-assembly and shank, showing the tolerances that optionally allow for the shank head to be driven upwardly within the cavity of the receiver beyond the friction fit position, and thereby force the pressure ring upwards to the maximum travel position.
Figure 41:
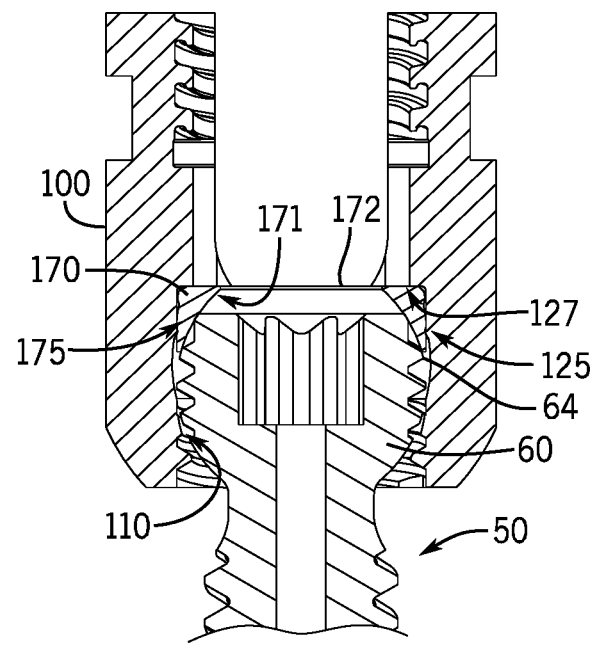
FIG. 41 is a cross-sectional side view of the multiplanar receiver sub-assembly and shank of FIG. 40.

Although it is contemplated that the relative positions of the pressure ring 170 and shank head 60 within the internal cavity 108 shown in FIGS. 38-39 can be maintained by the interference fit between lateral outer surface 174 of the pressure ring 170 and the retaining ridge 125, it will also be appreciated that in some conditions the receiver may continue to travel downwards (or the shank head and pressure ring upwards) the remaining short distance until the annular top surface 172 of the pressure ring 170 engages or abuts the downwardly-facing discontinuous annular step surface 127 at the upper end of the internal cavity 108, as shown in FIGS. 40-41, denoting the maximum upward travel position of the threaded shank head 60. Thus, in one aspect the step surface 127 can serve as a stop surface that prevents both the pressure ring 170 and the shank head 60 from continuing too far upward within the central bore 120 of the receiver after the disengagement between the thread forms 66, 112. It will also be appreciated that the remaining short distance to the maximum travel position can be provided by manufacturing tolerances to ensure that the upper thread form 66 can completely exit the lower thread form 112. With the top surface 172 of the pressure ring 170 in engagement with downwardly-facing step surface 127 at the upper end of the internal cavity 108, and depending upon the closeness of the manufacturing tolerances discussed above, the engagement between the component surfaces may or may not be tight enough to establish the pre-lock non-floppy friction fit without further manipulation of the pressure ring 170.

For example, in some embodiments the tolerances between the components may be tight enough to establish a friction fit that is sufficient to hold the position of the multiplanar receiver sub-assembly 11 relative to the shank head 60 while still allowing for movement of the multiplanar receiver sub-assembly 11 relative to the shank 50 with an applied force. Nevertheless, in other embodiments the tolerances between the component surfaces of in the maximum travel position, will not be tight enough to establish a friction fit between the multiplanar receiver sub-assembly 11 and the shank head 60 when the top surface 172 of the pressure ring 170 is abutting the downwardly-facing step surface 127 of the internal cavity 108 in the maximum travel position, so that the multiplanar receiver sub-assembly 11 would be free to slip downwards under gravity relative to the shank 50, in a floppy fashion, unless otherwise held in position by tooling or by the user. The pressure ring 170 may therefore require downward movement or deployment relative to the central bore of the receiver to a lower friction fit position in order to forcefully close the remaining gaps between the components and to establish the pre-lock non-floppy friction fit between the multiplanar receiver sub-assembly 11 and the shank head 60 shown in FIGS. 38-39.

It will be appreciated that the downward movement or deployment of the pressure ring 170, from the maximum travel position shown in FIGS. 40-41 back to the non-floppy friction fit position shown in FIGS. 38-39 can be provided in a number of different ways. For instance, in one embodiment the pressure ring 170 can be forcefully moved back downward within the central bore 120 with tooling (not shown) having, in one aspect, a center portion that can apply pressure to the annular top surface 172 of the pressure ring 170 while an outer portion engages one or more pairs of tooling engagement recesses 144, 148 in order to hold and align the receiver during the deployment process. Such tooling may also serve to hold and manipulate the receiver sub-assemblies while they are being attached to the shank head. Alternatively, in another embodiment the pressure ring may be modified to interface with a wave spring or similar spring-like device (also not shown) that is compressed between the upper surface of the pressure ring and the downwardly-facing step surface 127 of the internal cavity 108, for example, so as to bias the pressure ring downward into the lower friction fit position after the disengagement between the thread forms 66, 112.

In yet other embodiments the pressure ring may be modified to include integrally-formed downwardly-extending collet fingers, or to mate with a separate clamp ring having downwardly-extending clamp fingers, both of which can operate to grip the discontinuous partial spherical outer surface 64 of the shank head 60 with a non-floppy friction fit after the disengagement between the thread forms 66, 112 upon completion of uploading of the threaded universal shank head 60 into the internal cavity 108 of the receiver 100. These and other embodiments having alternative structures that provide similar functionality are also foreseen and considered to fall within the scope of the present disclosure. As described in more detail below, for example, the pressure ring may also be replaced by a lower pressure insert with integral or separate spring tabs that engage with internal surfaces of the receiver arms to provide a downwardly-directed engagement force to establish the non-floppy friction fit, and which lower pressure insert could also be rotated or twisted into position within the receiver.

As described above, once the upper thread form 66 of the shank head 60 clears the lower thread form 112 of the receiver, and the shank head 60 and pressure ring 170 reach the lower friction fit position shown in FIGS. 38-39, the receiver can then rotate and pivot relative to and in close engagement with the threaded universal shank head 60. In addition, the interference engagement between the lateral outer surface 174 of the pressure ring 170 and the retaining ridge 125 of the internal cavity 108 can hold the pressure ring in its position within the internal cavity 108, so as to establish and maintain the pre-lock non-floppy friction fit engagement between the discontinuous partial spherical outer surface 64 of the shank head 60, the partial spherical lower surface 171 of the pressure ring 170, and the threaded or discontinuous partial spherical lower seating surface 110 of the internal cavity 108. The bone anchor assembly 12 is then ready for alignment of the rod channel 136 of the receiver 100 with the rod channels of one or more adjacent bone anchor assemblies in the spinal construct, and for its continued assembly with the elongate rod and a closure.

Figure 42:
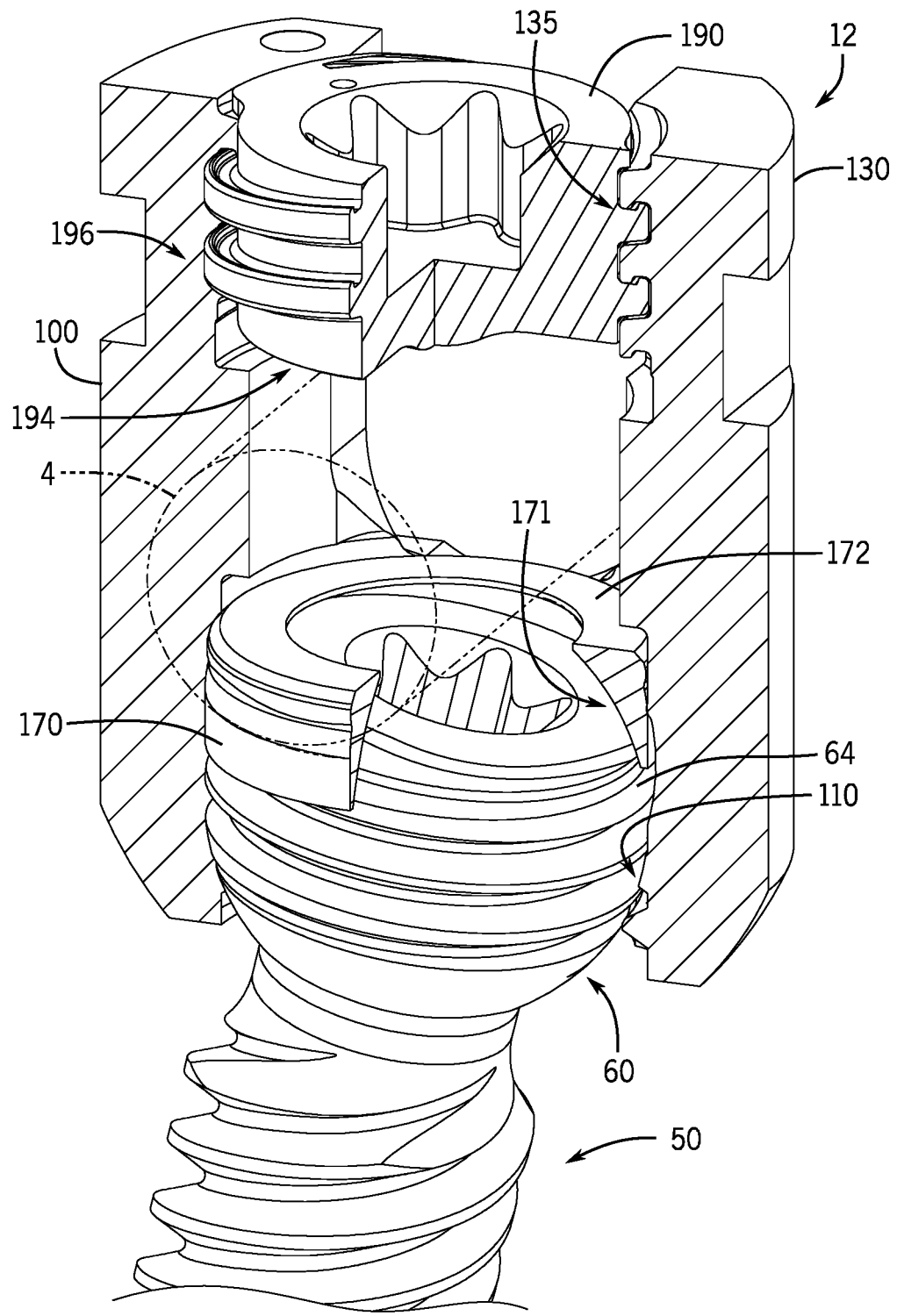
FIG. 42 is a partially cut-away perspective view of the aforementioned multiplanar receiver sub-assembly and shank after assembly together and with the elongate rod and closure of FIG. 2 into a fully assembled and locked multiplanar pivotal bone anchor assembly.
Figure 43:
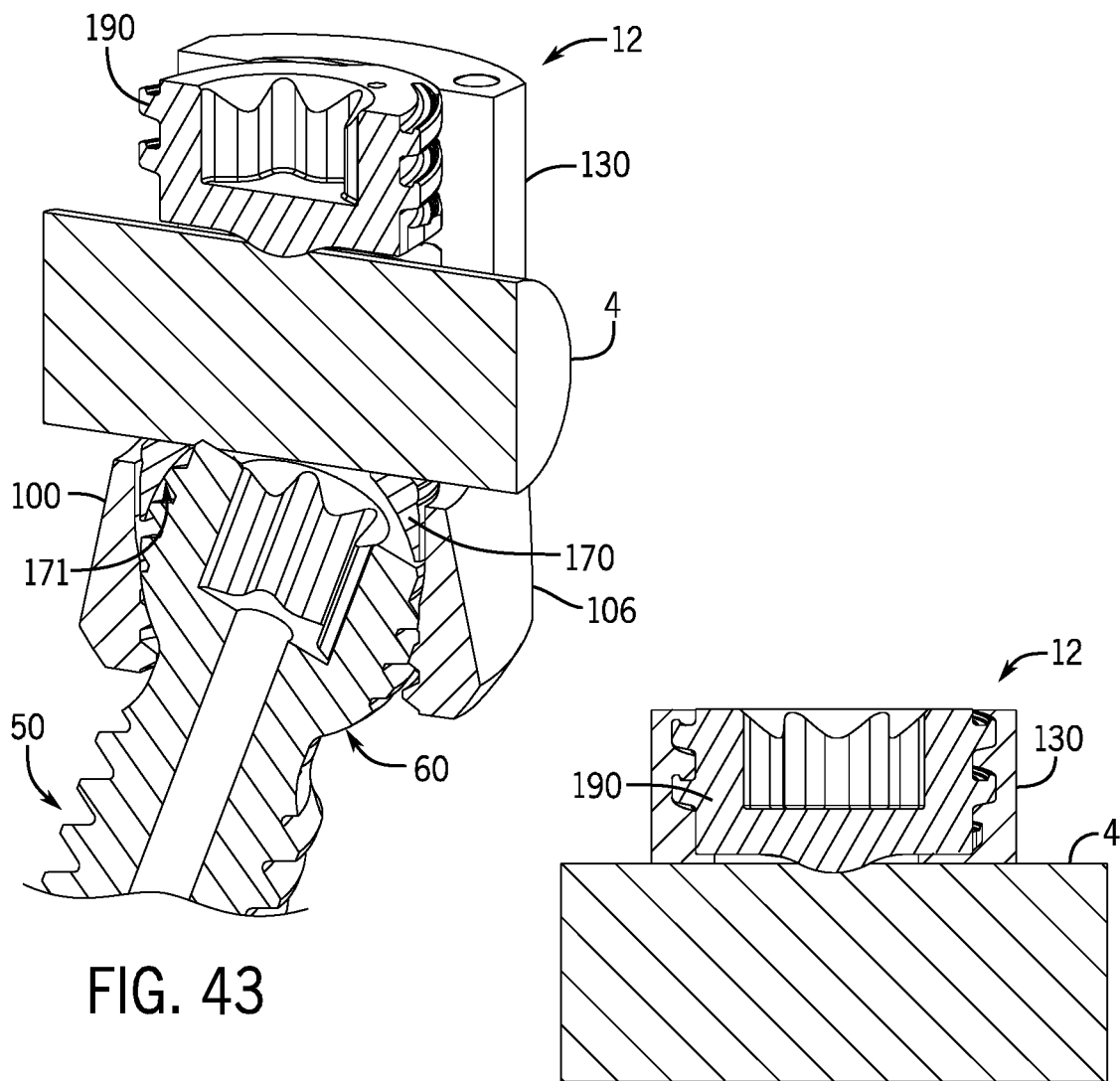
FIG. 43 is a cross-sectional perspective side view of the fully assembled multiplanar pivotal bone anchor assembly of FIG. 42.
Figure 44:
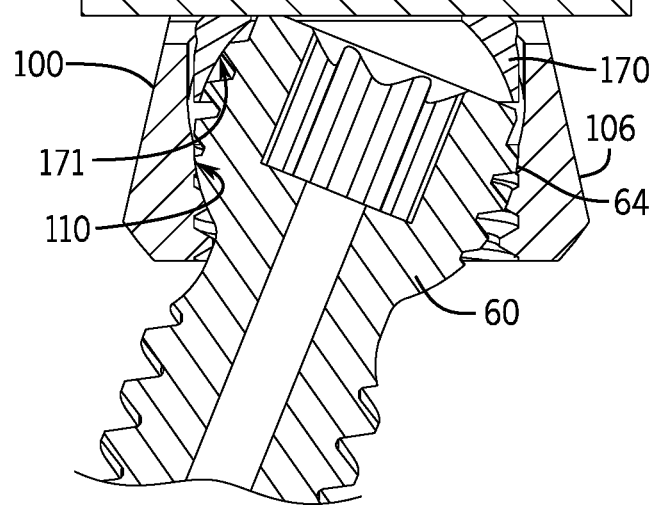
FIG. 44 is a cross-sectional side view of the fully assembled multiplanar pivotal bone anchor assembly of FIG. 42.
Figure 45:
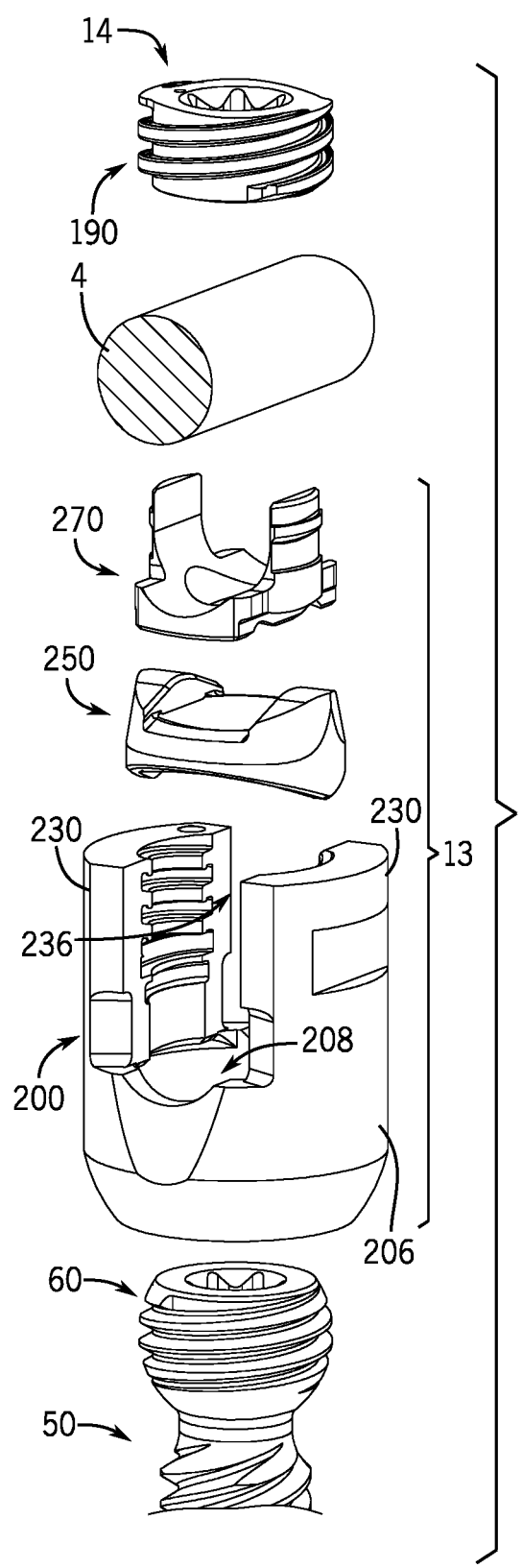
FIG. 45 is an exploded perspective view of the monoplanar pivotal bone anchor assembly of the spinal fixation system of FIG. 1, in accordance with another representative embodiment of the present disclosure.
Figure 46:
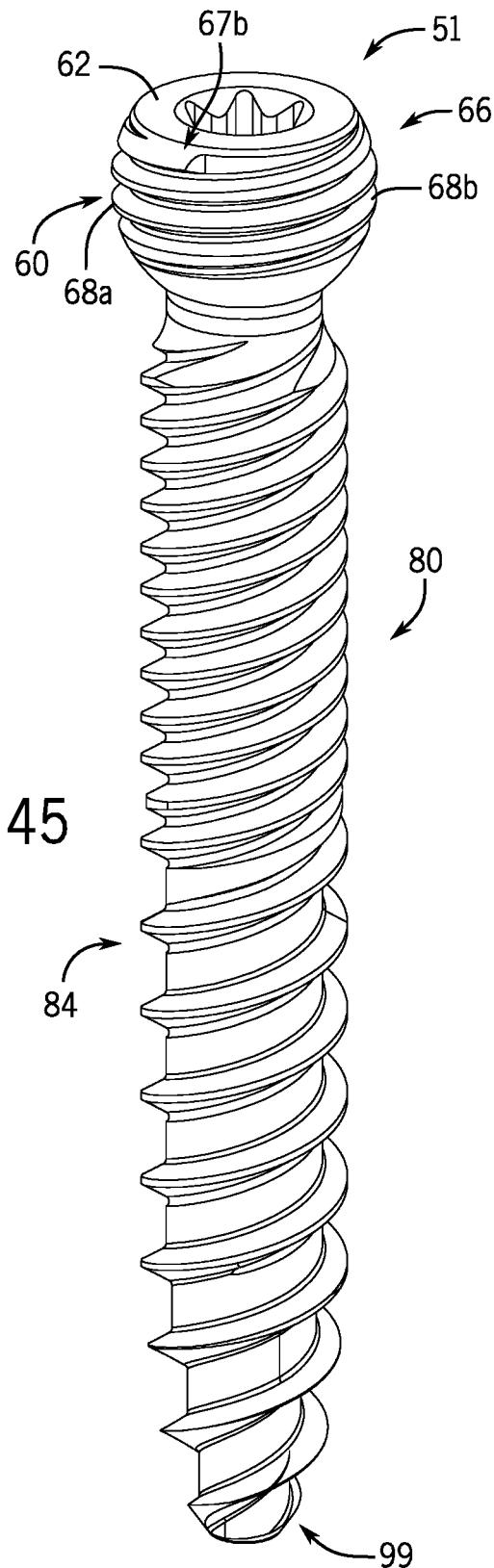
FIG. 46 is a perspective view of the bone anchor or shank shown in FIG. 45 having a threaded universal shank head.

Illustrated in FIGS. 42-44 is the multiplanar pivotal bone anchor assembly 12 as fully assembled and locked with the elongate rod 4 and the single-piece closure 190. For instance, after a desired alignment of the rod channel 136 of the receiver 100 has been achieved via manipulation of the multiplanar receiver sub-assembly 11 relative to the shank head 60, with the pressure ring 170 in the friction fit position, the elongate rod 4 can be installed (i.e. reduced) into the rod channel 136, such as with instruments and/or breakoff extensions on the upright arms 130, until the lowermost or underside surface of the elongate rod 4 approaches the annular top surface 172 of the pressure ring 170. The closure 190 can then be installed into the upper portion of the central bore 120 of the receiver 100 (or breakoff extensions), in which the outer continuous guide and advancement structure 196 of the closure 190 rotatably engages the discontinuous guide and advancement structure 135 formed into the interior faces 131 of the receiver upright arms 130 (and breakoff extensions). The closure 190 can be threaded downwardly until the bottom surface 194 of the closure 190, or the downwardly-projecting central projection 195 protruding therefrom, engages the top surface of the elongate rod 4. Further rotation and torquing of the closure 190 can then be used to drive the elongate rod 4 downward onto the pressure ring 170, which in turn drives the shank head 60 further downward on the threaded or discontinuous partial spherical lower seating surface 110 of the internal cavity 108 of the receiver 100 to achieve a final locking of the multiplanar bone anchor assembly 12, in which the multiplanar receiver sub-assembly 11 can no longer pivot or rotate relative to the shank 50.

Thus, the components of the multiplanar receiver sub-assembly 11 are generally configured to provide a multiplanar pivotable connection with the shank 50 prior to fixing or locking the shank 50 in a desired position with respect to the multiplanar receiver sub-assembly 11. Nevertheless, it is foreseen that the receiver sub-assembly and its components may be modified or additional components may be added to provide for a uni-planar pivotable connection, or even a non-pivoting connection, with the same threaded shank head 60. Thus, as noted above, the threaded shank head 60 may also be referenced as or considered to be a threaded universal shank head, since a number of different types of receiver head assemblies, with each type providing different degrees of freedom or modes of movement relative to the shank, can be threadably coupled to the same shank head 60.

With reference to FIGS. 45 and 46-57, for example, illustrated therein is a monoplanar pivotal bone anchor apparatus or assembly 14 in accordance with another representative embodiment of the present disclosure. The monoplanar bone anchor assembly 14 can include the same bone anchor or implantable shank 50 (see FIG. 46) described in reference to the multiplanar bone anchor assembly that includes the threaded universal capture portion or shank head 60 with a rounded shape at a proximal end 51, and the shank body 80 extending distally from the threaded head 60 with the anchor portion 84 at a distal end 99 that is configured for securement to the bone. As previously described, the shank head 60 can further include the annular planar top surface 62 at an upper end and the discontinuous partial spherical outer surface 64 adjacent the top surface having an upper thread form 66 formed therein. In one aspect the upper thread form 66 can be a dual lead threadform further comprising a pair of helically wound upper threadforms 68a, 68b with crest surfaces defining the discontinuous portions of the partial spherical outer surface 64, with each of the upper threadforms having an upper start structure 67a, 67b extending upwards towards the top surface 62 of the shank head 60.

Figure 47:
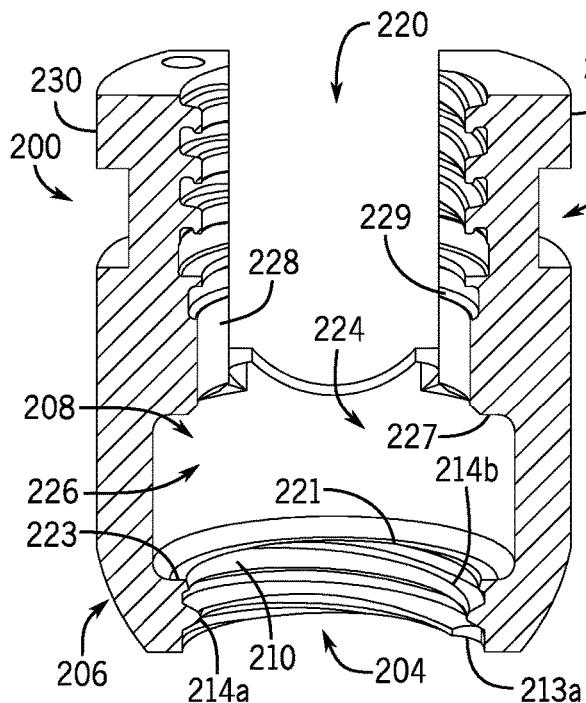
FIG. 47 is a cross-sectional perspective front view of the monoplanar receiver of FIG. 45.
Figure 48:
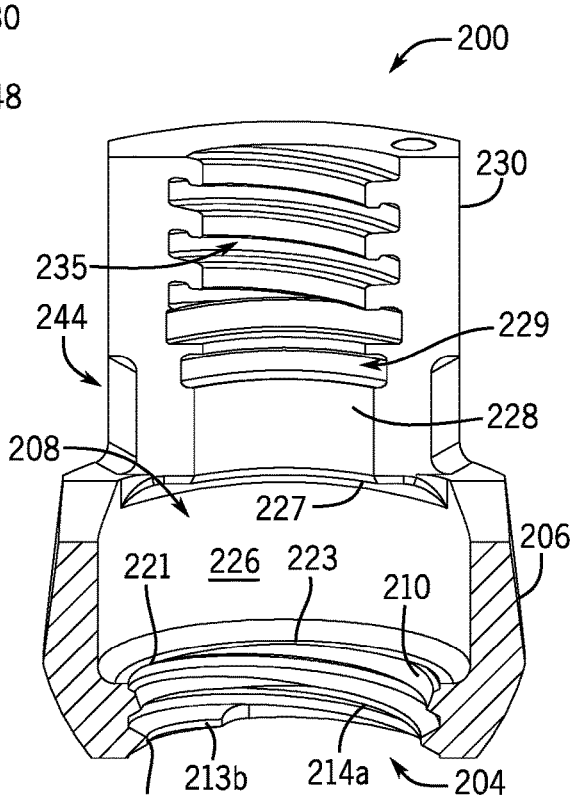
FIG. 48 is a cross-sectional perspective side view of the monoplanar receiver of FIG. 45.

The monoplanar bone anchor assembly 14 also includes a monoplanar receiver 200 having a cylindrical base portion 206 defining an internal cavity 208 portion of a central bore, and two upright arms 230 extending upwardly from the base portion 206 to define a rod channel 236 configured for receiving the elongate rod 4. As shown in FIGS. 47-48, the internal cavity 208 can further include a bottom opening 204 and a lower seating surface 210 that is configured to receive and support the threaded universal head 60 of the shank 50 within a lower portion of the internal cavity 208 of the monoplanar receiver 200. The lower seating surface 210 generally comprises a discontinuous partial spherical surface curving downward and inward from a transition edge to the bottom opening 204 that opens onto the bottom surface 202 of the monoplanar receiver 200, and having a lower thread form 412 formed therein. In particular, the lower thread form 212 is configured to engage the upper thread form 66 of the threaded universal shank head 60 upon insertion and rotation thereof. Therefore, in one aspect the lower thread form 212 can also be a dual lead threadform further comprising helically wound first and second lower threads 214a, 214b having respective first and second lower starts 213a, 213b that are configured to engage with the dual thread/dual lead-in structures of the upper thread form 66.

The monoplanar bone anchor assembly 14 can further include a two-piece monoplanar insert comprising a rod-receiving upper insert 270 and a shank-engaging lower rocker 250. The upper insert 270 and lower rocker 250 can be pre-assembled together into the central bore 220 of the receiver 200 to form the monoplanar receiver sub-assembly 13, after which the threaded universal shank head 60 of the shank 50 can be threadably uploaded into the internal cavity 208 and pivotably coupled or secured to the monoplanar receiver sub-assembly 13. Upon the monoplanar receiver sub-assembly 13 being coupled to the shank head 60, the elongate rod 4 can be positioned within the rod channel 236 and a closure 190 can then be threadably or otherwise secured into the rod channel 236 above the elongate rod 4 so as to apply a force or pressure against an upper surface of the elongate rod 4. This force or pressure is transmitted downward through the elongate rod 4, the upper insert 270, the lower rocker 250, the shank head 60, and ultimately through to a lower portion of the receiver 200, thereby locking both the elongate rod 4 and the multiplanar bone anchor assembly 12 into a final locked position.

With continued reference to FIGS. 47-48, the upper discontinuous portion of the central bore 220 of the monoplanar receiver 200, immediately below the guide and advancement structure 235 and between the opposed parallel planar surfaces 232, can be defined by an inwardly-facing discontinuous upper cylindrical surface 228 that extends downward from the guide and advancement structure 235 toward a downwardly-facing discontinuous annular step surface 227. Formed into the discontinuous cylindrical surface 228 is a "shipping state" groove or recess 229 spaced below the guide and advancement structure 235. Similar to the multiplanar receiver, the discontinuous annular step surface 227 can demark the bottom of the discontinuous upper cylindrical surface 228 and the top of the internal cavity 208. However, other features or aspects of the internal cavity 208 of the monoplanar receiver 200 can differ from those of the multiplanar embodiment, so as to accommodate a different set of internal components that together form the monoplanar receiver sub-assembly 13. For example, the cylindrical surface 226 that defines the upper chamber 224 of the internal cavity 208 of the receiver 200 can be expanded and lengthened to as to enlarge and extend the upper chamber 224 downward from the downwardly-facing discontinuous annular step surface 227 to an upward-facing annular step surface 223, which annular step surface 223 extends between the cylindrical surface 226 and the circular transition edge 221 demarking the transition to the discontinuous lower seating surface 210.

Many elements of the monoplanar receiver 200 can be similar to the corresponding elements of the multiplanar receiver 100 described above, including but not limited to the splay-resisting or splay-controlling aspects of the discontinuous guide and advancement structure 235, break-off extensions, and the tool engagement recesses 244, 248 or grooves formed into the front and back and lateral exterior surfaces. Nevertheless, alternative elements that differ from those shown in the drawings while providing for similar interaction and functionality of the various components of the monoplanar bone anchor assembly 14 are also possible and considered to fall within the scope of the present disclosure.

As described above, the monoplanar bone anchor assembly 14 can further include a multi-piece monoplanar insert, such as a two-piece monoplanar insert comprising a rod-receiving upper insert 270 and a shank-engaging lower rocker 250, which upper insert 270 and lower rocker 250 can be pre-assembled together into the central bore 220 of the receiver 200 to form the monoplanar receiver sub-assembly 13 in a shipping state configuration.

Figure 49:
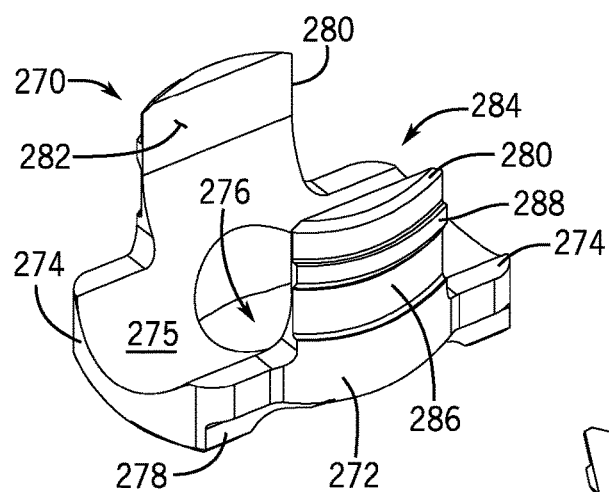
FIG. 49 is an upper perspective view of the upper insert piece of the monoplanar insert shown in FIG. 45.
Figure 50:
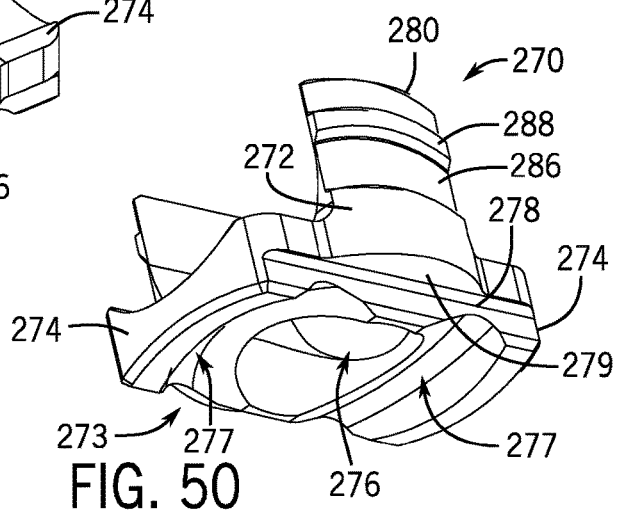
FIG. 50 is an lower perspective view of the upper insert piece of the monoplanar insert shown in FIG. 45.

With reference to FIGS. 49-50, the upper insert 270 generally includes a base portion 272 with integral insert arms 280 projecting upwardly or proximally from the base portion 272 to define an insert channel 284 that is alignable with the receiver channel 236 upon installation of the upper insert 270 into the receiver 200. The interior surfaces of the insert arms 280 include upper planar surfaces 282 that curve downwardly into the U-shaped upper surfaces 275 of opposed radial extensions 274 that project radially outward from the base portion 272 between the insert upright arms 280. The upper planar surfaces 282 of the insert arms 280 are located on either side of a tool receiving central aperture 276 that extends vertically downward through the base portion 272 to allow passage for a driving tool to engage the internal drive feature 54 or drive socket formed into the top of a threaded universal shank head 60 that is captured within the internal cavity 208 of the receiver 200. As illustrated in the drawings, the central aperture 276 can be smooth and non-threaded.

Protruding radially outwardly from outer side surfaces 286 of the insert arms 280 are opposed lateral ridges 288 that are configured for "snap-in" engagement with the shipping state grooves or recesses 229 formed into the interior faces of the upright arms 236 of the receiver 200 when the receiver sub-assembly 13 is in the pre-assembled shipping state position. The protruding lateral ridges 288 can be non-threaded, and in one aspect a small rounded relief groove (not shown) can be formed at the junction between the vertical outer side surfaces 286 of the insert arms 280 and the top surfaces of the opposed lateral ridges 288. Moreover, it is foreseen that the arrangement of protruding ridges and recesses on the upper insert 270 and the receiver 200, respectively, can be reversed, with the shipping state recesses being formed into the exterior or outer surface of the upper insert 270 and the internal ridges protruding inwardly from the central bore 220 of the receiver 200. Other combinations of ridges and grooves, or entirely different structures, including but not limited to ratchets, a separate snap ring, and the like, are also possible.

The underside surfaces 273 of the base portion 272 of the upper insert 270, which includes the underside surfaces of the opposed radial extensions 274, can include rocker-receiving recesses 277 oriented transverse to the insert channel 284, and that extend upward into the base portion 272 on either side of the central aperture 276 so as to provide clearance for the pivotal motion of the lower rocker 250 relative to the upper insert 270 when the two are assembled together. In addition, horizontally-elongate outwardly-facing planar guide surfaces 278 and downwardly-facing planar guide surfaces 279 can be formed into the lower side faces of the base portion 272 and opposed radial extensions 274, extending horizontally toward the outer ends of the opposed radial extensions 274. The planar guide surfaces 278, 279 can provide engagement surfaces with complementary inwardly-facing planar surfaces and curved top surfaces of the lower rocker, respectively, that can limit or control the pivoting motion of the lower rocker, and thereby the shank, to a single plane.

Figure 51:
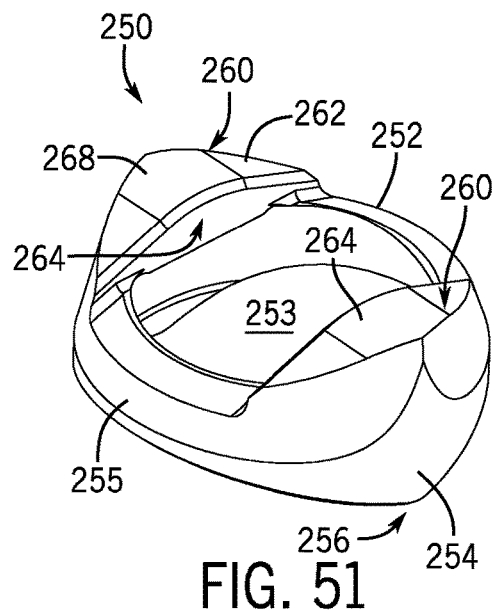
FIG. 51 is an upper perspective view of the lower rocker piece of the monoplanar insert shown in FIG. 45.
Figure 52:
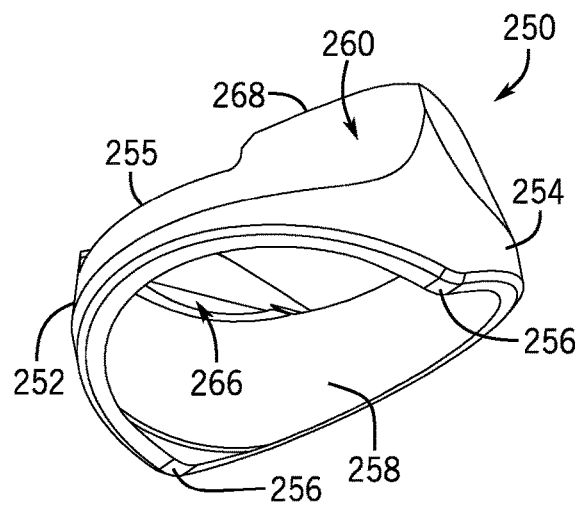
FIG. 52 is an lower perspective view of the lower rocker piece of the monoplanar insert shown in FIG. 45.

With reference to FIGS. 51-52, the lower rocker 250 generally includes a ring-shaped body 252 having a central opening 253 and opposed upper cap structures 260 located above opposed triangularly-shaped downwardly-extending skirt portions 254. The triangular skirt portions 254 point downward to define bottom apex edges 256 that are configured to rest upon the upward-facing annular step surface 223 of the internal cavity 208 of the receiver 200, thereby providing a spaced-apart two-point pivot reference that allows for the lower rocker 250 to stably pivot back and forth within the internal cavity 208. In addition, the lower interior surface 258 of the ring-shaped body 252 and triangular skirt portions 254 is a downward-opening partial spherical surface that is sized to closely receiver an upper portion of the rounded or partial spherical outer surface 64 of the threaded universal shank head 60. The ring-shaped body 252 can further include transverse sections 255 that extend between the upper cap structures 260, and having outer side surfaces and top surfaces that are sized and shaped to rotate up into the rocker-receiving recesses 277 formed into the underside surfaces of the insert body 274 and opposed radial extensions 274 of the upper insert.

The upper cap structures 260 of the lower rocker 250 have inner portions 262 that overlie and partially close or square the central opening 253 of the ring-shaped body 252 to form an elongate top slot. The inner portions 262 include opposed inwardly-facing horizontally-elongate planar guide surfaces 264 that are configured to slidably engage the outwardly-facing planar guide surfaces 278 of the upper insert 270 upon assembly together within the monoplanar receiver 200. In addition, the underside surfaces 266 of the inner portions 262 of the upper cap structures 260 are downward-facing planar surfaces configured to engage with the annular planar top surface 62 of the threaded universal shank head 60, as described below. The upper cap structures 260 also have curved top surfaces 268 are sized to be closely received by the downwardly-facing discontinuous annular step surfaces 227 that defined the upper end of the internal cavity 208, and are also curved so as to provide clearance for the pivotal motion of the lower rocker 250 on the pivot line defined by the bottom apex edges 256.

Figure 53:
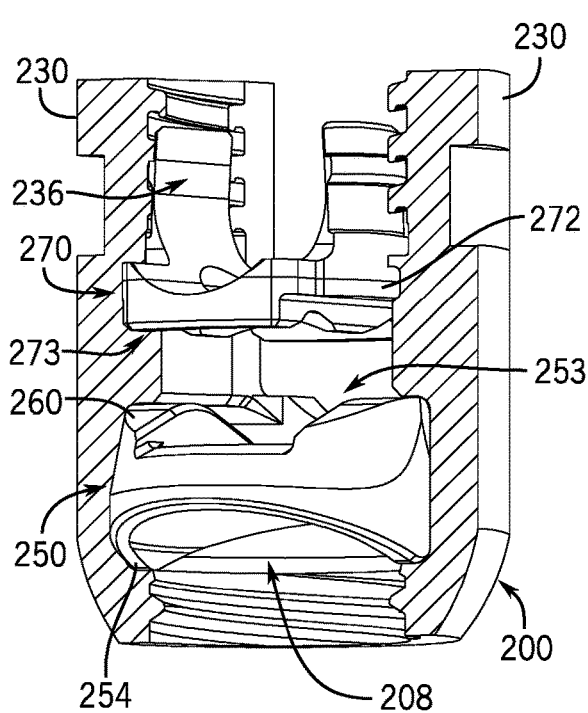
FIG. 53 is a partially cut-away perspective view of the monoplanar receiver and insert of FIG. 45 during assembly of the lower rocker piece and upper insert piece into the central bore of the monoplanar receiver.
Figure 54:
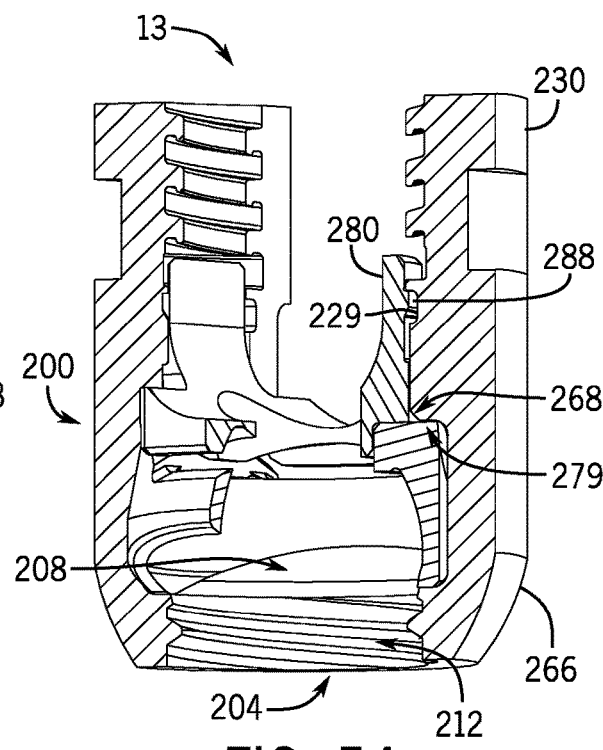
FIG. 54 is a partially cut-away perspective view of the monoplanar receiver and insert of FIG. 45 after assembly of the lower rocker piece and upper insert piece into the central bore of the monoplanar receiver to form the completed monoplanar receiver sub-assembly.

As shown in FIG. 53, the lower rocker 250 can be downloaded or top loaded first into the internal cavity 208 of the receiver 200 and positioned so that the opposed upper cap structures 260 and downwardly-extending skirt portions 254 are below the inner surfaces of the upright arms 230 and the partially-squared central opening 253 is aligned with the rod channel 236. The upper insert 270 can then be downloaded through the rod channel 236 until the underside 273 of the base portion 272 of the upper insert 270 fits into the elongate top slot defined by the opposed inwardly-facing horizontally-elongate planar guide surfaces 264 of the upper cap structures, with the downwardly-facing planar guide surfaces 279 resting on the curved top surfaces 268. At the same time the opposed lateral ridges 288 projecting laterally outward from the outer side surfaces of the insert arms 280 can snap into the shipping state grooves 229 formed into the interior faces of the upright arms 236 of the receiver 200, as shown in FIG. 54. The pre-assembly of the individual monoplanar receiver 200, lower rocker 250, and upper insert 270 components into the mono-planar receiver sub-assembly 13 in the shipping state condition is now complete.

Figure 55:
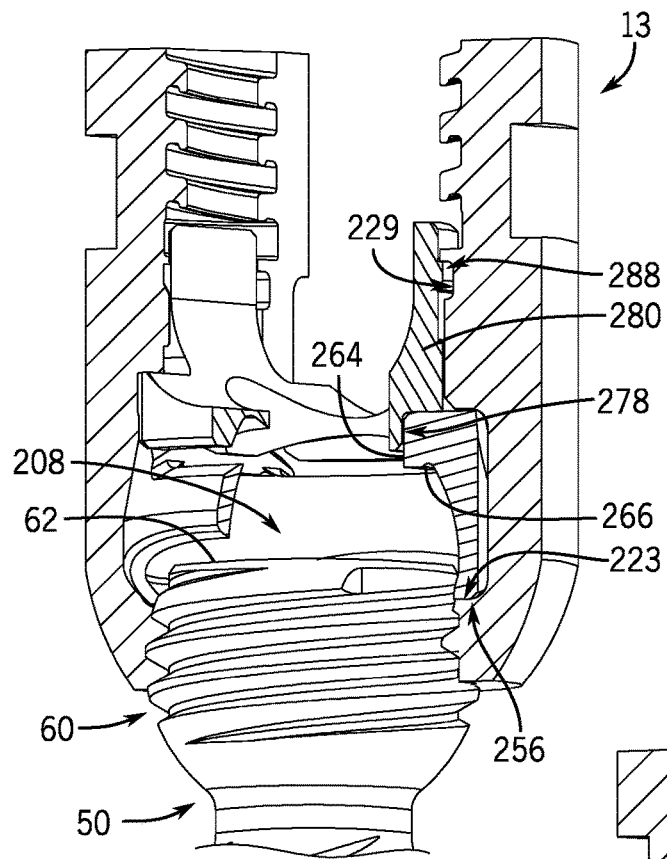
FIG. 55 is a partially cut-away perspective view of the aforementioned monoplanar receiver sub-assembly and the threaded universal shank head being threadably coupled together.
Figure 56:
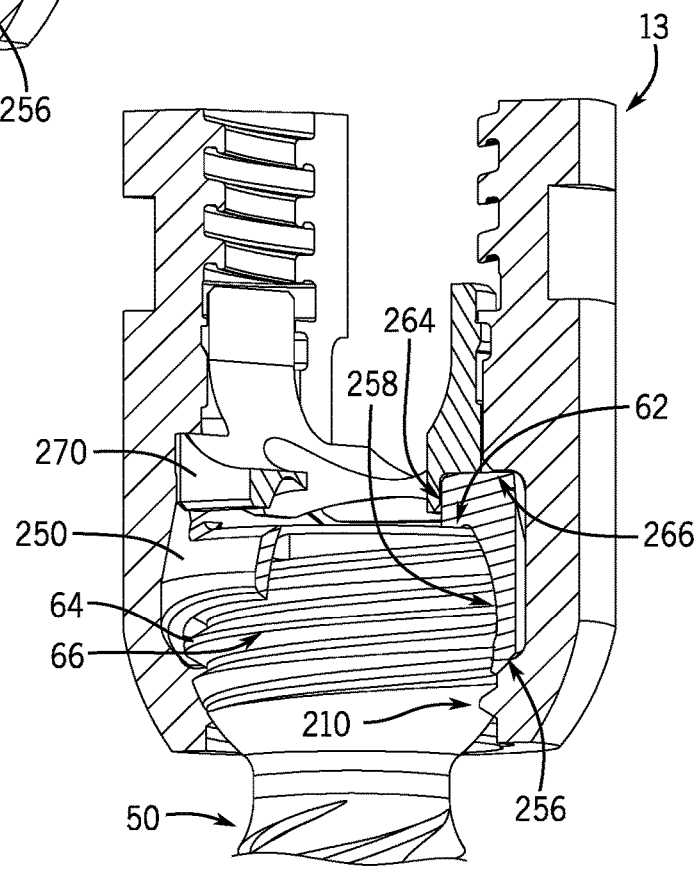
FIG. 56 is a partially cut-away perspective view of the aforementioned monoplanar receiver sub-assembly and the threaded universal shank head after being threadably coupled together.

With reference to FIGS. 55-56, the shank head 60 can then be threadably uploaded into the internal cavity 208 of the monoplanar receiver sub-assembly 13, through to the upper thread form 66 of the shank head 60 clearing and releasing from the lower thread form 212 of the receiver 200, so as to become pivotably coupled or secured to the monoplanar receiver sub-assembly 13. Upon the threaded uploading of the shank head 60 into the internal cavity 208, as shown in FIG. 56, the annular planar top surface 62 of the shank head 60 can engage the planar underside surfaces 266 of the upper cap structures 260, which engagements can serve to inhibit or prevent any further pivotal motion between the shank 50 and the lower rocker 250, so that the shank 50 and lower rocker 250 can only pivot together along the pivot line defined by the bottom apex edges 256 of the lower rocker 250 bearing against the upward-facing annular step surface 223 of the internal cavity 208 of the receiver 200. At the same time, the engagements between the inwardly-facing horizontally-elongate planar guide surfaces 264 of the lower rocker 250 and the horizontally-elongate outwardly-facing planar guide surfaces 278 of the upper insert can serve to restrict or limit any further pivotal motion between the lower rocker 250 and the upper insert 270 to the sagittal plane that is defined, in the illustrated embodiment, by the transverse axis of the rod channel 236 of the monoplanar receiver 200.

Nevertheless, it will also be appreciated that at least the initial engagements between the annular planar top surface 62 of the shank head 60 and the planar underside surfaces 266 of the inner portions 262 of the upper cap structures 260 will not prevent rotation of the shank 50 about its longitudinal axis 52 relative to the lower rocker 250 or to monoplanar receiver 200. In other words, even though the shank 50 shown in FIG. 56 is no longer free to pivot relative to the lower rocker 250, the partial spherical outer surface 64 of the shank head 60, including the discontinuous central portion defined by the crest surfaces of the upper thread 66, is still free to rotate relative the partial spherical lower interior surface 258 of the lower rocker 250 and the discontinuous lower seating surface 210 of the internal cavity 208.

Accordingly, all the internal engagements between the monoplanar receiver 200, the upper insert 270, the lower rocker 250, and the annular planar top surface 62 of the shank head can operate together to limit the pivotal motion of the receiver sub-assembly 13 relative to the shank head 60 to a single plane, while still allowing for complete 360 degree rotation of the monoplanar sub-assembly 13 about the longitudinal axis 52 of the shank 50. In one aspect the single plane of pivotal motion (i.e. the pivot plane) can be aligned with the transverse axis of the rod channel 236. Nevertheless, it is foreseen that in other embodiments the pivot plane of the monoplanar sub-assembly 13 can be modified to fall at any angle relative to the transverse axis of the rod channel 236.

In addition, the pivotal and/or rotational coupling between the shank head 60 and the monoplanar receiver sub-assembly 13 can also comprise a pre-lock non-floppy friction fit that, as described above, can be sufficient to hold the position of the monoplanar receiver sub-assembly 13 relative to the shank head 60 while still allowing for movement of the monoplanar sub-assembly 13 relative to the shank 50 with applied twisting and moment forces. It will be appreciated, moreover, that the mechanical interfaces between the internal components of the monoplanar sub-assembly 13 and the outer surfaces of the shank head 60 that become engaged together to provide the frictional resistance to movement can be different than those described above with the reference to the multiplanar receiver sub-assembly 11.

For example, in one aspect the friction fit that inhibits pivotal motion can be provided by the snap in engagement between the opposed lateral ridges 288 of the insert arms 280 and the shipping state grooves or recesses 229 of the upright arms 236 of the receiver 200, which can serve to compress the underside surfaces of the upper insert 270 against the upper surfaces of the lower rocker 250 sufficient to create frictional engagements between the contact surfaces that inhibit relative pivotal motion between the two components. This can happen before the shank head 60 is uploaded in the monoplanar receiver sub-assembly 13. In another aspect the friction fit that inhibits rotational motion of the shank head 60 can be provided by tight tolerances between the downward-opening partial spherical lower interior surface 258 of the lower rocker 250 and the partial spherical outer surface 64 of the shank head 60, causing the opposed triangularly-shaped downwardly-extending skirt portions 254 of the lower rocker 250 to grip the shank head with a friction fit that inhibits rotational motion between the two components. It is foreseen that other structures and methods may also be used to establish the pre-lock non-floppy friction fit.

Figure 57:
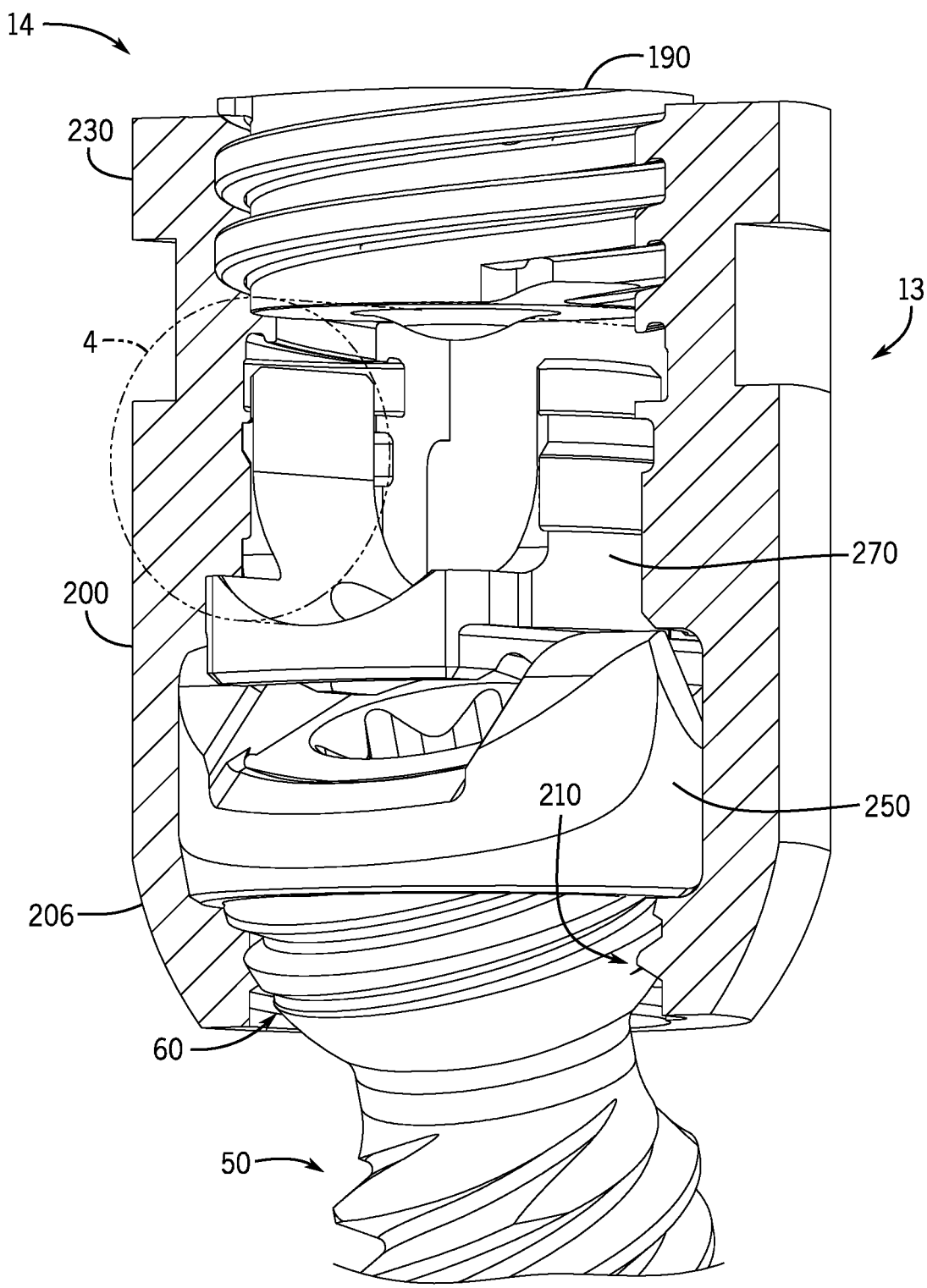
FIG. 57 is a partially cut-away perspective view of the aforementioned monoplanar receiver sub-assembly and shank after assembly together and with the elongate rod and closure of FIG. 45 into a fully assembled and locked monoplanar pivotal bone anchor assembly.

With reference to FIG. 57, upon the monoplanar receiver sub-assembly 13 being coupled to the shank head 60, the same elongate rod 4 described above can be positioned within the rod channel 236 and the same closure 190 can then be threadably or otherwise secured into the rod channel 236 above the elongate rod 4 so as to apply a force or pressure against the upper surface of the elongate rod 4. This force or pressure can be transmitted downward through the elongate rod 4, the upper insert 270 and the lower rocker 250 of the two-piece monoplanar insert, the upper surface portions of the threaded universal shank head 60, and ultimately through to the partial spherical lower seating surface 210 and base portion 206 of the monoplanar receiver 200, thereby locking both the elongate rod 4 and the bone anchor assembly 14 into a final locked position.

With reference to FIGS. 58 and 59-70, illustrated therein is a non-pivotal or monoaxial bone anchor apparatus or assembly 16, in accordance with another representative embodiment of the present disclosure. The non-pivotal bone anchor assembly 16 can include the same bone anchor or implantable shank 50 (see FIG. 59) described above in reference to the multiplanar and monoplanar pivotal bone anchor assemblies that includes, for example, the threaded universal capture portion or shank head 60 with a rounded shape at a proximal end 51, and the shank body 80 extending distally from the threaded head 60 with the anchor portion 84 at a distal end 99 that is configured for securement to the bone. The shank head 60 can further include the same annular planar top surface 62 at an upper end and the discontinuous partial spherical outer surface 64 adjacent the top surface having an upper thread form 66 formed therein. As described above, in one aspect the upper thread form 66 can be a dual lead threadform further comprising a pair of helically wound upper threadforms with crest surfaces defining the discontinuous portions of the partial spherical outer surface 64, with each of the upper threadforms having an upper start structure extending upwards towards the top surface 62 of the shank head 60.

Figure 60:
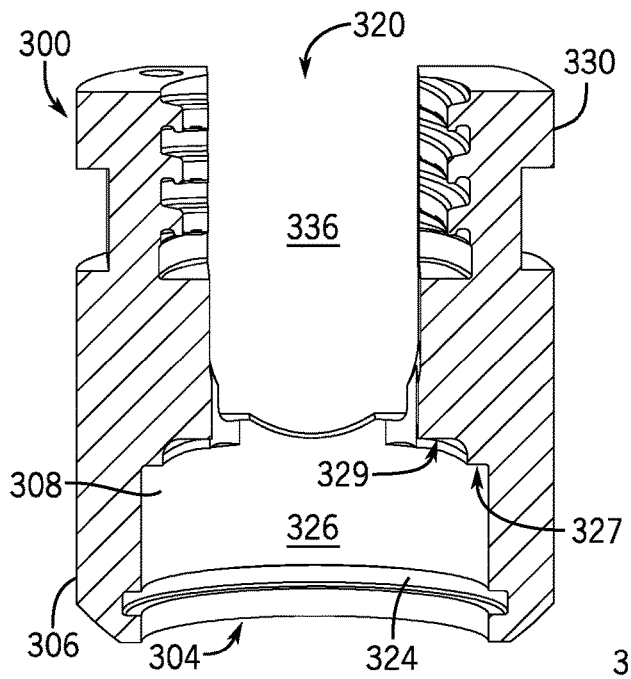
FIG. 60 is a cross-sectional perspective front view of the non-pivotal receiver of FIG. 58.
Figure 61:
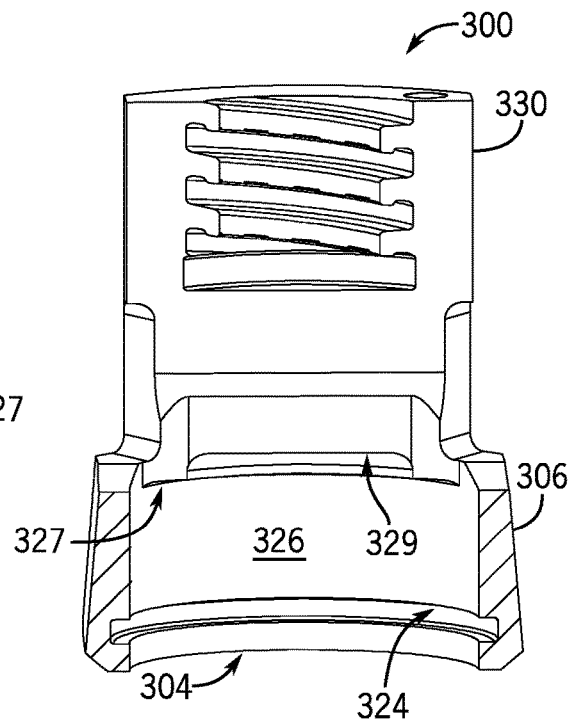
FIG. 61 is a cross-sectional perspective side view of the non-pivotal receiver of FIG. 58.

With reference to FIGS. 58 and 60-61, the non-pivotal embodiment of the bone anchor assembly 16 also includes a receiver 300 having a cylindrical base portion 306 defining an internal cavity 308 portion of a central bore 320, and two upright arms 330 extending upwardly from the base portion 306 to define a rod channel 336 configured for receiving the elongate rod 4. However, while the internal cavity 308 of the non-pivotal receiver 300 also includes a bottom opening 304, it can be distinguishable from the internal cavities of the pivotal embodiments in that the pairs of helically wound lower threadforms formed into rounded lower seating surfaces may be replaced with a straight cylindrical sidewall 326 having a circumferential recess 324 formed therein adjacent to the bottom opening 304. Other features or aspects of the internal cavity 308 of the receiver 300 of the non-pivotal embodiment 16 can be also different than those of the internal cavities of the pivoting embodiments, so as to accommodate a different set of internal components that together form the non-pivotal receiver sub-assembly 15, as described in more detail below.

Figure 62:
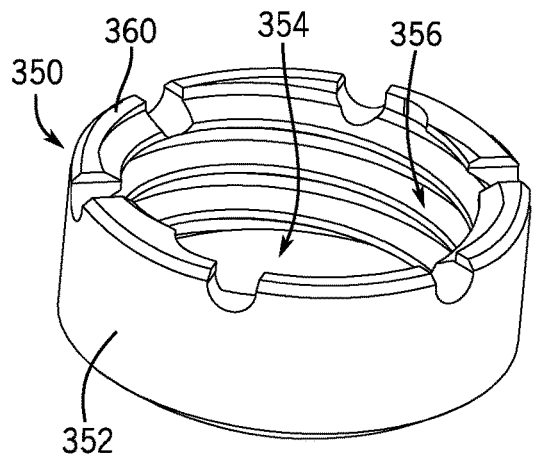
FIG. 62 is an upper perspective view of the rotatable sleeve shown in FIG. 58.
Figure 63:
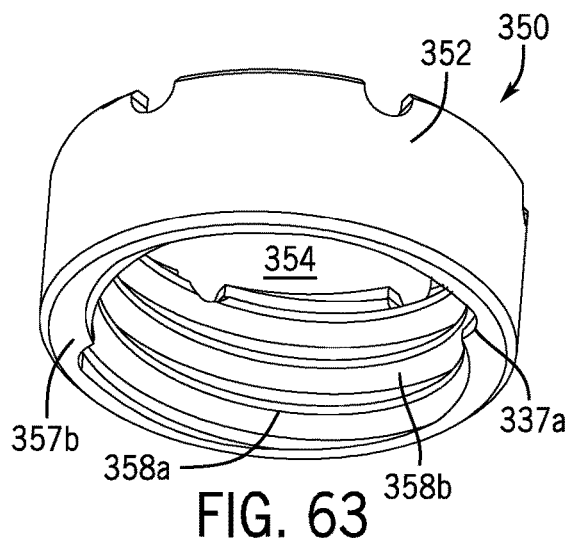
FIG. 63 is an lower perspective view of the rotatable sleeve shown in FIG. 58.
Figure 64:
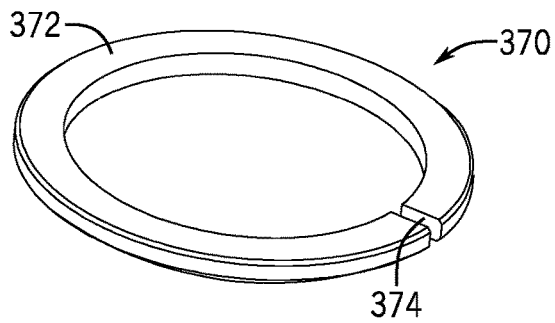
FIG. 64 is an upper perspective view of the snap-in-place retainer shown in FIG. 58.
Figure 65:
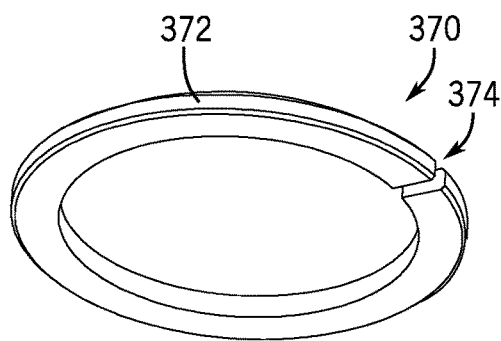
FIG. 65 is an lower perspective view of the snap-in-place retainer shown in FIG. 58.
Figure 66:
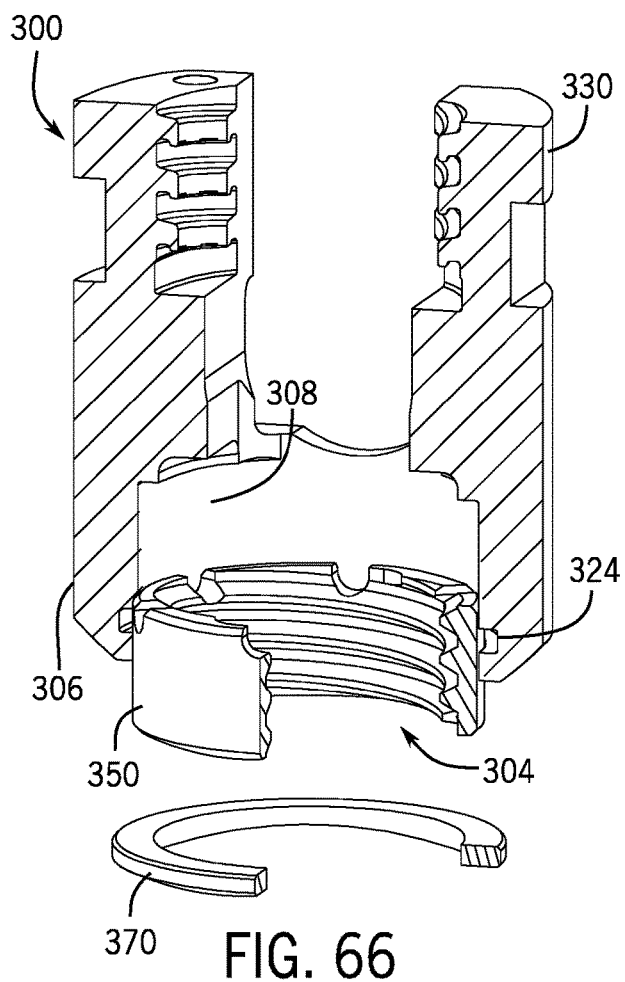
FIG. 66 is a partially cut-away perspective view of the non-pivotal receiver of FIG. 58 during assembly of the rotatable sleeve and snap-in-place retainer into the central bore of the non-pivotal receiver.
Figure 67:
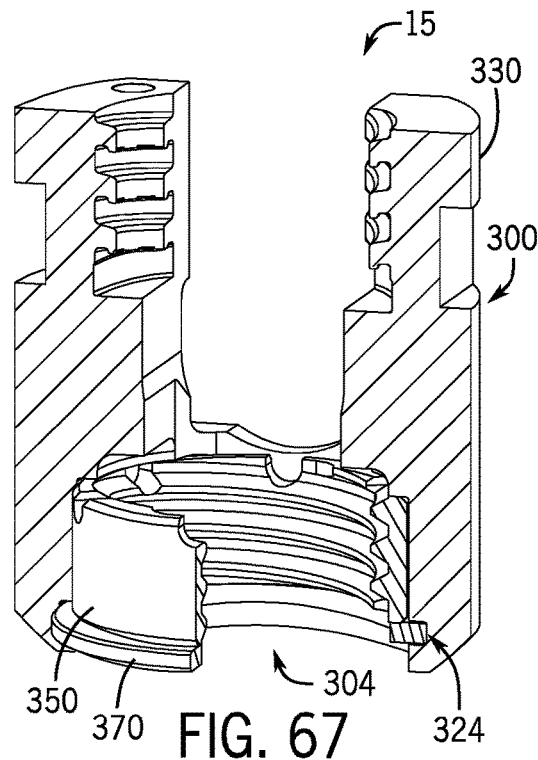
FIG. 67 is a partially cut-away perspective view of the non-pivotal receiver of FIG. 58 after assembly of the rotatable sleeve and snap-in-place retainer into the central bore of the non-pivotal receiver to form the completed non-pivotal receiver sub-assembly.

For example, as shown in FIGS. 58 and 62-63, the non-pivotal receiver sub-assembly 15 can include a rotatable retainer or sleeve 350 having a cylindrical outer surface 352 that is configured to be slidably rotatable within the cylindrical sidewall 326 of the internal cavity 308, and which can be uploaded into the internal cavity 308 through the bottom opening 304 until a top edge surface 360 of the sleeve 350 abuts a downward facing lower discontinuous annular surface 327 that is located near to but below the upper end of the internal cavity 308. The rotatable sleeve 350 generally includes a central aperture 354 with a lower thread form 356 formed into its cylindrical internal surface configured to engage the upper thread form 66 of the threaded universal shank head 60 upon insertion and rotation thereof. Thus, in one aspect the lower thread form 356 can also be a dual lead threadform further comprising helically wound first and second lower threads 358a, 358b having respective first and second lower starts 357a, 357b that are configured to engage with the dual thread/dual lead-in structures of the upper thread form 66 (see FIG. 65).

After the rotatable sleeve 350 is uploaded into the internal cavity, a snap-in-place retainer 370 (FIGS. 64-65) having an open ring body 372 with a slot or gap 374 that allows for radial compression of the retainer 370, can then be uploaded into the internal cavity 308 of the non-pivotal receiver 300 below the rotatable sleeve 350 in a compressed state. The open ring body 372 of the retainer 370 can then be released to snap outward into the circumferential recess 324 at the lower end of the internal cavity 308 so as to prevent the rotatable sleeve 350 from sliding back out the bottom opening 304, as shown in FIGS. 66-76. The rotatable sleeve 350 and the snap-in-place retainer 370 have now been pre-assembled together into the internal cavity 308 of the receiver 300 to form the non-pivotal receiver sub-assembly 15 in a shipping state configuration (FIG. 67), with the threaded central aperture 354 being stabilized and centralized just above or within the bottom opening 304 of the receiver 300 by the snap-in-place retainer 370.

Figure 68:
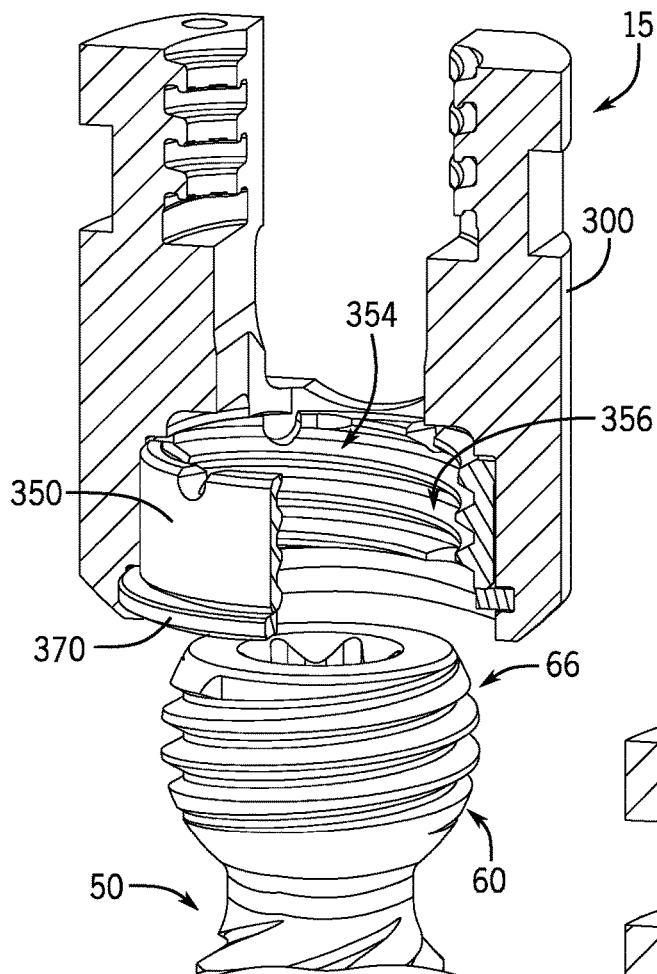
FIG. 68 is a partially cut-away perspective view of the aforementioned non-pivotal receiver sub-assembly and the threaded universal shank head being threadably coupled together.

With reference to FIG. 68, the shank head 60 can then be threadably uploaded into the rotatable sleeve 350 that is itself, in turn, held within internal cavity 308 of the non-pivotal receiver 300 by the snap-in-place retainer 370, so as to become non-pivotably coupled or secured to the non-pivotal receiver sub-assembly 15. In one aspect the rotatable sleeve 350 can be held be temporarily held in angular position relative to the receiver 300 by tooling (not shown) as the shank head 60 is threadably uploaded into the threaded central aperture 354, so as to prevent the rotatable sleeve 350 from rotating within the internal cavity 308 due to the applied torque produced by the engagement of the threads.

Unlike the pivotal embodiments, the upper thread form 66 of the shank head 60 does not clear the lower thread form 356 of the rotatable sleeve 350 upon the completion of the threaded uploading of the shank head 60 into the central aperture 354 of the rotatable sleeve 350, so that the shank head 60 cannot pivot with respect to the sleeve 350. In turn, the rotatable sleeve 350 includes the cylindrical outer surface 352 that is closely or snuggly received within the cylindrical sidewall 326 of the internal cavity 308 of the receiver 300, and which prevents the pivoting of the sleeve 350 (and therefore the shank head 60) with respect to the receiver 300.

Figure 69:
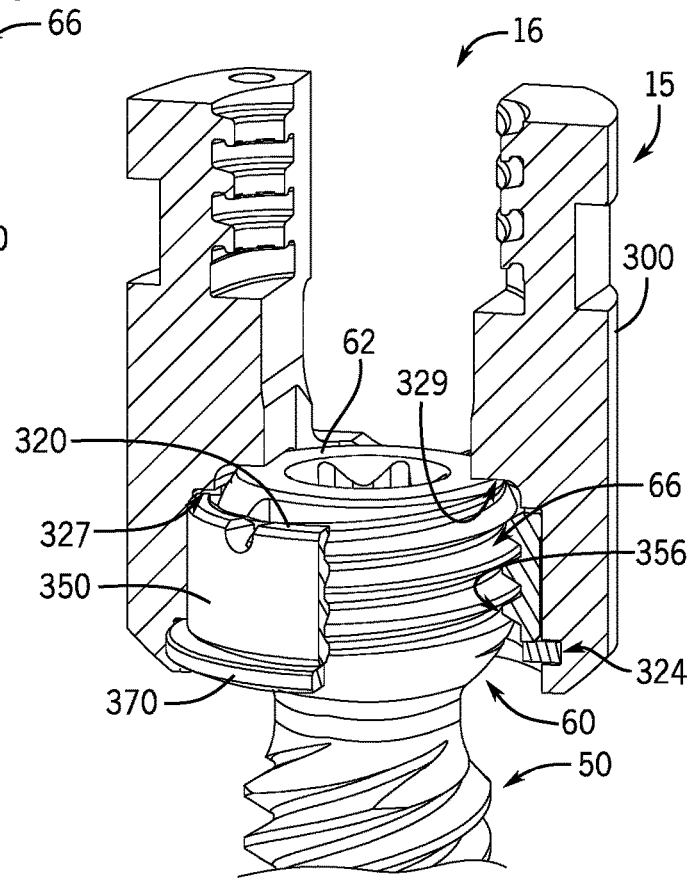
FIG. 69 is a partially cut-away perspective view of the aforementioned non-pivotal receiver sub-assembly and the threaded universal shank head after being threadably coupled together.

With reference to FIG. 69, upon the completion of the threaded uploading of the shank head 60 into the rotatable sleeve 350, the annular planar top surface 62 of the shank head can project above the top edge surface 360 of the sleeve 350 to become engaged with a downward facing upper discontinuous annular surface 329 that can, in turn, define the upper end of the internal cavity 308. As such, an over-torquing of the shank head 60 relative to the rotatable sleeve 350 can then drive the rotatable sleeve 350 downward to bear against snap-in-place retainer 370, which can establish a pre-load that tightly secures the shank head 60 and the rotatable sleeve 350 together. This same pre-loading can also create sliding frictional engagements between the annular planar top surface 62 of the shank head and the upper discontinuous annular surface 329 of the internal cavity. In one aspect these can allow or provide for a complete 360 degree rotation of the non-pivotal sub-assembly 15 about the longitudinal axis 52 of the shank 50 with an applied twisting force.

Figure 70:
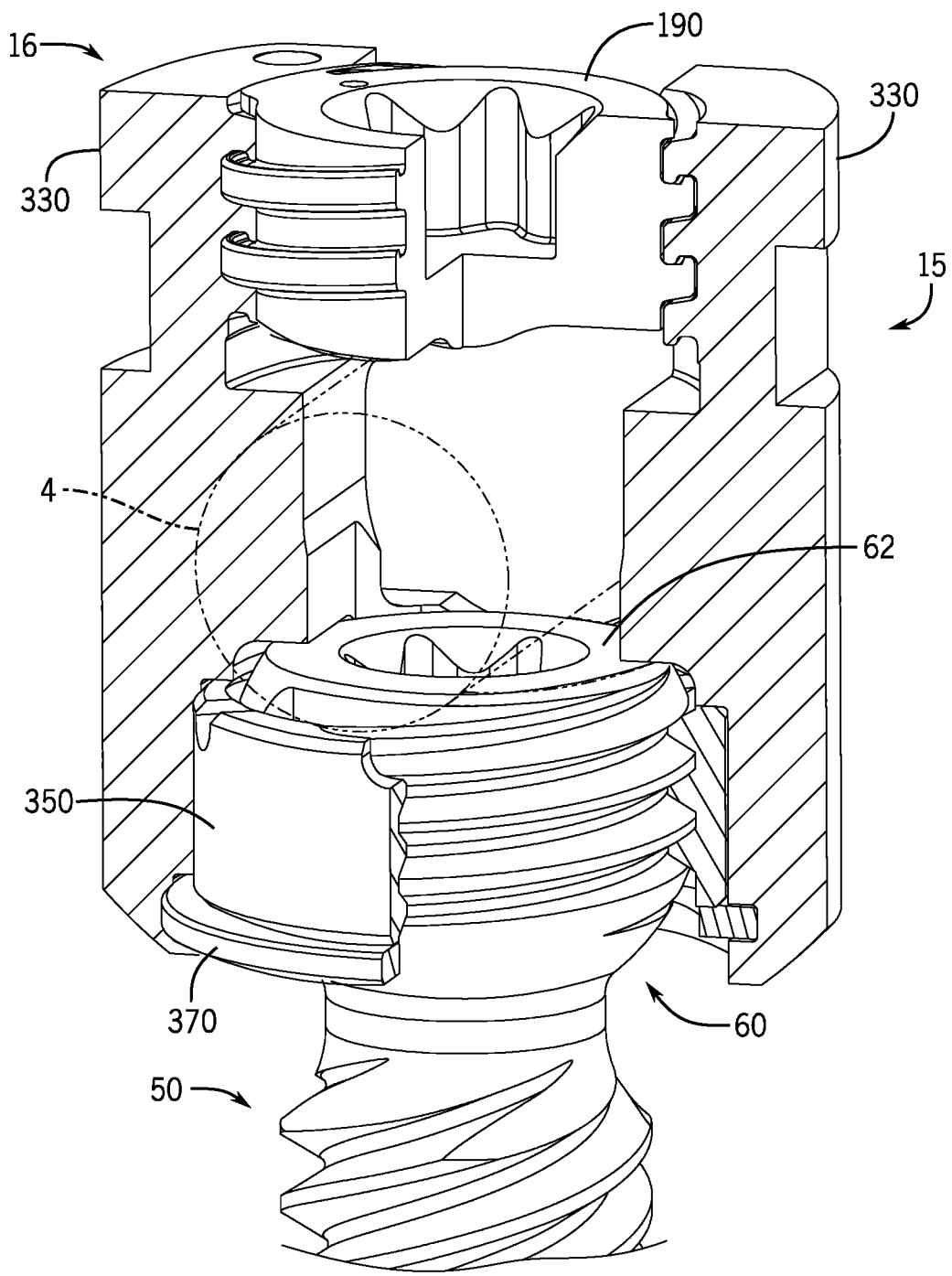
FIG. 70 is a partially cut-away perspective view of the aforementioned non-pivotal receiver sub-assembly and shank after assembly together and with the elongate rod and closure of FIG. 58 into a fully assembled and locked non-pivotal bone anchor assembly.
Figure 75:
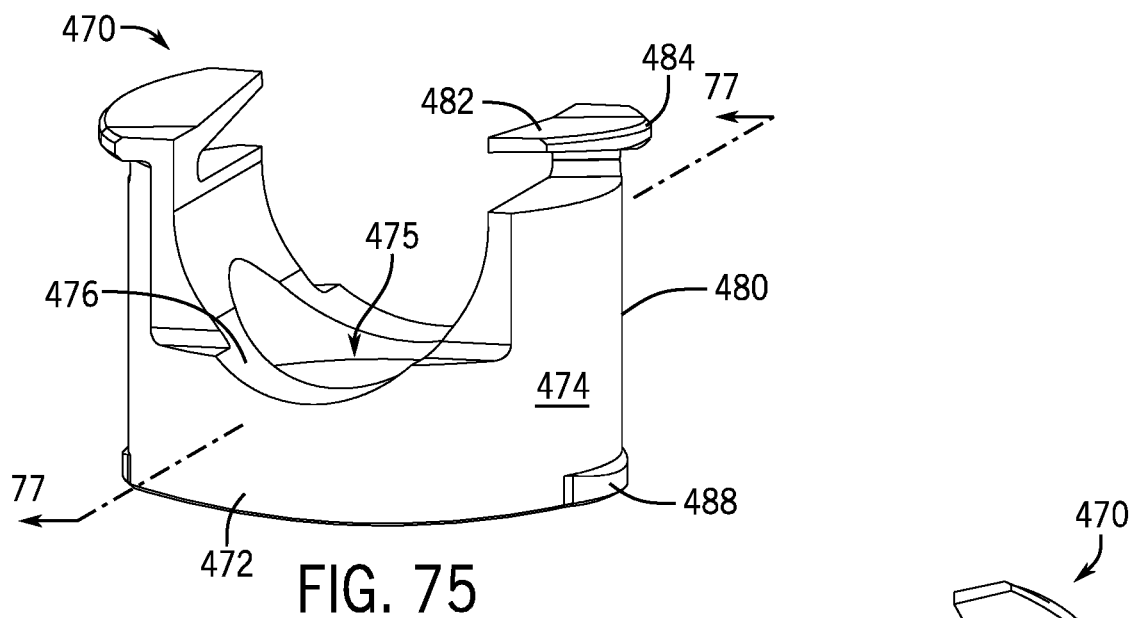
FIG. 75 is an upper perspective view of the multiplanar insert shown in FIG. 72.
Figure 76:
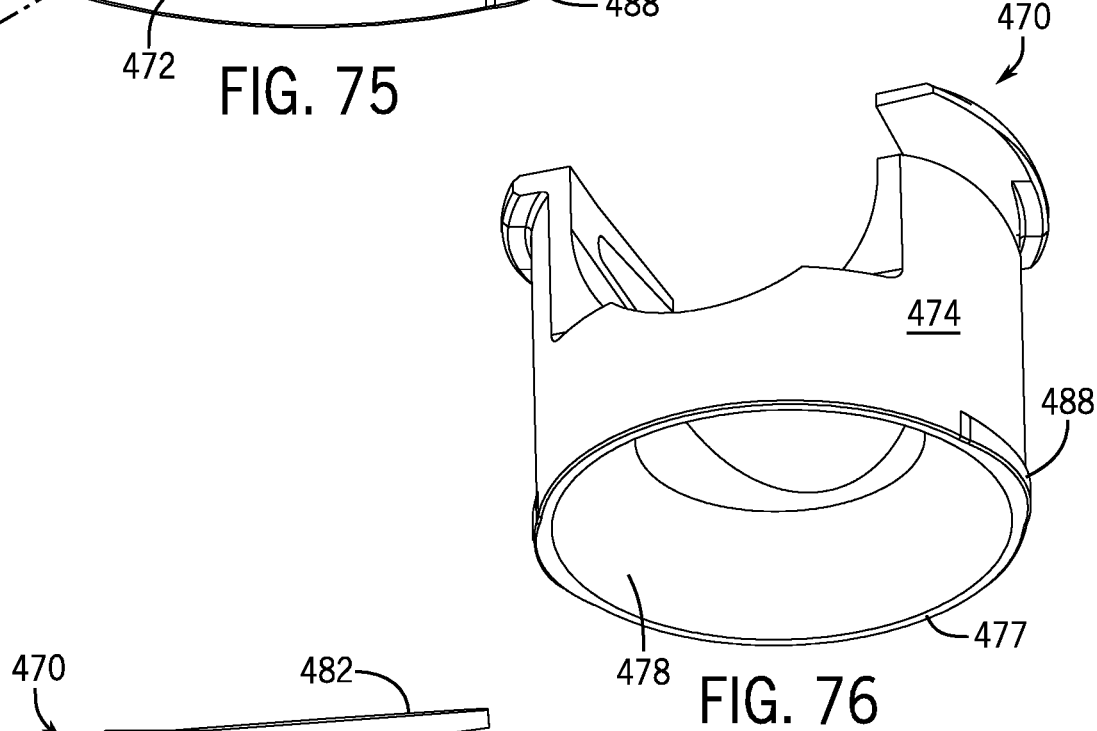
FIG. 76 is a lower perspective view of the multiplanar insert shown in FIG. 72.
Figure 77:
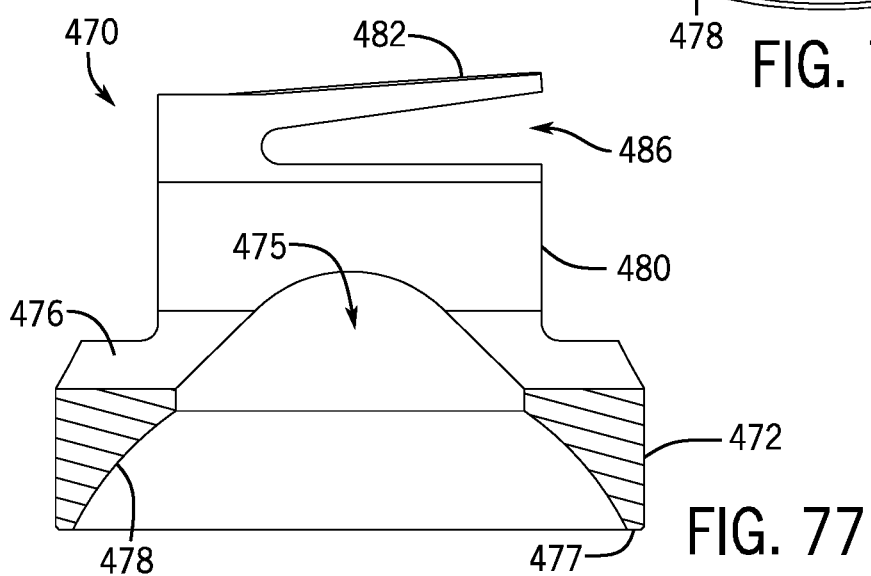
FIG. 77 is a cross-sectional side view of the multiplanar insert shown in FIG. 72.
Figure 78:
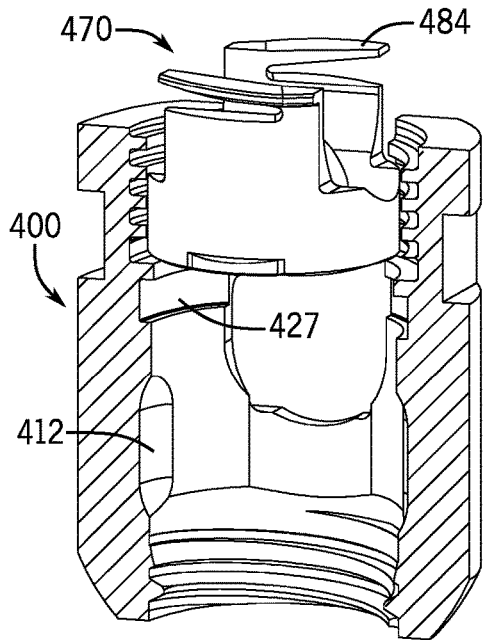
FIG. 78 is a partially cut-away perspective view of the multiplanar receiver and pressure insert of FIG. 72, with the pressure ring being inserted into the axial bore or cavity of the receiver during pre-assembly of the multiplanar receiver sub-assembly.
Figure 79:
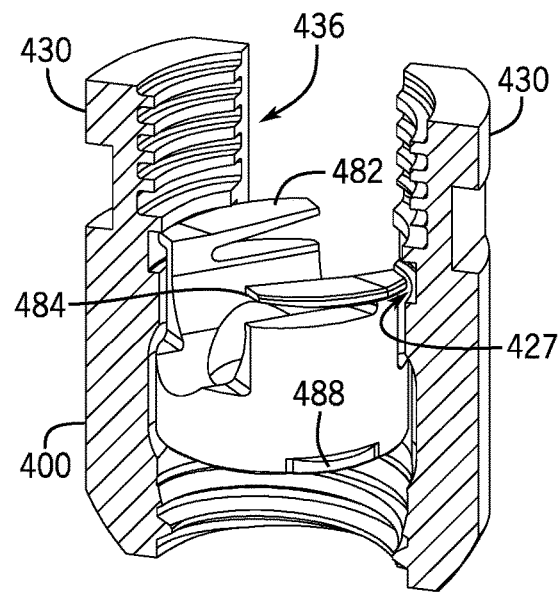
FIG. 79 is a partially cut-away perspective view of the multiplanar receiver and pressure insert of FIG. 78, with the pressure insert being lowered and partially rotated inside the receiver.
Figure 80:
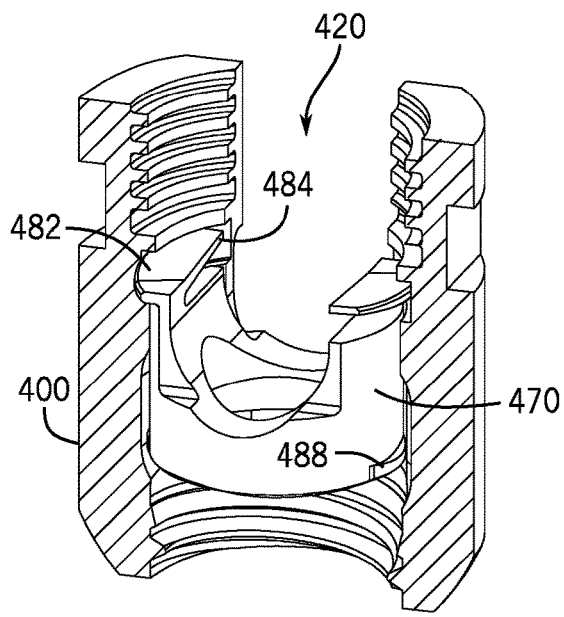
FIG. 80 is a partially cut-away perspective view of the multiplanar receiver and pressure ring of FIG. 78, with the pressure insert being fully rotated inside the receiver to form the pre-assembled multiplanar receiver sub-assembly.

Upon the non-pivotal sub-assembly 15 being coupled to the shank head 60 to form the non-pivotal bone anchor assembly 16, the same elongate rod 4 described above can be positioned within the rod channel 336 and the same closure 190 can then be threadably or otherwise secured into the rod channel 336 above the elongate rod 4 so as to apply a force or pressure against the upper surface of the elongate rod 4. This force or pressure can transmitted downward through the elongate rod 4 and directly onto the planar top surface 62 of the shank head 60, and from there through the shank head, the rotatable sleeve 350, and ultimately through snap-in-place retainer 370 to the cylindrical base portion 306, thereby locking both the elongate rod 4 and the bone anchor assembly 16 into a final locked position, as shown in FIG. 70.

In sum, and with reference back to FIG. 1, the components of the multiplanar 11, monoplanar 13, and non-pivotal 15 receiver sub-assemblies can thus be configured to provide for different degrees of freedom of movement relative to the shank 50 upon the threaded uploading of the same threaded universal shank head 60 into the receiver sub-assembly. In particular, each of the multiplanar 11, monoplanar 13, and non-pivotal 15 receiver sub-assemblies can provide for the complete 360 degree rotation of the sub-assembly about the longitudinal axis 52 of the shank 50 with an applied twisting force, so that the rod channel of the receiver can be aligned with the eventual position of the elongate rod 4 without needing to change the elevation of the threaded shank head 60 relative to the supporting patient bone. While the non-pivotal receiver sub-assembly 15 is limited to this single rotational degree of freedom, both the monoplanar 13 and multiplanar 11 options can additionally provide for the inclination or angulation of the receiver sub-assembly in a single pivot plane or in any pivot plane, respectively, upon the uploading the same threaded universal shank head 60. It will be appreciated that the availability of selecting from the group of multiplanar 11, monoplanar 13, and non-pivotal 15 receiver sub-assemblies for use with the same threadably uploadable universal shank head 60 can serve to establish a modular bone anchor or spinal fixation system that provides the surgeon or medical professional with a greater degree of flexibility for building a more robust and customizable spinal construct, which can result in more individualized and improved outcomes.

It will be further appreciated that the multiple upper starts and threads on the threaded universal shank head 60, in combination with the multiple lower starts and threads formed into the bottom openings of the multiplanar and monoplanar receivers and the non-pivotal rotatable sleeves, can advantageously provide for a quicker (e.g. fewer turns) and a more reliable (e.g. less chance of cross-threading) coupling of the receiver sub-assemblies with the threaded universal shank head 60 in the surgical environment. In some aspects the threaded configuration can also provide for a quick disassembly of the bone anchor assemblies, simply by aligning the vertical centerline axis of the receiver sub-assembly with the longitudinal axis 52 of the shank 50 and rotating the receiver sub-assemblies in a reverse direction until the lower and upper threadforms become re-engaged and the receiver sub-assembly can be threadably rotated upwards off the shank head 60.

Furthermore, the multiple lower starts and threads can also serve as bone debris cleaners of the multiple upper threads on the threaded universal shank head 60 during the uploading of the shank head into the receiver sub-assembly, ensuring that the various engagement interfaces between the fully assembled components within the internal cavities of the receivers are smooth and continuous and uninterrupted by bone debris or soft tissue.

Illustrated in FIG. 71 is another representative embodiment of a modular spinal fixation system 20 that includes a plurality of bone attachment structures 50, such as a shanks or bone screws, with each having a threaded universal shank head 60 that is similar or even identical to the threaded universal shank heads described above. The threaded universal shank heads 60 are generally configured for uploading by threadable rotation into either a multiplanar receiver sub-assembly 21, a monoplanar receiver sub-assembly 23, or a non-pivotal receiver sub-assembly 25 that are also similar in function and in many structures to the receiver sub-assemblies described above, with the exception that each of the different types of receiver sub-assemblies is further configured to provide an automatic or self-engaging pre-lock friction fit feature that can be established while avoiding the use of insert tool deployment or additional tooling. In other words, the pre-lock friction fit can be established simply by threadably coupling any of the above-described receiver sub-assemblies 21, 23, 25 onto the threaded universal shank head 60. Furthermore, and as described in detail below, establishing the pre-lock friction fit between the threaded universal shank head 60 can be accomplished in a number of different ways.

For example, with reference to FIGS. 72 and 73-85, illustrated therein is a multiplanar bone anchor assembly 22 having an axially-biased, automatic or self-engaging pre-lock friction fit, in accordance with another representative embodiment of the present disclosure. The multiplanar bone anchor assembly 22 can include the same bone anchor or implantable shank 50 having the threaded universal capture portion or shank head 60 with a rounded shape at a proximal end 51, and the shank body 80 extending distally from the threaded head 60 with the anchor portion 84 at a distal end 99 that is configured for securement to the bone.

The shank head 60 can further include the same annular planar top surface 62 at an upper end and the discontinuous partial spherical outer surface 64 adjacent the top surface having an upper thread form 66 formed therein. As described above, in one aspect the upper thread form 66 can be a dual lead threadform further comprising a pair of helically wound upper threadforms with crest surfaces defining the discontinuous portions of the partial spherical outer surface 64, with each of the upper threadforms having an upper start structure extending upwards towards the top surface 62 of the shank head 60.

As shown in FIGS. 72-74, the multiplanar bone anchor assembly 22 includes a multiplanar receiver 400 having a cylindrical base portion 406 defining an internal cavity 408 portion of a central bore, and two upright arms 430 extending upwardly from the base portion 406 to define a rod channel 436 configured for receiving the elongate rod 4. The internal cavity 408 of the multiplanar receiver 400 also includes a bottom opening 404 and a lower seating surface 410 that is configured to receive and support the threaded universal head 60 of the shank 50 within a lower portion of the internal cavity 408 of the multiplanar receiver 400. The lower seating surface 410 generally comprises a discontinuous partial spherical surface curving downward and inward from a transition edge to the bottom opening 404 that opens onto the bottom surface 402 of the multiplanar receiver 400, and having a lower thread form 412 formed therein. In particular, the lower thread form 412 is configured to engage the upper thread form 66 of the threaded universal shank head 60 upon insertion and rotation thereof. Therefore, in one aspect the lower thread form 412 can also be a dual lead threadform further comprising helically wound first and second lower threads 414*a*, 414*b* having respective first and second lower starts 413*a*, 413*b* that are configured to engage with the dual thread/dual lead-in structures of the upper thread form 66.

Other features of the multiplanar receiver 400 can be similar or even identical to the corresponding features of the multiplanar receiver 100 described above, with the exception that the inner surfaces of the upright arms 430 can be modified, in part, to include a discontinuous inner recess 427 defined by a downward-facing upper arcuate surface 429 and an upward-facing lower arcuate surface 425, and the internal cavity 408 can be modified, in part, to include opposed vertical pockets 422 formed into the cylindrical sidewall 426 of the central bore 420 that defines the upper portion of the internal cavity 408 above the discontinuous partial spherical lower seating surface 410.

As shown in FIGS. 72 and 75-77, the multiplanar bone anchor assembly 22 can further include a multiplanar insert 470 that can be pre-assembled into the rod channel 436 and internal cavity 408 of the multiplanar receiver 400 to form the multiplanar receiver sub-assembly 21, after which the threaded universal shank head 60 of the shank 50 can be threadably uploaded into the internal cavity 408 and pivotably coupled or secured to the multiplanar receiver sub-assembly 21 to form the multiplanar bone anchor assembly 22.

The multiplanar insert 470 can differ from the multiplanar pressure ring 170 described above, in that the insert 470 includes a lower base portion 472 with two insert arms 480 extending upward from the lower base portion 472, with the base portion 472 and insert arms 480 together defining a cylindrical outer surface 474 that is sized to be slidably received within the central bore 420 of the multiplanar receiver 400. The multiplanar insert 470 includes a upward-facing curved saddle surface 476 extending between the insert arms 480 that is engageable with the elongate rod, and a downwardly-opening concave partial spherical lower surface 478, extending upward and inward from an annular lower bottom edge 477, that is engageable with the discontinuous partial spherical outer surface 64 of the threaded universal shank head 60. The multiplanar insert 470 further includes a central tool-receiving aperture 475 defined by an inner cylindrical surface that configured to slidably receive a drive tool (not shown) that extends downwardly through the central bore 420 of the multiplanar receiver 400 to engage the internal drive socket 54 formed into the top end 51 of the threaded universal shank head 60.

The insert arms 480 can include integral flanges 484 that project radially outward from the top portions of the insert upright arms 480 and having top surfaces 482 that are configured to rotate under the downward-facing upper arcuate surfaces 429 of the discontinuous recess 427 formed into the central bore 420 of the multiplanar receiver 400. In one aspect the flanges 484 can further comprise integral upwardly-angled spring-like structures, with the top surfaces 482 being configured to resiliently engage with the downward-facing upper arcuate surfaces 429 of the discontinuous recess 427 so as to provide a downwardly-directed force that biases the multiplanar insert 470 against the discontinuous partial spherical outer surface 64 of the threaded universal shank head 60. In one aspect this modification can include forming a slot 486 extending inward from the trailing edge of the insert upright arms 480 and just below the radially projecting flanges 484, and then bending the trailing end of each flange upward to form the upwardly-angled spring-like structures.

The multiplanar insert 470 may additionally include an indexing structure configured to releasably engage with a complementary indexing structure formed into the central bore 420 of the multiplanar receiver 400, upon rotation of the insert about the receiver vertical centerline axis, so as to inhibit further rotation of the insert out of its rotated position. For example, in one embodiment the indexing structure of the insert can comprise opposite outwardly projecting nubs or protuberances 488 located near the lower bottom edge 477 of the base portion 472 or higher up along the side of the insert that releasably engage with the opposed vertical side pockets 422 formed into the central bore 420 of the multiplanar receiver 400 upon rotation of the multiplanar insert 220 into its rotated position. It is foreseen that other structures can be used to hold the insert relative to the receiver, such as crimps, pegs, set screws or separate rings, to inhibit rotational movement and/or to control translational movement of the insert along the vertical axis of the receiver, and that the insert could be snapped in place, or otherwise positioned, within the receiver.

As shown in FIGS. 78-81, for example, the multiplanar insert 470 can be downloaded through the rod channel 438 and central bore 420 of the multiplanar receiver 400 and then rotated, up to and through about a 90 degree range (approximately ¼ turn) around the vertical centerline axis of the receiver 400, with the outwardly-projecting flanges 484 rotating into a center portion of the recess 427 so that the top surfaces 482 of the flanges 484 are aligned with the downward-facing upper arcuate surfaces 429 of the recess 427 and the outwardly projecting nubs 488 are rotated into the opposed vertical side pockets 422 formed into the central bore 420 to prevent further rotation of the insert 470 relative to the receiver 400.

Figure 81:
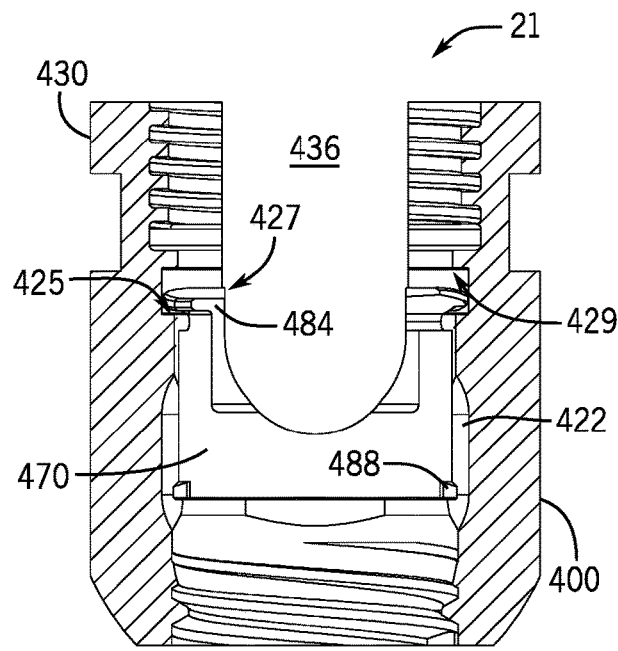
FIG. 81 is a cross-sectional side view of the multiplanar receiver sub-assembly of FIG. 80.

With reference to FIG. 81, the multiplanar insert 470 is now captured and secured within the receiver 400 to form the multiplanar receiver sub-assembly 21 in the pre-assembled shipping state position. It will be appreciated that with the multiplanar receiver sub-assembly 21 in a vertical orientation, as shown in the drawing, the force of gravity will cause the multiplanar insert 470 to drop downward until the underside surfaces of the outwardly-projecting flanges 484 rest on the upward-facing lower arcuate surface 425 of the recess 427, with the top surfaces 482 being spaced below the downward-facing upper arcuate surfaces 429. The pre-assembly of the multiplanar receiver sub-assembly 21 is now complete, which receiver sub-assembly 21 is ready for storage and/or shipping and handling, and for eventually attachment to the threaded head 60 of the shank 50 or bone anchor either prior to or during spinal surgery.

Figure 83:
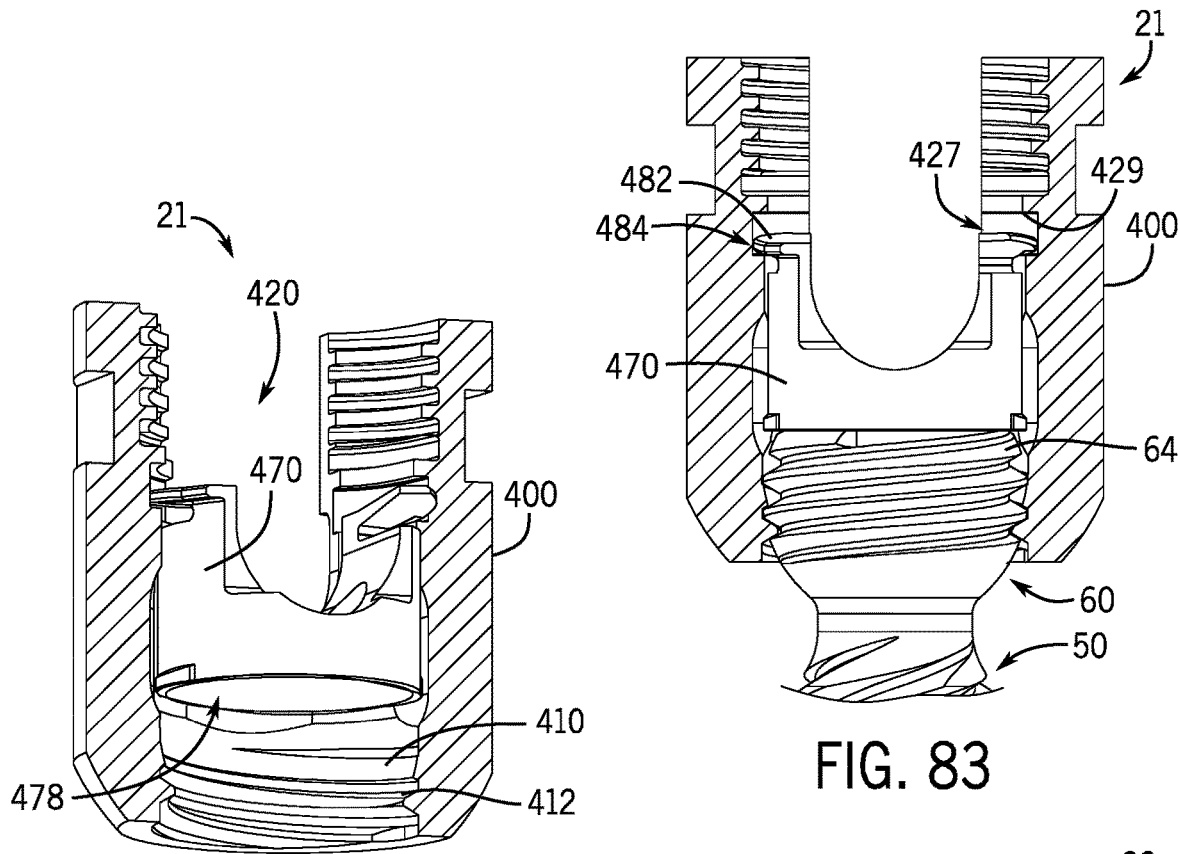
FIG. 83 is another partially cut-away perspective view of the aforementioned multiplanar receiver sub-assembly and shank, with the shank head being further threadably uploaded into the receiver until the shank head engages the partial spherical lower surface of the pressure insert.
Figure 82:
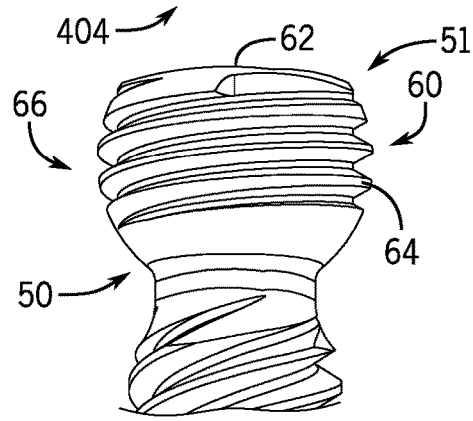
FIG. 82 is a partially cut-away perspective view of the aforementioned multiplanar receiver sub-assembly and shank, with the shank head being partially threadably uploaded into the receiver.
Figure 84:
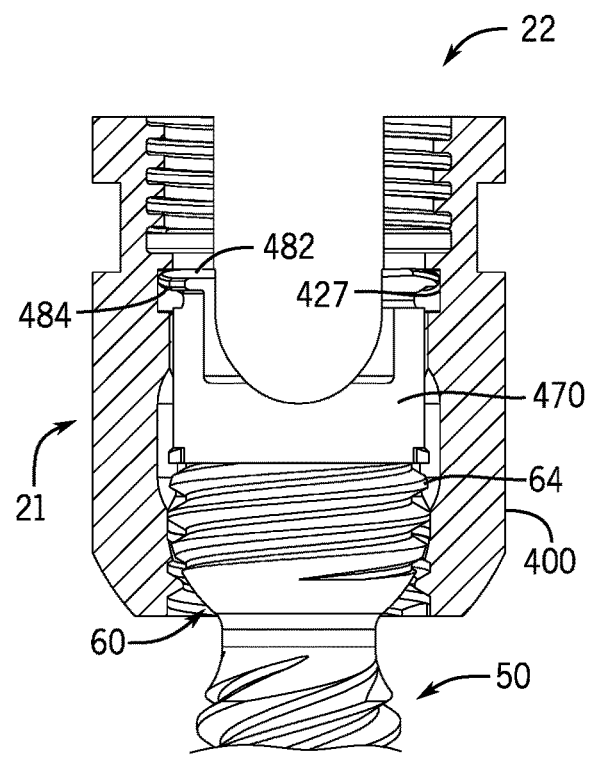
FIG. 84 is a partially cut-away perspective view of the aforementioned multiplanar receiver sub-assembly and shank, with the shank head being fully threadably uploaded to the cavity of the receiver to force the pressure ring upwards from the shipping state position to a friction fit position, prior to and in preparation for installing the elongate rod and closure.

As shown in FIG. 82, the multiplanar receiver sub-assembly 21 can be positioned above the proximal end 51 of the shank 50 or bone anchor with the vertical centerline axis of the receiver 400 being substantially co-linear with the longitudinal axis of the shank. The multiplanar receiver sub-assembly 21 is then moved downward (or the shank 50 is moved upward, depending on the frame of reference of the reader) under rotation until the top surface 62 of the shank head 60 begins to enter the bottom opening 404 of the receiver 400 and the lower thread form 412 becomes engaged with the upper thread form 66 of the shank head 60. The multiplanar receiver sub-assembly 21 can continue to be freely threadably advanced under rotation onto the shank head 60 until the upper portion of the discontinuous partial spherical outer surface 64 of the shank head 60 engages the partial spherical lower surface 478 of the multiplanar insert 470 that is secured in its pre-assembled shipping state position in the center of the central bore 420, as shown in FIG. 83.

After reaching this initial contact position, further threaded advancement of the multiplanar receiver sub-assembly 21 under rotation onto the shank head 60 will also then drive or thrust the multiplanar insert 470 upward with the internal cavity 108 until the top surfaces 482 of the outwardly-projecting flanges 484 become engaged with the downward-facing upper arcuate surfaces 429 of the discontinuous recess 427. Continued threaded advancement of the multiplanar receiver sub-assembly 21 under rotation onto the shank head 60 will cause the outwardly-projecting flanges 484 to resiliently deflect and create a downwardly-directed resistance or axially biasing force that presses downward on the threaded universal shank head 60 even as the shank head continues to advance upward into the internal cavity 408 and shortly thereafter clear and release from the lower thread form 412 of the receiver, thereby becoming pivotably coupled or secured to the multiplanar receiver sub-assembly 21. The downwardly-directed resistance force is maintained after the threaded engagement is released, and can serve to automatically establish a pre-lock friction fit without any further manipulation or deployment of the multiplanar insert 470 with tooling. It will be appreciated that the resistance or axially biasing force and thereby the strength of the pre-lock friction fit can be controlled by adjusting the shape, thickness, and upward curvature of the outwardly-projecting flanges 484.

Figure 85:
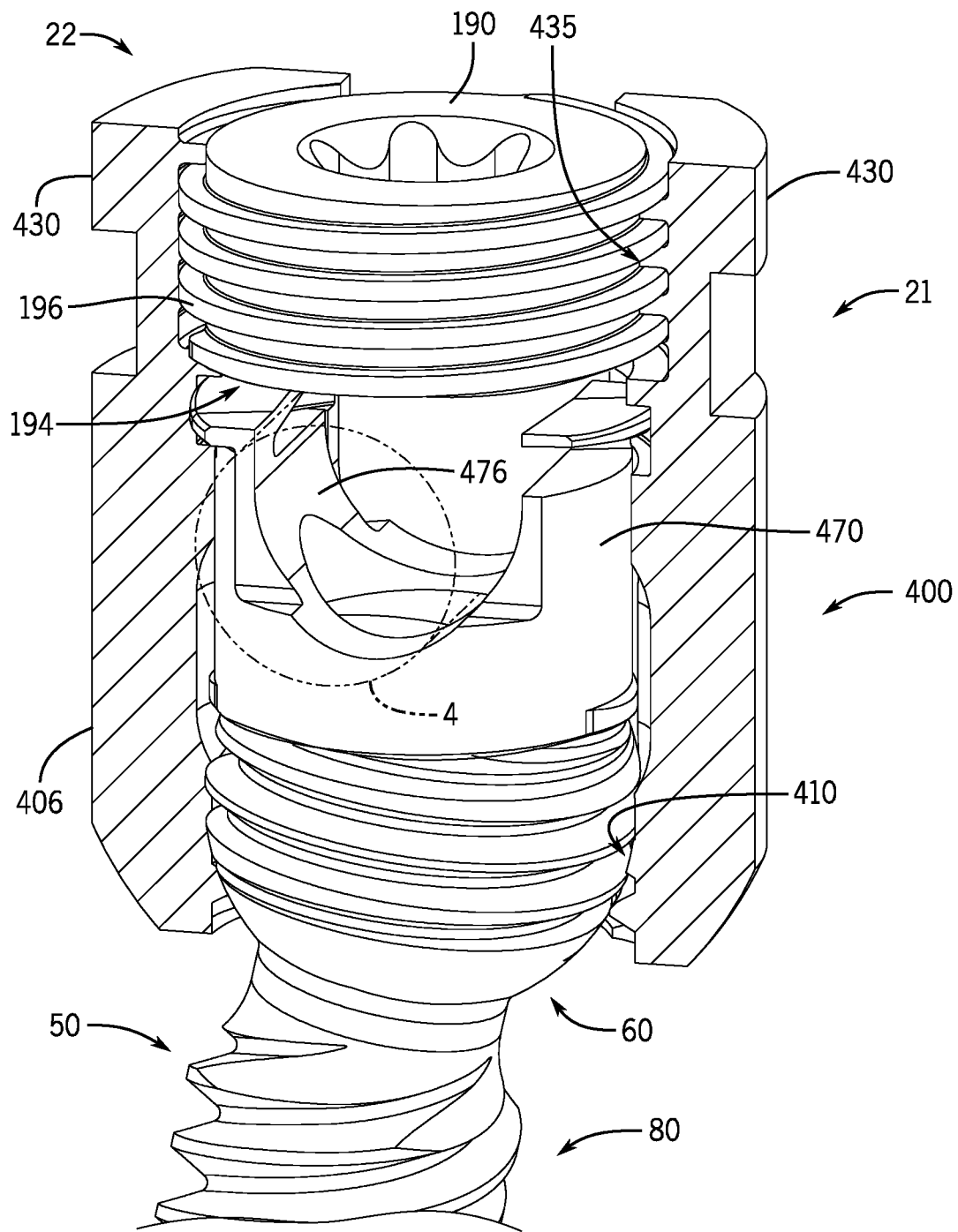
FIG. 85 is a partially cut-away perspective view of the aforementioned multiplanar receiver sub-assembly and shank after assembly together and with the elongate rod and closure of FIG. 72 into a fully assembled and locked multiplanar pivotal bone anchor assembly.
Figure 86:
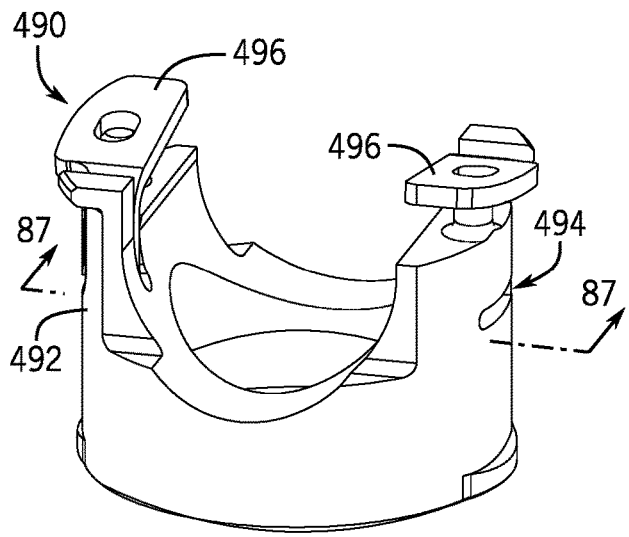
FIG. 86 is an upper perspective view of one alternative embodiment of the multiplanar insert shown in FIG. 72.
Figure 87:
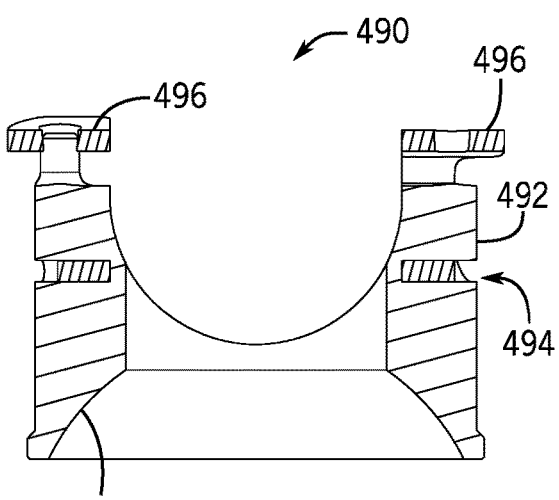
FIG. 87 is a cross-sectional side view of the multiplanar insert shown in FIG. 86.
Figure 88:
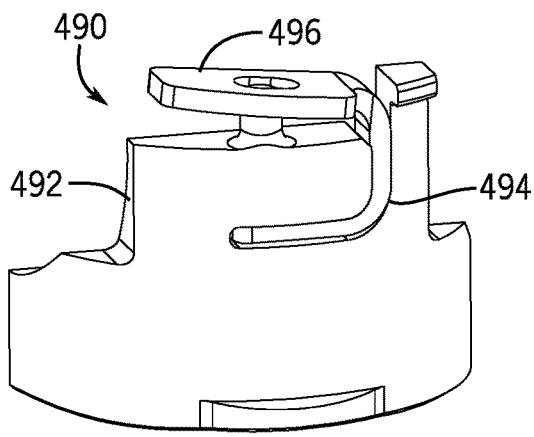
FIG. 88 is a side perspective view of the multiplanar insert shown in FIG. 86.
Figure 89:
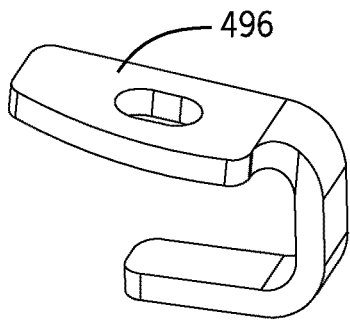
FIG. 89 is a side perspective view a spring element included with the multiplanar insert shown in FIG. 86.
Figure 93:
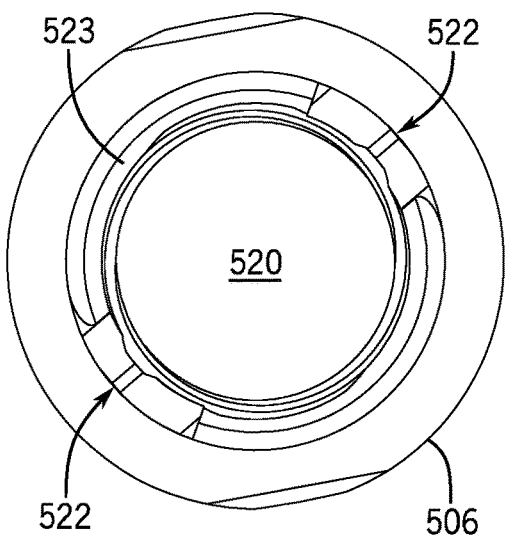
FIG. 93 is a cross-sectional top view of the monoplanar receiver of FIG. 90.
Figure 94:
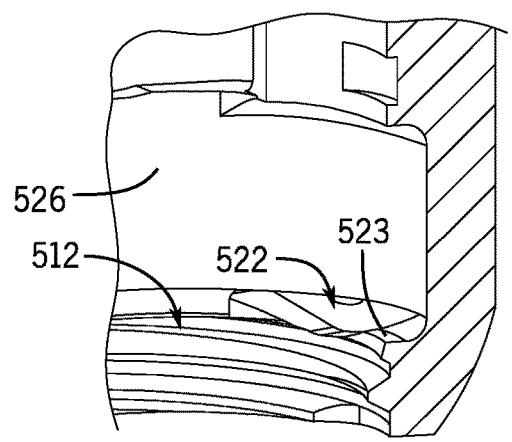
FIG. 94 is a close-up cross-sectional perspective view of the upward-facing triangular divots formed into the internal cavity of the monoplanar receiver of FIG. 90.
Figure 95:
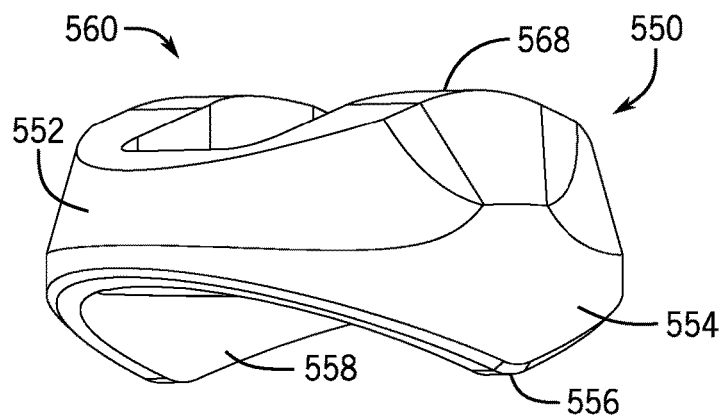
FIG. 95 is an side perspective view of the lower turret piece of the monoplanar insert shown in FIG. 90.
Figure 96:
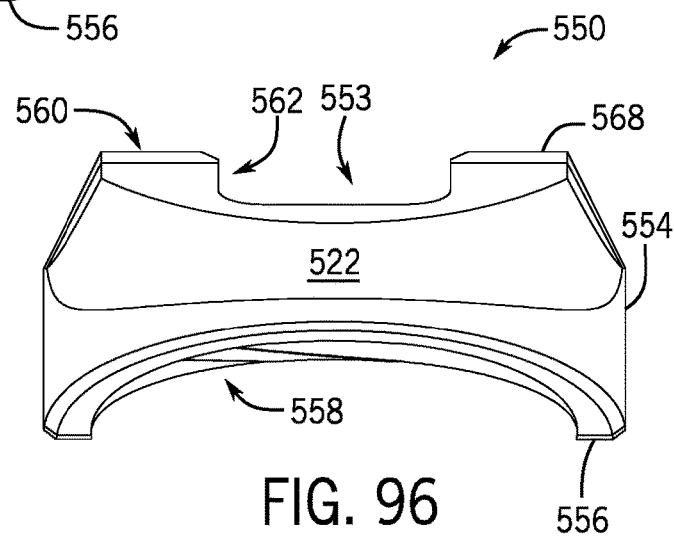
FIG. 96 is a front view of the lower turret piece of the monoplanar insert shown in FIG. 90.
Figure 97:
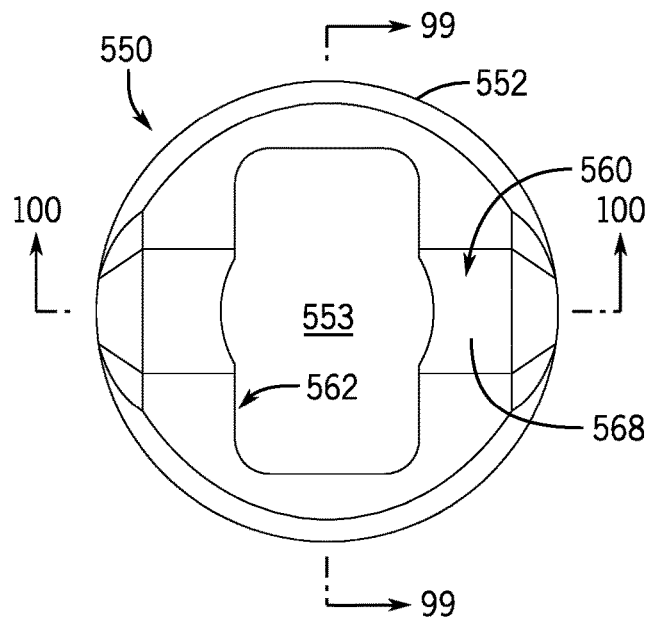
FIG. 97 is a top view of the lower turret piece of the monoplanar insert shown in FIG. 90.
Figure 98:
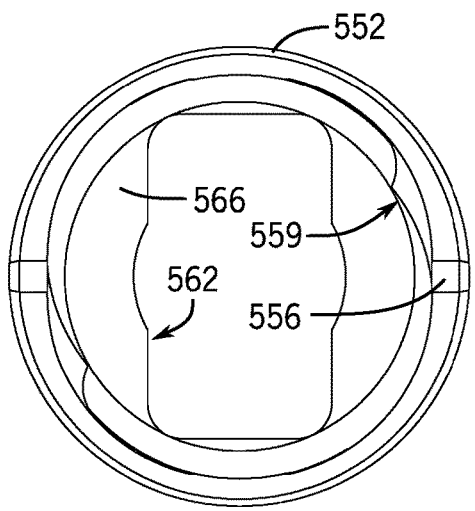
FIG. 98 is a bottom view of the lower turret piece of the monoplanar insert shown in FIG. 90.
Figure 99:
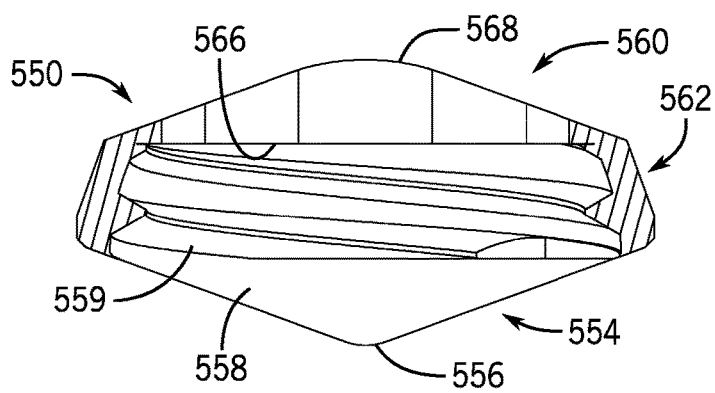
FIG. 99 is a cross-sectional side view of the lower turret piece of the monoplanar insert shown in FIG. 90.
Figure 100:
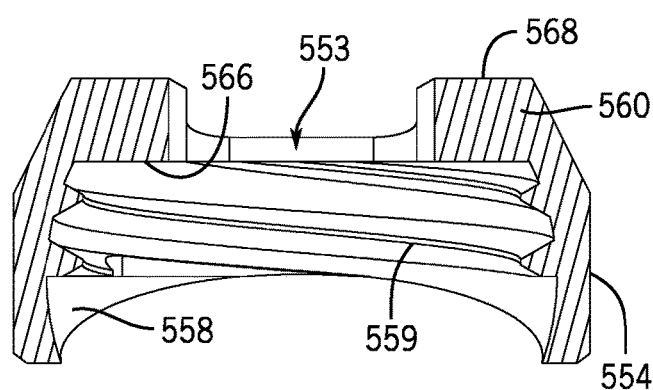
FIG. 100 is a cross-sectional front view of the lower turret piece of the monoplanar insert shown in FIG. 90.

Illustrated in FIG. 85 is the multiplanar pivotal bone anchor assembly 22 as fully assembled and locked with the elongate rod 4 and the single-piece closure 190. For instance, after a desired alignment of the rod channel of the receiver 400 has been achieved via manipulation of the multiplanar receiver sub-assembly 21 relative to the shank head 60, with the axially biased multiplanar insert 470 providing a pre-lock friction fit, the elongate rod 4 can be installed (i.e. reduced) into the rod channel 436, such as with instruments and/or breakoff extensions on the upright arms 430, until the lowermost or underside surface of the elongate rod 4 approaches the upward-facing curved saddle surface 476 of the insert 470. The closure 190 can then be installed into the upper portion of the central bore 420 of the receiver 400 (or breakoff extensions), in which the outer continuous guide and advancement structure 196 of the closure 190 rotatably engages the discontinuous guide and advancement structure 435 formed into the interior faces of the receiver upright arms 130 (and breakoff extensions). The closure 190 can be threaded downwardly until the bottom surface 194 of the closure 190, or the downwardly-projecting central projection 195 protruding therefrom, engages the top surface of the elongate rod 4. Further rotation and torquing of the closure 190 can then be used to drive the elongate rod 4 downward onto the multiplanar insert 470, which in turn further drives the shank head 60 downward onto the threaded or discontinuous partial spherical lower seating surface 410 of the internal cavity 408 of the receiver 400 to achieve a final locking of the multiplanar bone anchor assembly 22, in which the multiplanar receiver sub-assembly 21 can no longer pivot or rotate relative to the shank 50.

Illustrated in FIGS. 86-89 is another representative embodiment of an axially-biasing multiplanar insert 490 for use in the multiplanar bone anchor assembly 22. For this embodiment of the multiplanar insert 490, the integral flanges that project radially outwardly and upwardly from the top portions of the insert upright arms from the previous embodiment 470 can be replaced with separate U-shaped spring elements 496 that are secured within complementary recesses 494 formed into the upper ends of the insert arms 492. The spring elements 496 can also become positioned within the discontinuous inner recess 427 of the upright arms 430 upon rotation of the multiplanar insert 490 within the central bore of the multiplanar receiver 400, so as to provide the downwardly-directed biasing force on the capture portion of the bone anchor (not shown) and thereby establish a biased frictional engagement between the concave lower surface of the pressure insert 497 and the upper curvate section of the capture portion that can resist the rotational movement of the shank relative to the receiver 400. The remaining structural elements of the multiplanar insert 490 and its interactions with the multiplanar receiver 400 can be the same as or similar to the structural elements of the multiplanar insert 470 discussed above.

With reference to FIGS. 90 and 91-112, illustrated therein is a monoplanar bone anchor assembly 24 having an axially-biased, automatic or self-engaging friction fit, in accordance with another representative embodiment of the present disclosure. The monoplanar bone anchor assembly 24 can include the same bone anchor or implantable shank 50 having the threaded universal capture portion or shank head 60 with a rounded shape at a proximal end 51, and the shank body 80 extending distally from the threaded head 60 with the anchor portion 84 at a distal end 99 that is configured for securement to the bone. The shank head 60 can further include the same annular planar top surface 62 at an upper end and the discontinuous partial spherical outer surface 64 adjacent the top surface having an upper thread form 66 formed therein. As described above, in one aspect the upper thread form 66 can be a dual lead threadform further comprising a pair of helically wound upper threadforms with crest surfaces defining the discontinuous portions of the partial spherical outer surface 64, with each of the upper threadforms having an upper start structure extending upwards towards the top surface 62 of the shank head 60.

The monoplanar bone anchor assembly 24 includes a monoplanar receiver 500 having a cylindrical base portion 506 defining an internal cavity 508 portion of a central bore 520, and two upright arms 530 extending upwardly from the base portion 506 to define a rod channel 536 configured for receiving the elongate rod. With reference to FIGS. 91-92, the internal cavity 508 can further include a bottom opening 504 and a lower seating surface 510 that is configured to receive and support the threaded universal head 60 of the shank 50 within a lower portion of the internal cavity 508 of the monoplanar receiver 500. The lower seating surface 510 generally comprises a discontinuous partial spherical surface curving downward and inward from a transition edge to the bottom opening 504 that opens onto the bottom surface 502 of the monoplanar receiver 500, and having a lower thread form 512 formed therein. It is understood that the lower thread form 512 can be similar to the corresponding lower thread forms of the pivotal receivers described above so as to be threadably mateable with the same threaded universal shank head 60 upon insertion and rotation thereof.

Many elements of the monoplanar receiver 500 can be similar to the corresponding elements of the monoplanar receiver 200 described above, with the exception that the inner surfaces of the upright arms 530 can be modified, in part, to replace the shipping state groove with a somewhat larger discontinuous inner recess 527 defined by a downward-facing upper arcuate surface 529 and an upward-facing lower arcuate surface 525 and by forming opposed pockets 524 into the inwardly-facing discontinuous upper cylindrical surface 528 that extends downward from the guide and advancement structure 535 toward the internal cavity 508. The internal cavity can also modified, in part, to add opposed upward-facing triangular recesses or divots 522 into the upward-facing annular step surface 523 that extends between the lower cylindrical surface 526 and the circular transition edge demarking the transition to the discontinuous lower seating surface 510 (see also FIGS. 92-94).

The monoplanar bone anchor assembly 24 can also include a multi-piece monoplanar insert, such as a two-piece monoplanar insert comprising a rod-receiving axially-biasing upper insert 570 and a shank-engaging lower turret 550, which axially-biasing upper insert 570 and lower turret 550 can be pre-assembled together into the central bore 520 of the receiver 500 to form the monoplanar receiver sub-assembly 23 in a shipping state configuration.

With reference to FIGS. 95-100, the lower turret 550 of the monoplanar bone anchor assembly 24 is generally similar to the lower rocker of monoplanar bone anchor assembly 24 described above, in that lower turret 550 also includes a ring-shaped body 552 having a central opening 553 and integral upper cap structures 560 located above opposed triangularly-shaped downwardly-extending skirt portions 554. The triangular skirt portions 554 also point downward to define bottom apex edges 556 that are configured to rest upon the upward-facing annular step surface 523 of the internal cavity 508 of the receiver 500, thereby providing a spaced-apart two-point pivot reference that allows for the lower turret 550 to stably pivot back and forth within the internal cavity 508. The upper cap structures 560 of the lower turret 550 also have inner portions 562 that overlie and partially close or square the central opening 553 of the ring-shaped body 552, with the downward-facing planar underside surfaces 566 of the inner portions 562 of the upper cap structures 560 also being configured to engage with the annular planar top surface 62 of the threaded universal shank head 60, and with the curved top surfaces 568 of the upper cap structures 560 being configured for engagement by the bottom surface of the upper insert 570.

However, the lower turret 550 of monoplanar bone anchor assembly 24 can differ from the lower rocker 250 described above, in that the lower interior surface 558 of the ring-shaped body 552 and triangular skirt portions 254 can include an underside thread 559 that matches the lower thread form 512 of the receiver 500, so that the threaded universal shank head 60 can become threadably engaged with the lower turret 550 after passing through the lower thread form 512 located on the partial spherical lower seating surface 510 of the monoplanar receiver 500. In addition, the lower turret 550 does not include inwardly-facing horizontally-elongate planar guide surfaces configured to engage with complementary surfaces formed into the underside surface of the upper insert 570, so that the lower turret 550 is instead free to rotate within the internal cavity 508 of the monoplanar receiver 500 relative to the upper insert 570 and to the monoplanar receiver 500.

Figure 101:
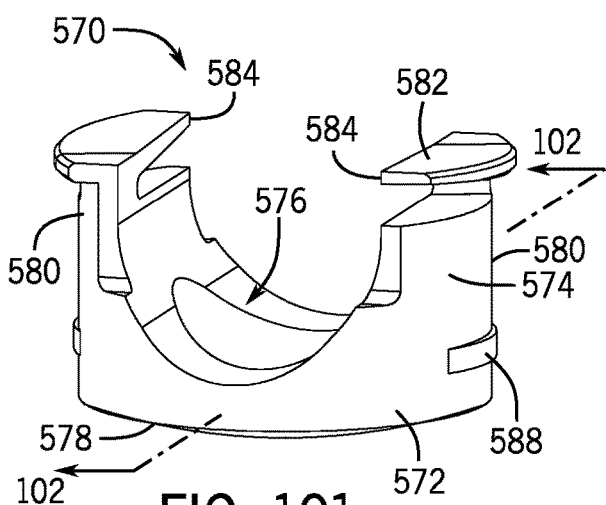
FIG. 101 is an upper perspective view of the upper insert piece of the monoplanar insert shown in FIG. 90.
Figure 102:
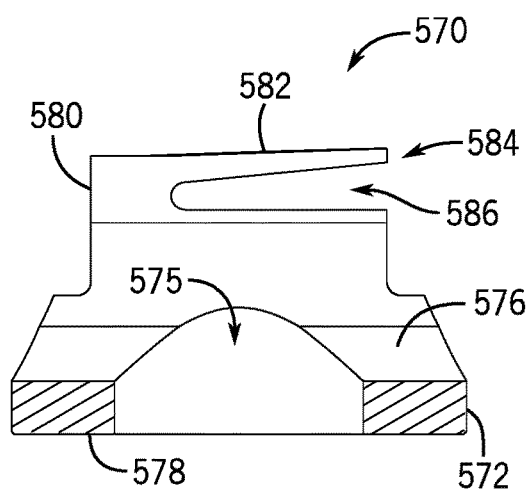
FIG. 102 is a cross-sectional side view of the upper insert piece of the monoplanar insert shown in FIG. 90.

With reference to FIGS. 101-102, the axially-biasing upper insert 570 of monoplanar bone anchor assembly 24 is similar to the axially-biasing multiplanar insert 470 included in the multiplanar bone anchor assembly 22 described above, in that the upper insert 570 includes a lower base portion 572 with two insert arms 580 extending upward from the lower base portion 572, with the base portion 572 and insert arms 580 together defining a cylindrical outer surface 574 that is sized to be slidably received within the central bore 520 of the multiplanar receiver 500. The upper insert 570 also includes a upward-facing curved saddle surface 576 extending between the insert arms 580 that is engageable with the elongate rod. However, the downwardly-facing bottom surface 578 of the lower base portion 572 can be substantially flat and planar. The upper insert 570 further includes a central tool-receiving aperture 575 defined by an inner cylindrical surface that configured to slidably receive a drive tool (not shown) that extends downwardly through the central bore 520 to engage the internal drive socket 54 formed into the top end 51 of the threaded universal shank head 60, as well as the outwardly projecting nubs 588 that are configured for rotation into the side pockets 524 formed into the central bore 520 of the monoplanar receiver 500.

The insert arms 580 of the upper insert 570 can also include integral flanges 584 that project radially outward from the top portions of the insert upright arms 580 with top surfaces 582 that are configured to rotate under the downward-facing upper arcuate surfaces 529 of the discontinuous recess 527 formed into the central bore 520 of the monoplanar receiver 500. In one aspect the flanges 584 can further comprise integral upwardly-angled spring-like structures, with the top surfaces 582 being configured to resiliently engage with the downward-facing upper arcuate surfaces 529 of the discontinuous recess 527 so as to provide a downwardly-directed force that biases the upper insert 570 against the curved top surfaces 568 of the lower turret 550. In one aspect this modification can include forming a slot 586 extending inward from the trailing edge of the insert upright arms 580 and just below the radially projecting flanges 584, and then bending the trailing end of each flange upward to form the upwardly-angled spring-like structures.

Figure 103:
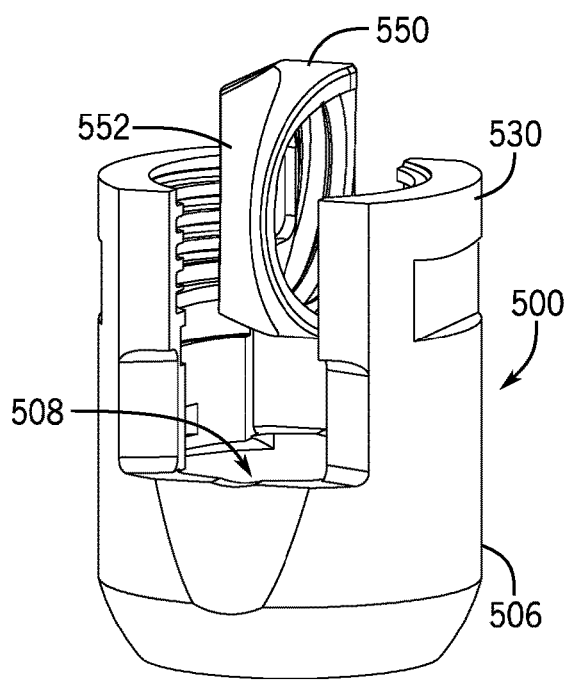
FIG. 103 is a perspective view of the monoplanar receiver and insert of FIG. 90 during assembly of the lower turret piece into the central bore of the monoplanar receiver.
Figure 104:
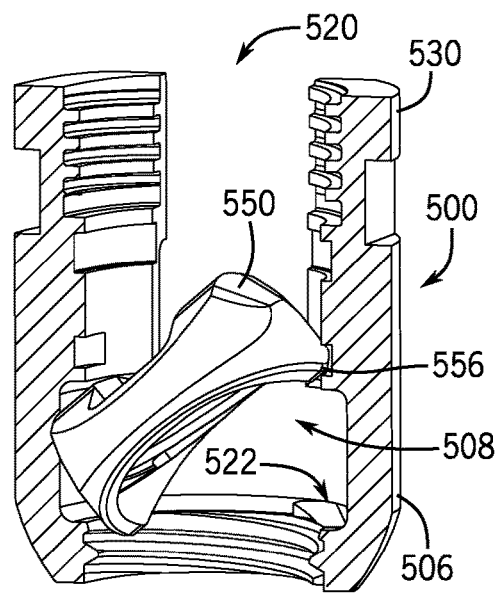
FIG. 104 is a partially cut-away perspective view of the monoplanar receiver and insert of FIG. 90 during assembly of the lower turret piece into the central bore of the monoplanar receiver.
Figure 105:
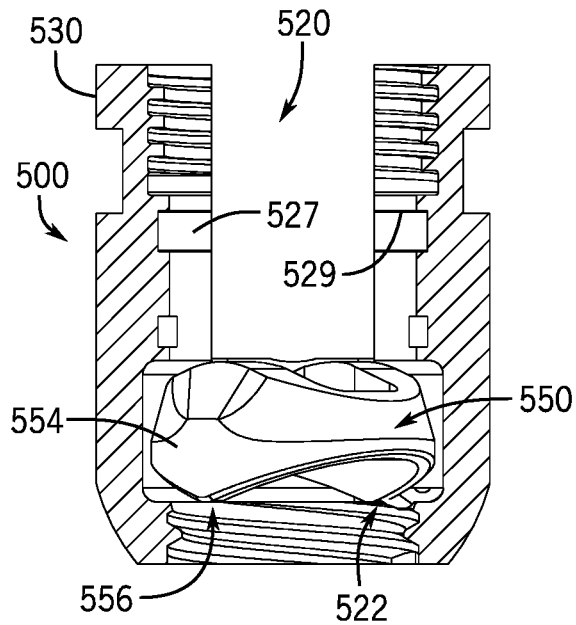
FIG. 105 is a partially cut-away perspective view of the monoplanar receiver and insert of FIG. 90 after assembly of the lower turret piece into the central bore of the monoplanar receiver.

With reference to FIGS. 103-105, the lower turret 550 can be assembled first into the monoplanar receiver 500 by rotating the ring-shaped body 552 to vertical until its top and bottom surfaces are aligned with the inner surfaces of the upright arms 530 of the monoplanar receiver 500. The lower turret 550 can then be dropped downward into the internal cavity where it is rotated back to horizontal, and where the bottom apex edges 556 of the triangularly-shaped downwardly-extending skirt portions 554 are positioned into the upward-facing triangular divots 522 that are formed into the upward-facing annular step surface 523. With reference back to FIGS. 93-94, the triangular divots 522 can intentionally be located at angular locations that are neither aligned with nor perpendicular to the transverse axis that defines the rod channel 536 of the monoplanar receiver 500, and instead are located on an axis that is intermediate between the two. As shown in FIG. 105, this can initially position the pivot axis of the lower turret 550 at an offset angular position, as defined by the bottom apex edges 556 of the skirt portions 554, and with the underside thread 559 of the lower turret 550 being aligned with the lower thread form 512 of the internal cavity 508.

Figure 106:
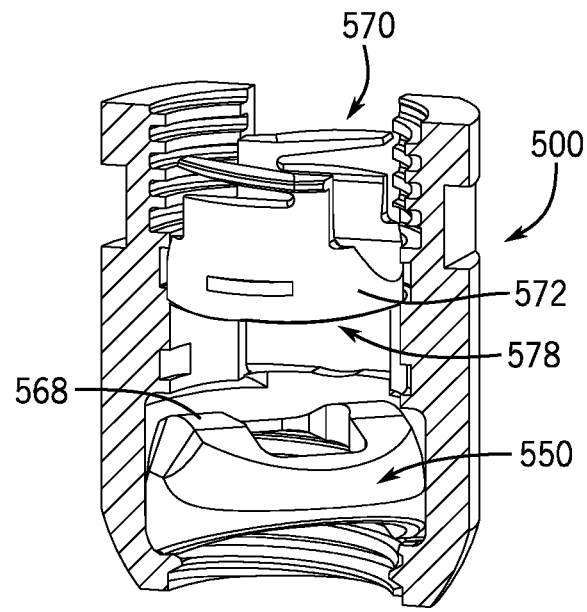
FIG. 106 is a partially cut-away perspective view of the monoplanar receiver and insert of FIG. 90 during assembly of the upper insert piece into the central bore of the monoplanar receiver.
Figure 107:
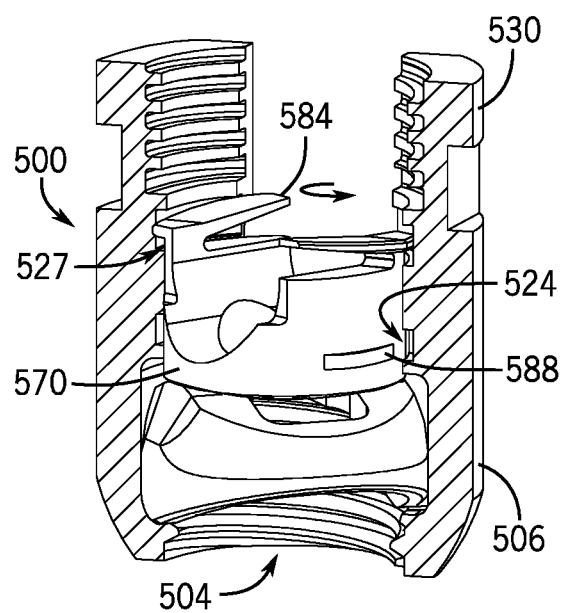
FIG. 107 is another partially cut-away perspective view of the monoplanar receiver and insert of FIG. 90 during assembly of the upper insert piece into the central bore of the monoplanar receiver.
Figure 108:
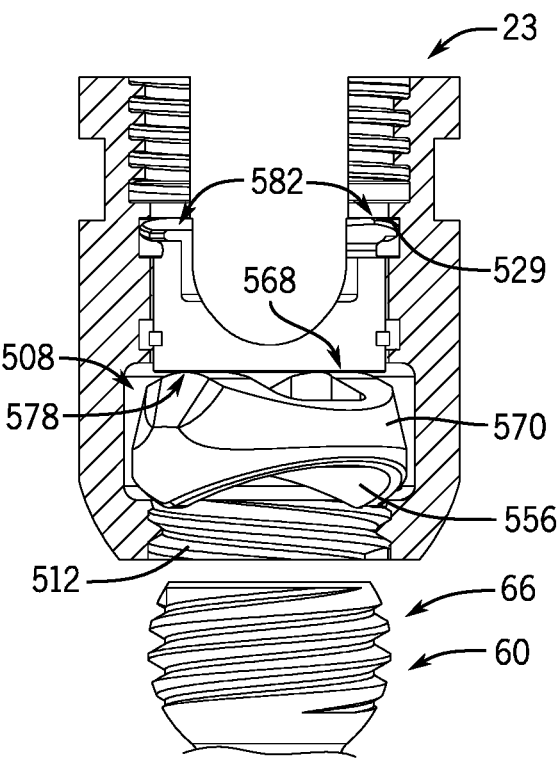
FIG. 108 is a partially cut-away perspective view of the monoplanar receiver and insert of FIG. 90 after assembly of the lower turret piece and upper insert piece into the central bore of the monoplanar receiver to form the completed monoplanar receiver sub-assembly.

As shown in FIGS. 106-108, the upper insert 570 can then be downloaded through the rod channel 538 and central bore 520 of the monoplanar receiver 500 until the annular planar bottom surface 578 of the upper insert 570 abuts the curved top surfaces 568 of the lower turret 550. The upper insert 570 can then be rotated through about a 90 degree range (approximately ¼ turn) around the vertical centerline axis of the receiver 500, with the outwardly-projecting flanges 584 rotating into the discontinuous recess 527 so that the top surfaces 582 of the flanges 584 are aligned with the downward-facing upper arcuate surfaces 529 of the recess 527, and with the outwardly projecting nubs 588 rotating into the opposed side pockets 524 formed into the central bore 520 to prevent further rotation of the upper insert 570 relative to the monoplanar receiver 500.

The pre-assembly of the individual monoplanar receiver 500, lower turret 550, and upper insert 570 components into the monoplanar receiver sub-assembly 23 into the shipping state condition is now complete. With reference to FIG. 108-110, the shank head 60 can then be threadably uploaded into the internal cavity 508 of the monoplanar receiver sub-assembly 13, through to the upper thread form 66 of the shank head 60 clearing and releasing from the lower thread form 512 of the internal cavity 508 while simultaneously engaging with the underside thread 559 of the lower turret 550, so as to become both pivotably and rotationally secured to the lower turret 550 within the monoplanar receiver sub-assembly 23. It will be appreciated that the resilient connection between the radially projecting flanges 584 of the upper insert 570 and the upper arcuate surfaces 529 of the discontinuous recess 527 of the monoplanar receiver 500 can also provide an additional tolerance for upward movement of the lower turret 550 during the uploading of the threaded universal shank head 60, so as to allow the upper thread form 66 of the shank head 60 to clear and release from the lower thread form 512 of the internal cavity 508 while simultaneously engaging with the underside thread 559 and planar underside surfaces 566 of the lower turret 550.

Upon the threaded uploading of the shank head 60 into the internal cavity 508, as shown in FIG. 109-110, the annular planar top surface 62 of the shank head 60 can engage the planar underside surfaces 566 of the upper cap structures 560 of the lower turret 550, but only after the upper thread form 66 of the shank head 60 becomes threadably engaged with the underside thread 559 of the lower turret 550. As will be appreciated by one of skill in the art, these simultaneous engagements can serve to lock the shank head and lower turret 550 together so as to prevent any further pivotal or rotational motion between the shank 50 and the lower turret 550.

Rotation of the shank head 50 relative to the monoplanar receiver 500 in the direction opposite that required for insertion of the shank head will cause the bottom apex edges 556 of the downwardly-extending skirt portions 554 to slide up out of the upward-facing triangular divots 522 and onto the upward-facing annular step surface 523 of the internal cavity 508, which will cause the lower turret 550 to move slightly upward and compress the upper insert 570 and its outwardly-projecting flanges 584 against the upper arcuate surfaces 529 of the discontinuous recess 527. In response, the outwardly-projecting flanges 584 can resiliently deflect to create a downwardly-directed resistance or axially biasing force that presses back downward on the lower turret 550, driving the bottom apex edges 556 downward against the annular step surface 523 to automatically establish a pre-lock friction fit without any further manipulation or deployment of the monoplanar bone anchor assembly 24 with tooling.

With reference to the schematic diagram shown in FIG. 111, in one aspect the axial rotation of the coupled shank and lower turret 550 can be limited by the angular distance between the two triangular divots 522 formed into the upward-facing annular step surface 523. For example, the functional range of rotation can be limited to when the bottom apex edges 556 of the lower turret 550 are riding on the annular step surface 523 and spaced from the triangular divots 522. Depending on the angular length of the triangular divots 522, in one aspect this functional range can be at least about 110 degrees, although it is foreseen that functional ranges up to about 120 degrees or to about 130 degrees are also possible and considered to fall within the scope of the present disclosure. Accordingly, and as shown in the FIG. 111, the angular location of the functional range may be selected so that the pivot axis of the lower turret 550 can be aligned with the transverse axis of the rod channel 536 of the monoplanar receiver 500 toward one end of the range (see FIG. 109), and can be perpendicular to the transverse axis of the rod channel 36 toward the other end of the functional range (see FIG. 110). This can beneficially provide the surgeon or user of the bone anchor assembly with the option for aligning the pivotal motion of the monoplanar bone anchor assembly 24 with both the sagittal plane (FIG. 109) and the transverse plane (FIG. 100) of the patient, and with any pivot plane between the two.

Figure 112:
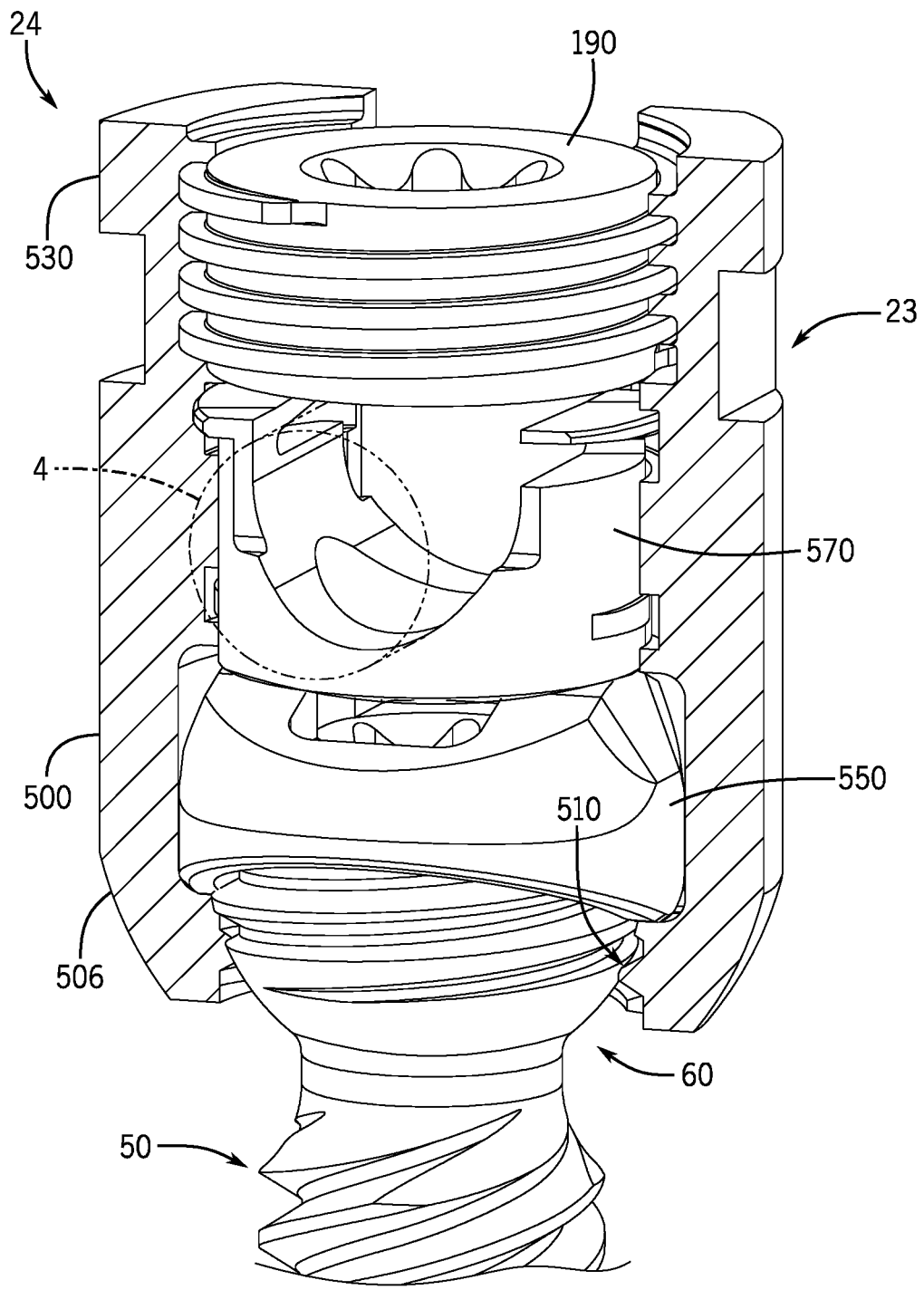
FIG. 112 is a partially cut-away perspective view of the aforementioned monoplanar receiver sub-assembly and shank after assembly together and with the elongate rod and closure of FIG. 90 into a fully assembled and locked monoplanar pivotal bone anchor assembly.

With reference to FIG. 112, upon the monoplanar receiver sub-assembly 23 being coupled to the shank head 60, the same elongate rod 4 described above can be positioned within the rod channel and the same closure 190 can then be threadably or otherwise secured into the rod channel 536 above the elongate rod 4 so as to apply a force or pressure against the upper surface of the elongate rod 4. This force or pressure can be transmitted downward through the elongate rod 4, the upper insert 570 and the lower turret 550 of the two-piece monoplanar insert, the upper surface portions of the threaded universal shank head 60, and ultimately through to the partial spherical lower seating surface 510 and base portion 506 of the monoplanar receiver 500, thereby locking both the elongate rod 4 and the bone anchor assembly 24 into a final locked position.

With reference to FIGS. 113 and 114-117, illustrated therein is another monoplanar bone anchor assembly 28 having an axially-biased, automatic or self-engaging friction fit, in accordance with a representative embodiment of the present disclosure. The monoplanar bone anchor assembly 28 can be similar to the monoplanar bone anchor assembly 24 described above, with the exception that the two-piece monoplanar insert comprising the rod-receiving upper insert 570' and the shank-engaging lower turret 550' can be modified so that the resilient spring-biasing elements that provide the downwardly-directed axially biasing force onto the lower turret 550' are now part of or associated with the lower turret 550' itself. As shown in the drawings, for example, separate spring elements 567 can project upward from the top surfaces 568 of the lower turret 550' to engage the annular planar bottom surface 578 of the upper insert 570' (which upper insert 570' can modified into a simple twist-in-place or snap-in-place type insert that is securable within the central bore 520 of the monoplanar receiver 500).

Figure 116:
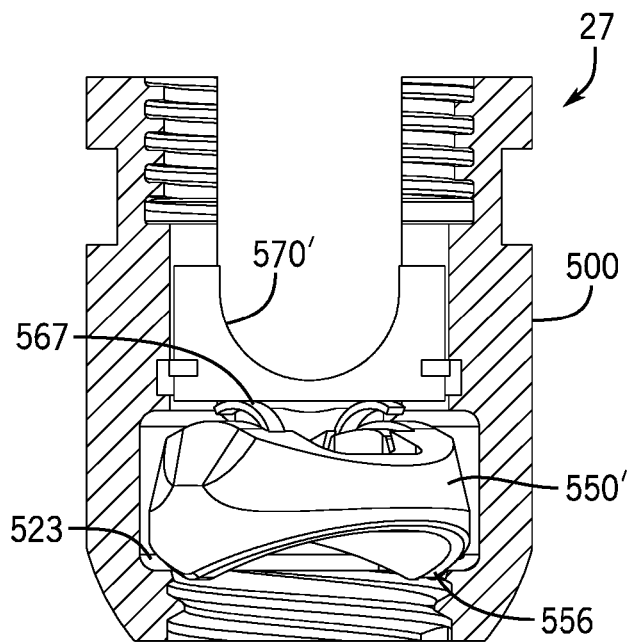
FIG. 116 is a partially cut-away front view of the monoplanar receiver and insert of FIG. 113 after assembly of the lower turret piece and upper insert piece into the central bore of the monoplanar receiver to form the completed monoplanar receiver sub-assembly.
Figure 117:
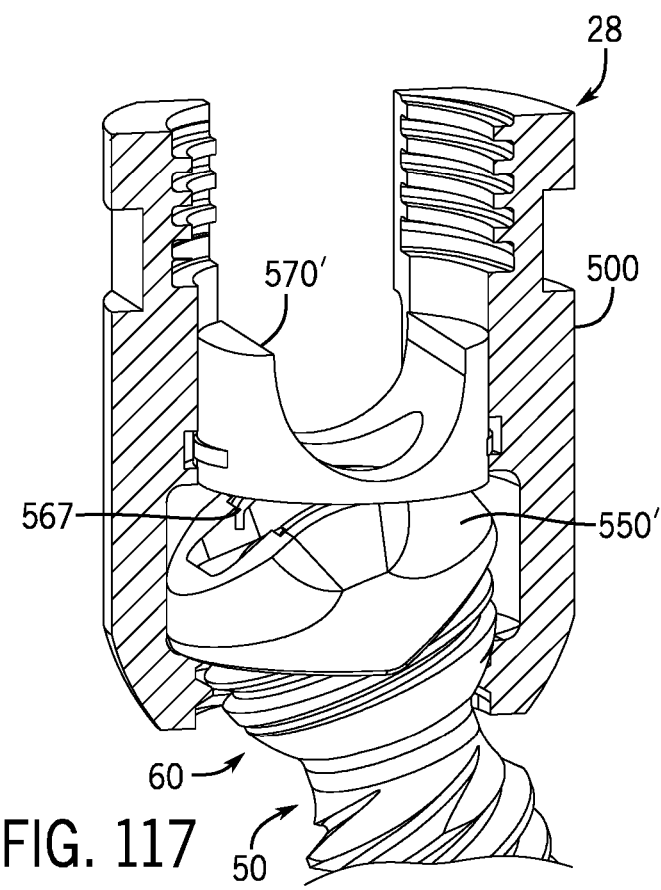
FIG. 117 is a partially cut-away perspective view of the aforementioned monoplanar receiver sub-assembly and the threaded universal shank head after being threadably coupled together.
Figure 121:
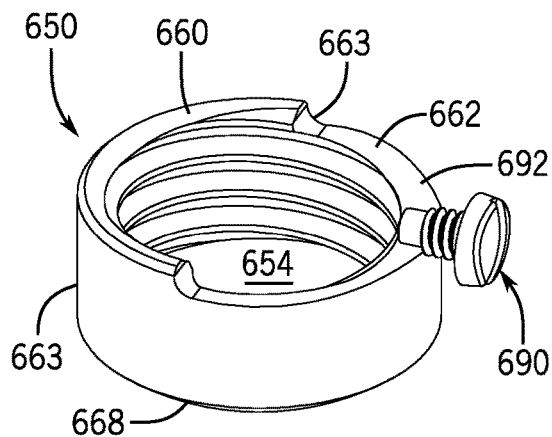

As shown in FIG. 116-117, the spring elements 567 can be resiliently deflected or compressed during assembly of the upper insert 570' down onto the lower turret 550' to create the downwardly-directed resistance or axially biasing force that presses back downward on the lower turret 550', driving the bottom apex edges 556 downward against the annular step surface 523 and thereby automatically establish the pre-lock friction fit. In addition, it will be appreciated that the resilient connection between the top surfaces 568 of the lower turret 550' and the bottom surface 578 of the upper insert 570' can provide an additional tolerance for upward movement of the lower turret 550' during the uploading of the threaded universal shank head 60, so as to allow the upper thread form 66 of the shank head 60 to clear and release from the lower thread form 512 of the internal cavity 508 while simultaneously engaging with the underside thread 559 and planar underside surfaces 566 of the lower turret 550'. The remaining structural elements of the lower turret 550' and the upper insert 570' and their interactions with the monoplanar receiver 500 can be the same as or similar to the structural elements and interactions of the monoplanar bone anchor assembly 24 discussed above.

With reference to FIGS. 118 and 119-128, illustrated therein is a non-pivotal or monoaxial bone anchor apparatus or assembly 26 having an axially-biased, automatic or self-engaging pre-lock friction fit, in accordance with another representative embodiment of the present disclosure. The non-pivotal bone anchor assembly 26 can be similar to the non-pivotal bone anchor assembly 16 described above, with the exception that the top edge 660 of the rotatable retainer or sleeve 650 may be modified to include a cutout 662 having an arc length of about 180 degrees, the non-pivotal receiver 600 can be provided with a threaded side aperture 640 that is configured to receive a small set screw 690 having a tip 692 with a smooth finish and with a wider circumferential recess 624, and an additional wave spring 680 can be added to the assembly 24 for positioning between the bottom edge 668 of the rotatable retainer or sleeve 650 and the snap-in-place retainer 670.

As shown in the drawings, the threaded side aperture 640 of the non-pivotal receiver 600 can be located at the upper end of the internal cavity 608, immediately below the downward facing lower discontinuous annular surface 627 that is engaged by the upper edge 660 of the rotatable sleeve 650 when the sleeve 650 is uploaded into the non-pivotal receiver 600 through the bottom opening 604. Upon insertion of the set screw 690 into the side aperture 640, the smooth tip 692 of the set screw 690 can project a short distance into the internal cavity 608. The rotatable sleeve 650 can also be uploaded into the internal cavity 608 with the cutout 662 being aligned with the tip 692 of the set screw 690 so that once positioned within the internal cavity 609, the range of rotation of the sleeve 650 is limited by the engagement between end surfaces 663 of the cutout 662 and the tip 692 of the set screw 690, thereby making the sleeve 650 only partially rotatable once installed within the internal cavity 608.

Figure 122:
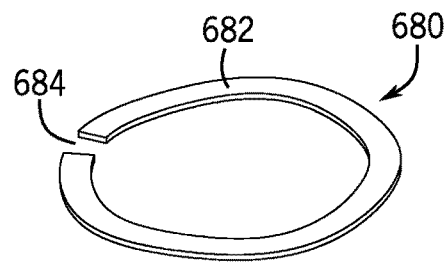
Figure 123:
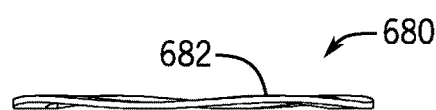
Figure 124:
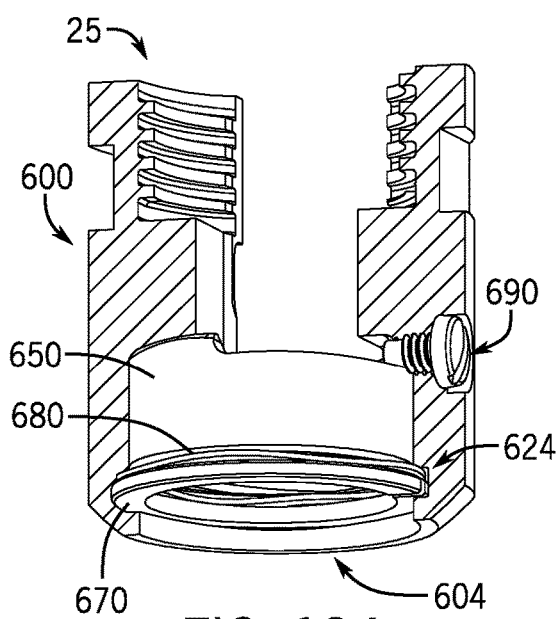
Figure 125:
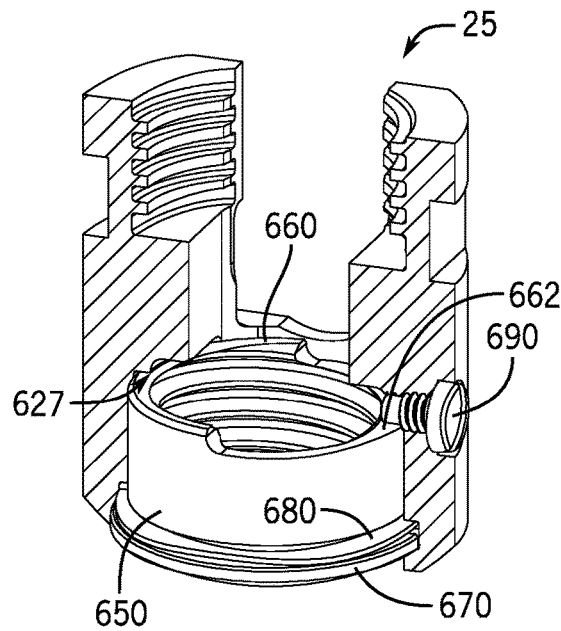

The wave spring 680 shown in FIGS. 122-123 can comprise a ring body 682 having a wavy profile in the axial direction that provides for resilient axial compression of the ring body 682 into a flattened state, thereby creating an axially biasing force that resists the compression. Similar to the snap-in-place retainer 670, the wave spring 680 can also include a slot or gap 684 that allows for radial compression of the wave spring 680 so that it can be uploaded into the internal cavity 608 of the non-pivotal receiver 600 below the rotatable sleeve 650 in a radially-compressed state, and then released to snap outward into the circumferential recess 624 at the lower end of the internal cavity 608. As described above, the snap-in-place retainer 670 can be uploaded into the internal cavity 608 in a similar fashion, either together with or after the wave spring 680, and released to snap outward into the circumferential recess 624 so as to prevent the both the wave spring 680 and the rotatable sleeve 650 from sliding back out the bottom opening 604, as shown in FIGS. 124-125.

With both the wave spring 680 and the snap-in-place retainer 670 being securing in the circumferential recess 624 below the partially rotatable sleeve 650, the non-pivotal receiver sub-assembly 25 is now in a shipping state configuration, with the threaded central aperture 654 of the sleeve 650 being stabilized and centralized just above or within the bottom opening 604 of the non-pivotal receiver 600 by the snap-in-place retainer 670. In addition, in one aspect the internal cavity 608 and circumferential recess 624 can be sized so that the wave spring 680 can be partially axially compressed between the snap-in-place retainer 670 and the bottom edge 668 of the retainer or sleeve 650, thereby pushing the sleeve upwards until the portion of the top edge 660 of the sleeve 650 without the cutout engages the lower discontinuous annular surface 627 located below the upper end of the internal cavity 608. This engagement can be controlled or dimensioned so that the partially rotatable sleeve 650 is only lightly restricted from rotating within the angular range defined by the cutout 662.

With reference to FIGS. 126-127, the threaded universal shank head 60 can now be threadably uploaded into the partially rotatable sleeve 650 that is itself, in turn, held within internal cavity 608 of the non-pivotal receiver 600 by the snap-in-place retainer 670, so as to become coupled or secured to the non-pivotal receiver sub-assembly 15. Because the partially rotatable sleeve 650 is only lightly secured against rotation by the wave spring 680, the applied torque produced by the engagement of the threads can cause the sleeve 650 to rotate slightly until one end of the cutout 660 engages the tip 692 of the set screw 690, which engagement then prevents further rotation of the sleeve 650 within the internal cavity 608.

Upon the completion of the threaded uploading of the shank head 60 into the partially rotatable sleeve 650, the annular planar top surface 62 of the shank head can project above the top surface of the sleeve 650 to become engaged with a downward facing upper discontinuous annular surface 629 that can, in turn, define the upper end of the internal cavity 608. As such, any over-torquing of the shank head 60 relative to the rotatable sleeve 650 can then drive the rotatable sleeve 650 downward to bear against the wave spring 680 and snap-in-place retainer 670, so as to automatically create the axially biasing force that establishes the pre-lock rotational friction fit. While the non-pivotal receiver sub-assembly 25 is still only free to rotate through the angular range defined by the cutout 662, the 180 degree angular range of the cutout can be sufficient for the surgeon or medical professional to align the rod channel 636 of the non-pivotal receiver 600 in any desired direction with an applied twisting force.

Upon the non-pivotal receiver sub-assembly 25 being coupled to the shank head 60, the same elongate rod 4 described above can be positioned within the rod channel 636 and the same closure 190 can then be threadably or otherwise secured into the rod channel 636 above the elongate rod 4 so as to apply a force or pressure against the upper surface of the elongate rod 4. This force or pressure can transmitted downward through the elongate rod 4 and directly onto the planar top surface 62 of the shank head 60, and from there through the shank head, the rotatable sleeve 650, and ultimately through snap-in-place retainer 670 to the cylindrical base portion 606, thereby locking both the elongate rod 4 and the bone anchor assembly 26 into a final locked position, as shown in FIG. 128.

Figure 129:
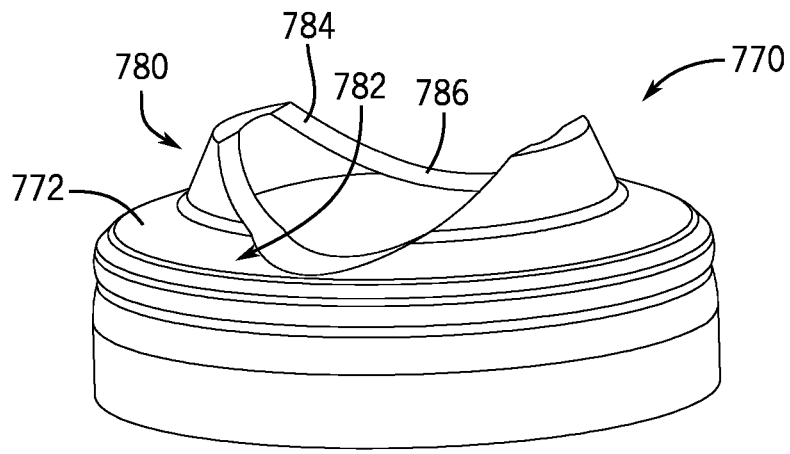
Figure 130:
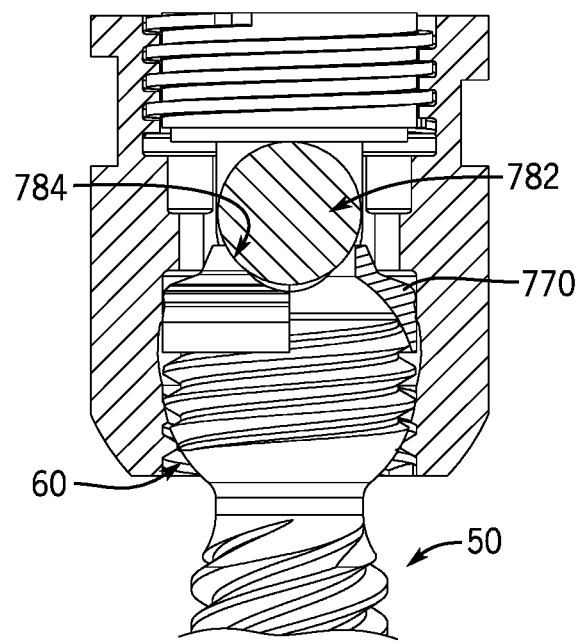
Figure 131:
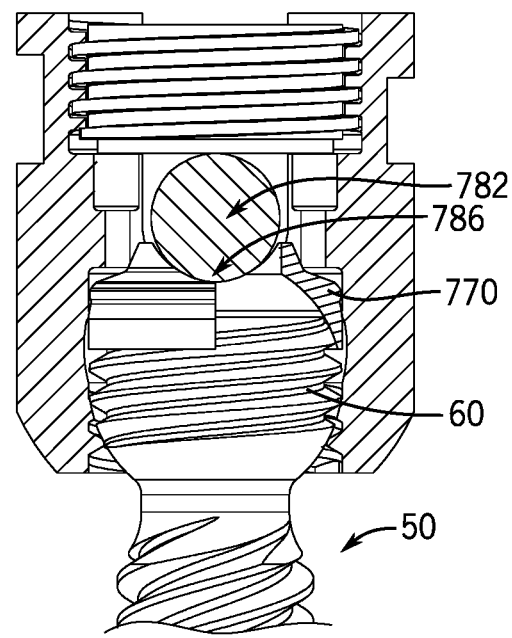

Illustrated in FIG. 129 is another embodiment of the multiplanar insert or pressure ring 770 that can be used with the multiplanar bone anchor assembly 12 discussed above. The multiplanar pressure ring 770 includes a top surface 772 having one or more curvate surfaces 780 forming an insert rod channel 782 that is configured to closely receive a lower portion of the elongate rod. Moreover, as shown in FIGS. 130-131, the pressure ring 770 can include a hybrid insert rod channel 782 or saddle that is configured to receive rods of differing size. For example, in one aspect the upper outer portions 784 of the insert rod channel 782 can have a radius of curvature configured to closely receive and center a 5.0 mm rod (FIG. 131), while the center portion 786 of the insert rod channel 782 can have a radius of curvature configured to closely receive and center a 4.5 mm rod (FIG. 131). Other configurations for the different radii of curvature, such as for larger or smaller rods, are also contemplated and configured to fall within the scope of the present disclosure.

Similarly, illustrated in FIG. 132 is another embodiment of the axially-biasing multiplanar insert 870 that can be used with the multiplanar bone anchor assembly 22 discussed above. The multiplanar insert 870 can also include a hybrid insert rod channel 876 or saddle that is configured to receive rods of differing size. For example, in one aspect the upper outer portions 884 of the insert rod channel 776 can have a radius of curvature configured to closely receive and center a 5.0 mm rod (FIG. 133), while the center portion 886 of the insert rod channel 876 can have a radius of curvature configured to closely receive and center a 4.5 mm rod (FIG. 131). Other configurations for the different radii of curvature, such as for larger or smaller rods, are also contemplated and configured to fall within the scope of the present disclosure.

Illustrated in FIGS. 135-139 are additional alternative embodiments for interchangeable closures and insert combinations that may be used with the multiplanar bone anchors of the modular spinal fixation system of the present disclosure. For instance, one embodiment can include a single-piece closure 790 having a solid body 792 and a bottom surface with a downwardly-extending center portion 794 configured to engage the elongate rod 4. Another embodiment can include a multi-piece closure 890 having an outer ring 892 with a bottom surface 894 configured to engage with top surfaces 982 of insert arms 980 of a multiplanar pressure insert 970 that can extend above an upper surface of the elongate rod 4 that is received within the insert channel 976 (see FIG. 139), and a center screw 896 having a closed-off bottom surface 898 configured to engage the elongate rod 4. In one aspect the insert 970 can be a multiplanar insert having a base portion similar to the multiplanar insert 170 described above, with a lower cylindrical portion 975 and a circumferential recess 976 that is sized and shaped to receive the discontinuous retaining ridge projecting inward from the sidewall surfaces of the internal cavity of the receiver, and a partial spherical lower surface 971 that is configured to directly engage the upper portion of the partial spherical outer surface of the threaded universal shank head 60, as shown in FIG. 139. The interchangeable closures and insert combinations can be configured to provide a full lock with the single-piece closure 790 as shown in FIG. 139(a), a screw lock only with the multi-piece closure 890 as shown in FIG. 139(b), or a screw and rod lock with the multi-piece closure 890, as shown in FIG. 139(c). Other configurations of closures and inserts are also contemplated and configured to fall within the scope of the present disclosure.

As indicated above, the modular spinal fixation system of the present disclosure has been described herein in terms of preferred embodiments and methodologies considered by the inventors to represent best modes of carrying out the one or more inventions disclosed herein. It will be understood by the skilled artisan, however, that a wide range of additions, deletions, and modifications, both subtle and gross, may be made to the illustrated embodiments of the bone anchor assemblies and modular spinal fixation system and to the representative type of universal shank head, and that these and other revisions might be made by those of skill in the art without departing from the spirit and scope of the one or more inventions that are to be constrained only by their respective claims.

What is claimed is:

1. A universal shank head system for securing a fixation rod to a bone of a patient with closures, the universal shank head system comprising:
  a plurality of bone anchors, each bone anchor comprising
    a longitudinal axis, a shank head at a proximal end, and an anchor portion at a distal end configured for fixation to the bone, the shank head including a planar top surface at an upper end of the shank head and a rounded outer side surface extending downward from the planar top surface to a neck portion that connects the shank head to the anchor portion; and
  a plurality of pivoting and non-pivoting receiver sub-assemblies, each receiver sub-assembly including:
    a receiver having a vertical centerline axis, an upper portion defining a channel configured to receive the fixation rod, and a base defining a lower portion of a central bore formed around the vertical centerline axis and communicating with a bottom surface of the receiver through a bottom opening, the central bore extending upwardly from the bottom opening through the channel to a top of the receiver and including a guide and advancement structure mateable with a closure proximate the top of the receiver; and
    at least one of a shank head-engaging retainer or a rod-engaging insert positioned within the central bore around the vertical centerline axis,
  wherein each of the shank heads is configured for uploading into both the pivoting and non-pivoting receiver sub-assemblies through the bottom opening of the receiver, and for axial rotation about the longitudinal axis of the shank relative to the receiver prior to locking the receiver sub-assembly to the head of the shank with the fixation rod and a closure.

2. The universal shank head system of claim 1, wherein the plurality of pivoting receiver sub-assemblies further comprises at least one multiplanar receiver sub-assembly and at least one monoplanar receiver sub-assembly.

3. The universal shank head system of claim 1, wherein each bone anchor further comprises a shank having an internal drive structure extending inward from the top surface and configured to mate with a drive tool.

4. The universal shank head system of claim 3, wherein each shank includes a central bore extending from the internal drive structure down to a bottom end of the anchor portion and configured to receive a guide wire, the anchor portion of the shank being configured for implantation in the bone about a guide wire with the drive tool prior to the shank head being uploaded into the central bore of the receiver through the bottom opening.

5. The universal shank head system of claim 1,
wherein each of the pivoting receiver sub-assemblies includes a rounded lower seating surface adjacent the bottom opening configured to receive and support the shank head, and at least one helically wound lower threadform formed into the rounded lower seating surface and extending downwards into the bottom opening toward a lower start structure adjacent the bottom surface, and
wherein each of the shank heads includes at least one helically wound upper threadform formed into the rounded outer side surface and extending upwards toward an upper start structure with a concave surface adjacent the planar top surface, the shank heads being configured for rotatable threadable uploading through the bottom opening and the lower seating surface until the upper threadform on the shank head passes through and clears the lower threadform of the receiver and the shank head is pivotably captured within the lower portion of the central bore of the receiver.

6. The universal shank head system of claim 5, wherein each of the pivoting receiver sub-assemblies includes a rod-engaging insert positioned within the central bore above the shank head.

7. The universal shank head system of claim 1,
wherein each of the non-pivoting receiver sub-assemblies includes a shank head-engaging retainer configured for uploading through the bottom opening of the receiver and for rotation with the lower portion of the central bore, the shank head-engaging retainer having a threaded central aperture with a bottom end centralized within the bottom opening and at least one helically wound lower threadform formed into the threaded central aperture and extending downwards toward a lower start structure formed into the bottom end of the central aperture, and
wherein each of the shank heads includes at least one helically wound upper threadform formed into the rounded outer side surface and extending upwards toward an upper start structure with a concave surface adjacent the planar top surface, the shank heads being configured for rotatable threadable uploading through the bottom opening of the receiver and into the threaded central aperture of the shank head-engaging retainer until the shank head is captured by the rotatable shank head-engaging retainer within the lower portion of the central bore of the receiver.

8. The universal shank head system of claim 7 and further comprising an open ring retainer configured to be snapped into a circumferential recess formed into the lower portion of the central bore of the each receiver below the rotatable shank head-engaging retainer so as to secure the rotatable shank head-engaging retainer within the receiver.

9. The universal shank head system of claim 1 and further comprising the fixation rod and the closures, wherein each of the closures is configured for positioning within the channel of each receiver above the fixation rod and in engagement with the guide and advancement structure to apply a downward pressure towards a top of the fixation rod, so as to frictionally lock the shank in a fixed position relative to the receiver.

10. A bone anchor system for securing an elongate rod to a bone of a patient, the universal bone anchor system comprising:
a plurality of bone anchors, each bone anchor comprising a longitudinal axis, a shank head at a proximal end having a rounded shape, and an anchor portion at a distal end configured for fixation to the bone, the shank head including a planar top surface at an upper end of the shank head, a rounded outer side surface extending downward from the planar top surface to a neck portion that connects the shank head to the anchor portion, and at least one helically wound upper threadform located on the rounded outer side surface and extending upwards toward an upper start structure with a concave surface adjacent the planar top surface;
at least one multiplanar receiver sub-assembly comprising:
a multiplanar receiver having an upper portion with a channel configured to receive the elongate rod, a base portion defining a lower portion of a central bore having a rounded lower seating surface adjacent a bottom opening and configured to receive and support a shank head of a first bone anchor, and at least one helically wound lower threadform located on the rounded lower seating surface and extending downwards into the bottom opening toward a lower start structure adjacent the bottom surface, and
a multiplanar insert positionable with the central bore of the multiplanar receiver above the shank head, the multiplanar insert including a planar top surface positionable within the channel and configured for engagement by the elongate rod and a bottom surface configured to engage the shank head of the first bone anchor while providing for multiplanar pivotal motion of the first bone anchor relative to the multiplanar receiver prior to locking the at least one multiplanar receiver sub-assembly with a closure, and
at least one monoplanar receiver sub-assembly comprising:
a monoplanar receiver having an upper portion with a channel configured to receive the elongate rod, a base portion defining a lower portion of a central bore having a rounded lower seating surface adjacent a bottom opening and configured to receive and support a shank head of a second bone anchor, and at least one helically wound lower threadform located on the rounded lower seating surface and extending downwards into the bottom opening toward a lower start structure adjacent the bottom surface, and
a monoplanar insert positionable with the central bore of the receiver above the shank head, the monoplanar insert including a planar top surface positionable within the channel and configured for engagement by the elongate rod and a bottom surface configured to engage the shank head of the second bone anchor while providing for monoplanar pivotal motion of the second bone anchor relative to the monoplanar receiver prior to locking the at least one monoplanar receiver sub-assembly with a closure, wherein the shank heads of the plurality of bone anchors are configured for threaded uploading into either of the at least one multiplanar receiver sub-assembly or the at least one uni-planar receiver sub-assembly without further modification or adjustment.

11. The bone anchor system of claim 10, wherein the at least one helically wound upper threadform located on the rounded outer side surfaces of the shank heads and threadably mateable with the at least one helically wound lower threadform located on the rounded lower seating surfaces of the receivers further comprise a pair of helically wound upper threadforms located on the rounded outer side surface of the shank head and threadably mateable with a pair of helically wound lower threadforms located on the rounded lower seating surfaces of the receivers, respectively.

12. The bone anchor system of claim 10,
wherein the monoplanar insert further comprises an upper insert piece slidably engageable with a lower rocker piece, and
wherein an engagement between the upper insert piece, the lower rocker piece, and the planar top surface of the shank head is configured to limit the pivotal motion of the monoplanar receiver sub-assembly relative to the shank head to a single plane while allowing for rotation of the monoplanar receiver sub-assembly about the longitudinal axis of the shank.

13. The bone anchor system of claim 10 and further comprising at least one non-pivotal receiver sub-assembly comprising:
a non-pivotal receiver having an upper portion with a channel configured to receive the elongate rod and a base portion defining a lower portion of a central bore having a bottom opening; and
a rotatable sleeve configured for uploading into the lower portion of the central bore and having a threaded central aperture with a bottom end centralized within the bottom opening of the non-pivotal receiver, and at least one helically wound lower threadform formed into the threaded central aperture and extending downwards toward a lower start structure formed into the bottom end of the central aperture,
wherein the shank heads of the plurality of bone anchors are configured for threaded uploading into the threaded central aperture of the rotatable sleeve, and
wherein the rotatable sleeve is configured to provide for rotatable motion of the non-pivotal receiver about the longitudinal axis of an uploaded bone anchor prior to locking the at least one non-pivotal receiver sub-assembly with a closure.

14. The bone anchor system of claim 13 and further comprising an open ring retainer configured to be snapped into a circumferential recess formed into the lower portion of the central bore of the non-pivotal receiver below the rotatable sleeve, so as to secure the rotatable sleeve within the non-pivotal receiver.

15. A method of assembling a universal shank head system configured for securing a fixation rod to a bone of a patient with closures, the method comprising:
uploading one of a plurality of bone anchors into a lower portion of a central bore of one of a plurality of pivoting and non-pivoting receiver sub-assemblies, each of the plurality of bone anchors comprising a longitudinal axis, a shank head at a proximal end, and an anchor portion at a distal end configured for fixation to the bone, the shank head including a planar top surface at an upper end of the shank head and a rounded outer side surface extending downward from the planar top surface to a neck portion that connects the shank head to the anchor portion, each of the plurality of pivoting and non-pivoting receiver sub-assemblies including:
a receiver having a vertical centerline axis, an upper portion defining a channel configured to receive the fixation rod, and a base defining the lower portion of the central bore formed around the vertical centerline axis and communicating with a bottom surface of the receiver through a bottom opening, the central bore extending upwardly from the bottom opening through the channel to a top of the receiver and including a guide and advancement structure mateable with a closure proximate the top of the receiver; and
at least one of a shank head-engaging retainer or a rod-engaging insert positioned within the central bore around the vertical centerline axis,
wherein the shank head of each of the plurality of bone anchors is configured for uploading into both the pivoting and non-pivoting receiver sub-assemblies through the bottom opening of the receiver, and for axial rotation about the longitudinal axis of the shank relative to the receiver prior to locking the receiver sub-assembly to the head of the shank with the fixation rod and a closure.

16. The method of claim 15, further comprising selecting a pivoting receiver sub-assembly from the group consisting of at least one multiplanar receiver sub-assembly and at least one monoplanar receiver sub-assembly.

* * * * *